(12) United States Patent
Seifert et al.

(10) Patent No.: US 8,114,970 B2
(45) Date of Patent: Feb. 14, 2012

(54) SYNTHETIC HEPARIN MONOSACCHARIDES

(75) Inventors: Joachim Seifert, Forest Lake (AU); Latika Singh, Forest Lake (AU); Tracie E. Ramsdale, Sunnybank (AU); Michael L. West, Birkdale (AU); Nicholas B. Drinnan, Highgate Hill (AU)

(73) Assignee: Alchemia Limited, Eight Mile Plains (AU)

( * ) Notice: Subject to any disclaimer, the term of this patent is extended or adjusted under 35 U.S.C. 154(b) by 416 days.

(21) Appl. No.: 12/354,643

(22) Filed: Jan. 15, 2009

(65) Prior Publication Data

US 2009/0187013 A1 Jul. 23, 2009

Related U.S. Application Data

(62) Division of application No. 10/488,677, filed as application No. PCT/AU02/01228 on Sep. 6, 2002, now Pat. No. 7,541,445.

(30) Foreign Application Priority Data

Sep. 7, 2001 (AU) .......................................... 7587

(51) Int. Cl.
*C07H 15/18* (2006.01)
*C07H 15/203* (2006.01)
(52) U.S. Cl. ...................... 536/17.2; 536/17.3; 536/17.9
(58) Field of Classification Search .................... None
See application file for complete search history.

(56) References Cited

U.S. PATENT DOCUMENTS

| 4,401,662 | A | 8/1983 | Lormeau et al. |
|---|---|---|---|
| 4,496,550 | A | 1/1985 | Lindahl et al. |
| 4,607,025 | A | 8/1986 | Petitou et al. |
| 4,818,816 | A | 4/1989 | Petitou et al. |
| 5,939,588 | A | 8/1999 | Soloshonok et al. |
| 6,538,117 | B1 * | 3/2003 | Wong et al. ................. 536/18.5 |
| 684,691 | A1 | 1/2005 | Seeberger et al. |
| 7,541,445 | B2 * | 6/2009 | Seifert et al. .................... 536/21 |
| 2003/0013862 | A1 | 1/2003 | Seeberger et al. |
| 2005/0080042 | A1 | 4/2005 | Seifert et al. |
| 2005/0187381 | A1 | 8/2005 | Seeberger et al. |

FOREIGN PATENT DOCUMENTS

| AU | 10397/83 | | 8/1983 |
|---|---|---|---|
| AU | 42637/85 | A | 11/1985 |
| EP | 0 082 793 | A1 | 6/1983 |
| EP | 0 082 793 | B1 | 6/1983 |
| EP | 0 084 999 | A1 | 4/1988 |
| EP | 0 084 999 | B1 | 4/1988 |
| EP | 0 333 243 | A2 | 9/1989 |
| FR | 2 531 436 | A1 | 2/1984 |
| JP | 63-218691 | A | 9/1988 |
| JP | 3-237101 | A | 10/1991 |
| JP | 10-182578 | A | 7/1998 |
| WO | WO-82/03863 | A1 | 11/1982 |
| WO | WO-95/03316 | A2 | 2/1995 |

OTHER PUBLICATIONS

Greene et al., "Protective groups in ORganic Synthesis" published 1999 by John Wiley and Sons, pp. 76-87 and 173-178.*
Takahashi et al., "Synthesos of a Potential Heparinase Inhibitor" Chemistry Letters (1994) pp. 2119-2122.*
D'Souza et al., "Conversion of Pyranose Glycals to Furanose Derivatives: A New Route to Oligofuranosides" Journal of Organic Chemistry (1998) vol. 63 pp. 9037-9044.*
Benalki et al., "Oxazolidinone Protected 2-Amino-2-deoxy-D-glucose Derivatives as Versatile Intermediates in Stereoselective Oligosaccharide Synthesis and the Formation of r-Linked Glycosides" J. Am. Chem. Soc. (2001) vol. 123 pp. 9461-9462.*
Basten, J. et al. (1992). "Biologically Active Heparin-like Fragments with a 'Non-Glycosamino'glycan Structure. Part 2: A Tetra-O-Methylated Pentasaccharide with High Affinity for Antithrombin III," *Bioorg. Med. Chem. Lett.* 2(9):901-904.
Beetz, T. et al. (1986). "Synthesis of an Antithrombin Binding Heparin-Like Pentasaccharide," *Tetrahedron Letters* 27(48):5889-5892.
Choay, J. et al. (1981). "Structural Studies on a Biologically Active Hexasaccharide Obtained from Heparin," *Annals of New York Academy of Sciences* pp. 644-648.
Choay, J. et al. (Oct. 31, 1983). "Structure-Activity Relationship in Heparin: A Synthetic Pentasaccharide with High Affinity for Antithrombin III and Eliciting High Anti-Factor Xa Activity," *Biochemical and Biophysical Research Communications* 116(2):492-499.
Duchaussoy, P. et al. (1991). "The First Total Synthesis of the Antithrombin III Bidning Site of Porcine Mucosa Heparin," *Bioorg. Med. Chem. Lett.* 1(2):99-102.
Greene et al. (1999). *Protective Groups in Organic Synthesis*, Second Edition, John Wiley and Sons, Inc.: New York, NY, pp. 46-52, 88-92, and 413-420.
Greene et al. (1999). *Protective Groups in Organic Synthesis*, Second Edition, John Wiley and Sons, Inc.: New York, NY, pp. 42-46, 53-54, 83-84, 100-103 and 413-452.
Ichikawa et al. (1986). "Synthesis of a Heparin Pentasaccharide Fragment with a High Affinity for Antithrombin III Employing Cellobiose as a Key Starting Material," *Tetrahedron Letters* 27(5):611-614.
Ichikawa, Y. et al. (1988). "Synthesis of Methyl Glycoside Derivatives of Tri- and PentaSaccharides Related to the Antithrombin III-Binding Sequence of Heparin, Employing Cellobiose as a Key Starting-Material," *Carb. Res.* 172(1):37-64.
International Search Report mailed Jan. 13, 2003 for PCT Application No. PCT/AU02/01228, 6 pages.
Jaurand, G. et al. (Sep. 1992). "Biologically Active Heparin-like Fragments with a "Non-Glycosamino"Glycan Structure. Part 1: A Pentasaccharide Containing a 3-O-Methyl Iduronic Acid Unit," *Bioorg. Med. Chem. Lett.* 2(9):897-900.
Lei, P-S. et al. (1998). "Synthesis of a 3-Deoxy-L-iduronic Acid Containing Heparin Pentasaccharide to Probe the Conformation of the Antithrombin III Binding Sequence," *Biororg. Med. Chem.* 6:1337-1346.
Lindahl, U. et al. (Nov. 1980). "Evidence for a 3-*O*-Sulfated D-Glucosamine Residue in the Antithrombin-Binding Sequence of Heparin," *Biochemistry* 77(11):6551-6555.

(Continued)

Primary Examiner — Eric S Olson
(74) *Attorney, Agent, or Firm* — Morrison & Foerster LLP

(57) ABSTRACT

Preparation of synthetic monosaccharides, for use in the preparation of synthetic heparinoids.

13 Claims, 2 Drawing Sheets

OTHER PUBLICATIONS

Love, K.R. et al. (2001). "Linear Synthesis of a Protected H-Type II Pentasaccharide Using Glycosyl Phosphate Building Blocks," *J. Org. Chem.* 66:8165-8176.

Lucas, H. et al. (1990). "Syntheses of Heparin-like Pentamers Containing "Opened" Uronic Acid Moieties," *Tetrahedron* 46(24):8207-8228.

Orgueira, H.A. et al. (2003). "Modular Synthesis of Heparin Oligosaccharides," *Chemistry* 9(1):140-169.

Petitou, M. (1984). "Synthetic Heparin Fragments: New and Efficient Tools for the Study of Heparin and its Interactions," *Nouv. Rev. Fr. Hematol.* 26:221-226.

Petitou, M. et al. (1986). "Synthesis of Heparin Fragments. A Chemical Synthesis of the Pentasaccharide $O$-(2-Deoxy-2-Sulfamido-6-$O$-Sulfo-$\alpha$-D-Glucopyranosyl)-(1→4)-$O$-($\beta$-D-Glucopyranosyluronic Acid)-(1→4)-$O$-(2-Deoxy-2-Sulfamido-3,6-Di-$O$-Sulfo-$\alpha$-D-Glucopyranosyl)-(1→4)-$O$-(2-$O$-Sulfo-$\alpha$-L-Idopyranosyluronic Acid)-(1→4)-2-Deoxy-2-Sulfamino-6-$O$-Sulfo-D-Glucopyranose Decasodium Salt, A Heparin Fragment Having High Affinity for Antithrombin III," *Carbohydrate Research* 147:221-236. (client).

Petitou, M. et al. (1987)/ "Synthesis of Heparin Fragments: A Methyl $\alpha$-Pentoside with High Affinity for Antithrombin III," *Carbohydrate Research* 167:67-75.

Petitou, M. et al., (1988). "Binding of Heparin to Antithrombin III: A Chemical Proof of the Critical Role Played by a 3-Sulfated 2-Amino-2-Deoxy-D-Glucose Residue," *Carbohydrate Res.* 179:163-172.

Petitou, M. et al. (1991)/ "A New, Highly Potent, Heparin-like Pentasaccharide Fragment Containing a Glucose Residue Instead of a Glucosamine," *Bioorg. Med. Chem. Lett.* 1(2):95-98.

Petitou, M. et al. (1992)/ "Chemical Synthesis of Heparin Fragments and Analogues," *Fortschr. Chem. Org. Naturst.* 60:143-210.

Riesenfeld, J. et al. (Mar. 10, 1981). "The Antithrombin-Binding Sequence of Heparin," *The Journal of Biological Chemistry* 256(6):2389-2394.

Sinay, P. et al. (1984). "Total Synthesis of a Heparin Pentasaccharide Fragment Having High Affinity for Antithrombin III," *Carbohydrate Research* 132:C5-C9.

STN File CA Abstract Accession No. 104:130179 & Ichikawa, Y. et al., "Synthetic studies on mucopolysaccharides. Part III. Synthesis, from cellobiose of a trisaccharide closely related to the GlcNAc—GlcA—GlcN segment of the antithrobin-binding sequence of heparin," Carbohydrate Research, 1985, pp. 272-282, vol. 141, No. 2.

STN File CA Abstract Accession No. 119:181118 for Jaurand, G. et al. (1992). "Biologically Active Heparin-like Fragments with a 'Non-Glycosamino' Glycan Structure. Part 1: A Pentasaccharide Containing a 3-O-Methyl Iduronic Acid Unit," *Bioorg. Med. Chem. Lett.* 2(9):897-900.

STN File CA Abstract Accession No. 136:70031 & Love K R et al., "Linear sysntehsis of a protected H-type II pentasaccharide using glycosyl phosphate building blocks", Journal of Organic Chemistry, 2001, pp. 8165-8175, vol. 66, No. 24.

Tamura, J. et al. (1996). "Synthetic Studies of Glycosyl Serines in the Carbohydrate-Protein Region of Protoglycans," *Liebigs Annalen*, pp. 1239-1257.

Van Aelst, S.F. et al. (Nov. 1987). "Synthesis of an Analogue of the Antithrobin Binding Region of Heparin Containing $\alpha$-L-Idopyranose," *Recl. Trav. Chim. Pays-Bas* 106(11):593-595.

Van Boeckel, C.A.A. (1997). "Synthetic Heparin-like Antithrombotics," *Pure & Appl. Chem.* 69(3):389-394.

Van Boeckel, C.A.A. et al. (1985). "Synthesis of a Pentasaccharide Corresponding to the Antithrombin III Binding Fragment of Heparin," *J. Carbohydrate Chemistry* 4(3):293-321.

Van Boeckel, C.A.A. et al. (1988). "Synthesis of a Potent Antithrombin Activating Pentasaccharide: A New Heparin-Like Fragment Containing Two 3-O-Sulphated Glucosamines," *Tetrahedron Letters* 29(7):803-806.

Vos, J.N. et al. (1991). "Synthesis of a 6-O-Phosphorylated Analogue of the Anithrombin III Binding Sequence f Heparin: Replacement of One Essential Sulphate Group by a Phosphate Group Nullifies the Biological Activity," *Bioorg. Med. Chem. Lett.* 1(3):143-146.

Wessel, H.P. et al. (1989). "140. Synthesis of an N-Acetylated Heparin Pentasaccharide and its Anticoagulant Activity in Comparison with the Heparin Pentasaccharide with High Anti-Factor-Xa Activity," *Helv. Chim. Acta* 72:1268-1277.

\* cited by examiner

¹H NMR spectrum of the Bis-Methyl ester of compound P-33

$^1$H NMR spectrum of compound P-40

SYNTHETIC HEPARIN MONOSACCHARIDES

CROSS-REFERENCE TO RELATED APPLICATIONS

This application is a divisional of U.S. patent application Ser. No. 10/488,677 (U.S. Pat. No. 7,541,445), which is a National Phase application under 35 U.S.C. §371 of International Application No. PCT/AU02/01228, filed Sep. 6, 2002, and claims the benefit of Australian Application No. PR 7587, filed Sep. 7, 2001, the disclosures of which are incorporated herein by reference in their entirety.

FIELD OF THE INVENTION

This invention is directed to intermediates, and processes for the chemical synthesis of AT-III binding heparin or heparinoid, pentasaccharides.

BACKGROUND ART

Vascular thrombosis is a cardiovascular disease indicated by the partial or total occlusion of a blood vessel by a clot containing blood cells and fibrin. In arteries, it results predominantly from platelet activation and leads to heart attack, angina or stroke, whereas venous thrombosis results in inflammation and pulmonary emboli. The coagulation of blood is the result of a cascade of events employing various enzymes collectively known as activated blood-coagulation factors. Heparin, a powerful anticoagulant has been used since the late 1930's in the treatment of thrombosis. In its original implementation, tolerance problems were noted and so reduced dosage was suggested to reduce bleeding and improve efficacy. In the early 1970's, clinical trials did indeed indicate acceptable tolerance was obtainable whilst still preserving antithrombotic activity. Unfractioned heparin (UFH) is primarily used as an anticoagulant for both therapeutic and surgical indications, and is usually derived from either bovine lung or porcine mucosa. Amongst the modern uses of unfractioned heparin are the management of unstable angina, an adjunct to chemotherapy and anti-inflammatory treatment, and as a modulation agent for growth factors and treatment of haemodynamic disorders.

In the late 1980's, the development of low molecular weight heparins (LMWHs) led to improvements in antithrombotic therapy. LMWHs are derived from UFH by such processes as; chemical degradation, enzymatic depolymerisation and γ-radiation cleavage. This class of heparins has recently been used for treatment of trauma related thrombosis. Of particular interest is the fact that their relative effects on platelets are minimal compared to heparin, providing an immediate advantage when treating platelet compromised patients. The degree of depolymerisation of UFH can be controlled to obtain LMWH of different lengths. Dosage requirements for the treatment of deep vein thrombosis (DVT) are significantly reduced when employing LMWH as opposed to UFH, although in general the efficacy of both therapeutics seems to be comparable. In addition, LMWH can be effective as an alternative therapeutic for patients who have developed a sensitivity to UFH. Unfortunately, there has recently been a great deal of concern in the use of LMWH due to the perceived potential for cross-species viral contamination as a result of the animal source of the parent UFH.

One way of avoiding the possibility of cross-species contamination, is to prepare heparins by chemical synthesis. This method would also provide the opportunity to develop second generation heparins or heparinoids, that can be tailored to target particular biological events in the blood coagulation cascade.

An investigation to determine the critical structural motif required for an important binding event in a coagulation cascade involving heparin, dates back to the 1970's. Some structural features of heparin were defined, but the binding domains of interest remained essentially undefined. Research conducted by Lindahl and co-workers[1] and separately by Choay and co-workers[2] eventually led to the determination that a pentasaccharide sequence constituted the critical binding domain for the pro-anticoagulant cofactor, antithrombin III (AT-III). After determination of the critical heparin sugar sequence, complete chemical syntheses were embarked upon to further prove the theories. Complete syntheses of the pentasaccharide binding domain were completed at similar times by Sinay and co-workers[3] and by Van Boeckel and co-workers[4].

Significant difficulties were encountered during both these reported syntheses. The synthesis by Van Boeckel and co-workers provided a method on reasonable scale (156 mg's of final product) and with improved yields compared to the Sinay synthesis, but still only provided an overall yield of 0.22%, (compared with 0.053% for the Sinay synthesis). One particular problem encountered during the final deprotection, was the intermolecular reaction of the hemiacetal (the reducing end functionality of the sugar), which led to the formation dimers and trimers. To reduce the likelihood of this occurring, an α-methyl glycoside of the pentasaccharide was synthesised. The structures of interest are represented immediately below, wherein I represents the hemiacetal form, and II represents the α-methylglycoside form.

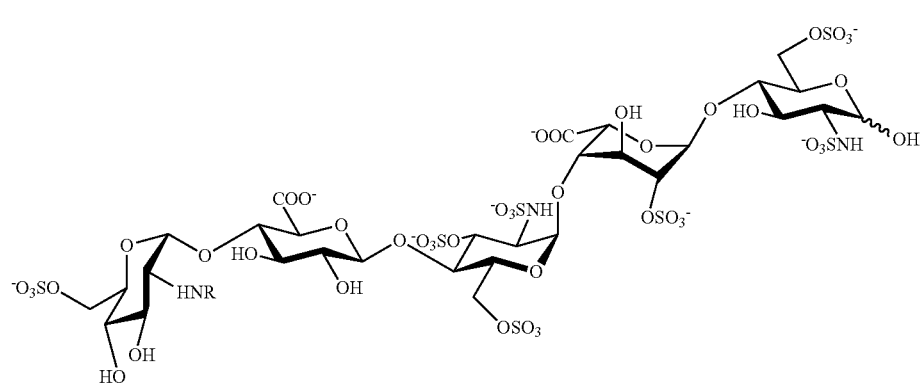

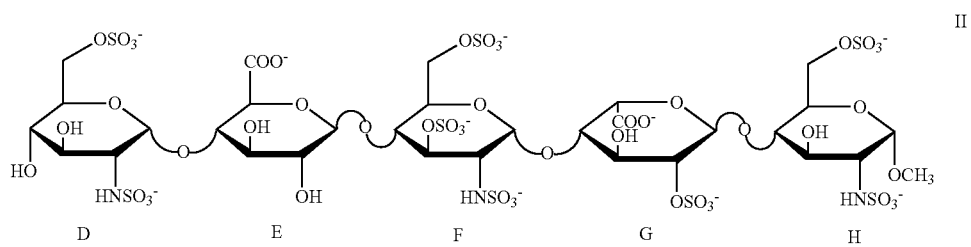

As mentioned, studies have determined that the significant biological event in preventing thrombosis is the binding of a pentasaccharide sequence[5] of heparin, to heparin cofactor antithrombin III (AT-III). As well as pentasaccharide I, the important derivative II has also been prepared by total synthesis[6]. Compound II has recently completed phase III clinical trials for the treatment of deep-vein thrombosis. The following patents display some relevance to the present invention. U.S. Pat. No. 4,401,662 claims composition of matter on the pentasaccharide AT-III binding sequence of heparin as does U.S. Pat. No. 4,496,550. Patents EP 0,084,999 and U.S. Pat. No. 4,818,816 detail synthetic methodologies towards pentasaccharide I, and derivative II.

OBJECT OF THE INVENTION

It is an object of the invention to provide a synthetic preparation for heparin pentasaccharides, and intermediates thereof, and to novel intermediates for heparin pentasaccharides, and to novel heparin pentasaccharides.

The present invention provides composition of matter of intermediates, and a process for the synthesis, of AT-III binding heparins and heparinoids. What this entails is a stepwise synthetic process employing monosaccharide building blocks.

The nature of the AT-III binding pentasaccharide is such, that under cursory analysis of the individual monomeric units constituting the pentasaccharide, we note that each is distinct from the others. Secondly, we can see that there is an alternating stereospecificity in regard to the glycosidic linkages (below).

In a synthesis, the difference evident in each block requires that each individual monomer used in the synthesis will need a different protecting group pattern. In light of this, it is essential in the synthesis of the above pentasaccharide that a protecting group strategy is carefully conceived. As can be seen, the pentasaccharide displays O-sulphation, N-sulphation, there are free hydroxyl groups, and there are stereospecific glycosidic linkages.

Therefore, a protection strategy is required such that (1) sulphation can be effected at the required sites, whilst leaving some hydroxyl groups unsulphated (note that due to the chemical lability of N- and O-sulphates, sulphation needs to be effected late in the synthesis), (2) a protection strategy is required that assists in effecting the appropriate glycosidic linkage and (3) a protection strategy is required that enables the correct (in terms of regio- and stereoisomerism) glycosidic linkages to be formed. α-Glycosidic linkages are typically generated by the use of what are known as non-participating protecting groups, whilst β-linkages are effected by participating protecting groups. Some N- and O-participating and non-participating protecting groups are known to the art (the art being considered carbohydrate chemistry). It is also well known to the art that the kind of protecting groups employed can effect the reactivity of the building block. The culmination of these requirements are demonstrated in the exemplary building block C below, which displays the kind of characteristics required to effect the synthesis of heparin oligosaccharides.

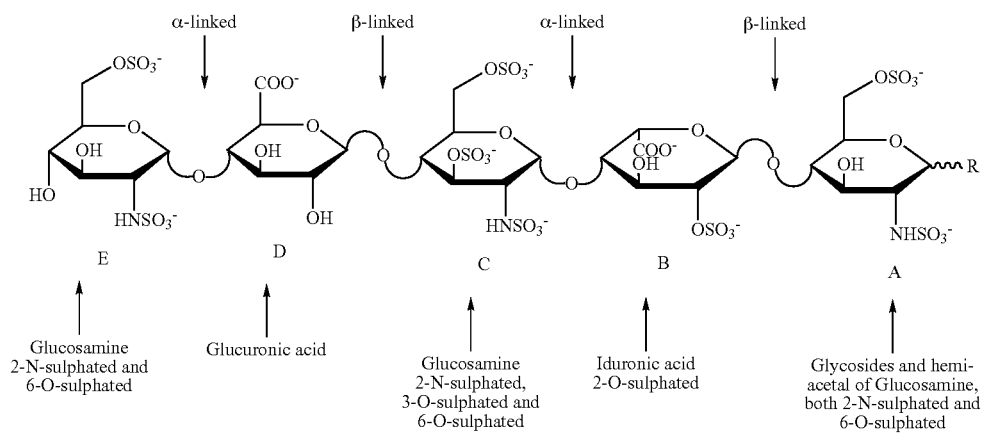

Exemplary Building Block C

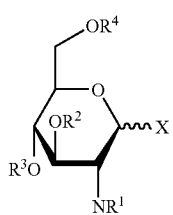

In exemplary building block C, X is a leaving group suitable of reacting with another monomer or acceptor, to form an interglycosidic linkage; $R^1$ is a non-participating amino protecting group so as to effect an α-linkage upon activation of X followed by coupling to an appropriate acceptor; $R^2$ and $R^4$ can be similarly protected to allow for eventual O-sulphation, whilst $R^3$ is required to be differentially protected so as to allow the formation of an acceptor hydroxyl group to couple this block to the next in the chain. The building blocks shown immediately below exemplify the kind of derivatised monosaccharides required to effect the synthesis of heparin AT-III binding pentasaccharides.

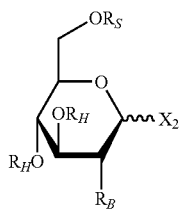

E

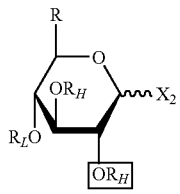

D

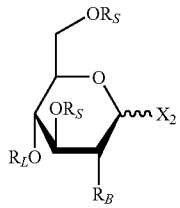

C

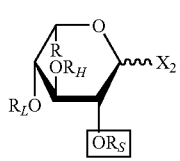

B

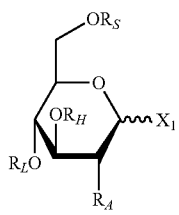

A

The protecting groups represented by '$R_S$' shown above are sites that will eventually require O-sulphation, the protecting groups represented by '$R_H$' need to be orthogonal to '$R_S$' and represents sites that will eventually become hydroxyl groups. The substituents '$X_1$' and '$X_2$' represent leaving groups that are activated to react with another suitable protected building block to form a glycosidic linkage, and, in the case of $X_1$, may also be derivatised as alkyl glycosides or substituted with a group suitable to allow conjugation to a support for drug delivery. The '$R_L$' groups are protecting groups orthogonal to both '$R_S$' and '$R_H$', and represent sites through which chain elongation via glycosylation occurs. 'R' is representative of either a protected or latent carboxylate function. The '$R_A$' groups are non-participating amino protecting groups that enable α-linkages to be formed while the '$R_B$' groups may be either a participating or non-participating amino protecting group. There is another level of complexity to be added to the synthesis in as much as the protecting groups in blocks D and B that are indicated by the boxes, need to be such that they allow for the formation of a β-glycosidic linkage. This may require a two stage protection at the indicated sites, i.e., a protection followed by deprotection and subsequent reprotection with a different protecting group. The initial protection is required to effect the correct stereochemistry in a glycosylation, and second stage protection to allow for the correct sulphation pattern.

As is evident, the pentasaccharide can be constructed in a variety of different ways; blocks B and A can be coupled, blocks E and D can be coupled, block C can be coupled to either, and the resulting dimer and trimer can finally be coupled to form the pentasaccharide. Alternatively, each block can be added sequentially and so on. There are a number of alternative coupling sequences that can be easily conceived and the choice made in regard to this, in itself, has a marked effect on the synthetic methodologies that will finally be employed, and therefore impacts on the overall success of the synthesis.

In one aspect the invention provides for a monosaccharide building block in the D-glucopyrano configuration, for the preparation of synthetic heparinoids, said building block of General Formula I,

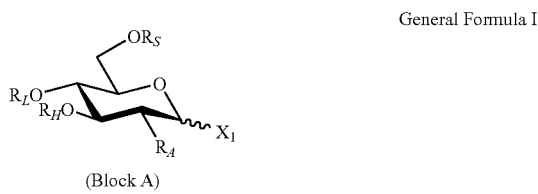

General Formula I (Block A)

wherein, $X_1$ includes but is not limited to: hydroxy, alkoxy, aryloxy, benzyloxy, substituted benzyloxy; thioalkyl, thioaryl, halogen, trichloroacetimidoyl, phosphate and related phosphate ester type leaving groups, or other suitable leaving group; a 'butyldiphenylsilyloxy or other such substituted silyloxy protecting group; a lipoaminoacid or other such group suitable for conjugation to delivery systems or solid supports; and the stereochemistry may be alpha or beta; other suitable groups will be known to those skilled in the art, $R_A$ includes but is not limited to: an azido function, an amine; an NH-Dde, NH-DTPM, NH-Fmoc, NH-Boc, NH-Cbz, NH-Troc, N-phthalimido; or, other such suitable protected amino functions known to those skilled in the art, $R_H$ is a benzyl or, substituted benzyl protecting group, allyl, allyloxycarbonyl, or $R_{H1}$ and $R_A$ can combine together to form a cyclic carbamate; $R_L$ includes but is not limited to: a H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene)ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups allyloxycarbonyl, allyl ether, carbonate type protecting groups; or $R_L$ and $R_{S1}$ can combine to form a benzylidene or substituted benzylidene ring; or, other such suitable protecting groups as known to those skilled in the art, and $R_S$ includes but is not limited to: 4-methoxyphenyl; substituted benzyl groups; alkylacyl, arylacyl or alkylarylacyl, and substituted alkylacyl, arylacyl or alkylarylacyl protecting groups; carbonate protecting groups, a $^t$butyldiphenylsilyloxy or other such substituted silyloxy protecting group, allyl, methoxymethyl, methoxyethyl, benzyloxymethyl; or, other suitable protecting groups as known to those skilled in the art.

Alternatively $R_L$ and $R_S$ can combine to form a benzylidene or substituted benzylidene ring.

In a second aspect the invention provides for a monosaccharide building block in the L-idopyrano conformation, for the preparation of synthetic heparinoids, said building block of General Formula II,

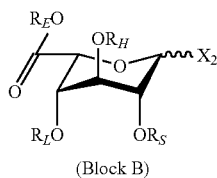

General Formula II (Block B)

wherein, $X_2$ includes but is not limited to: a hydroxyl group; thioalkyl, thioaryl, halogen, trichloroacetimidoyl, phosphate and related phosphate ester type leaving groups, or other suitable leaving group; a $^t$butyldiphenylsilyloxy or other such substituted silyloxy protecting group; and the stereochemistry may be alpha or beta; other suitable groups will be known to those skilled in the art, $R_S$ is defined as in General Formula I,
$R_H$ is defined as in General Formula I,
$R_L$ is defined as in General Formula I, and
$R_E$ includes but is not limited to: methyl, $C_2$-$C_5$ alkyl; substituted alkyl; or, benzyl and substituted benzyl groups; other suitable groups will be known to those skilled in the art. Or, $R_H$ is selected from the group consisting of benzyl or substituted benzyl protecting group, allyl, allyloxycarbonyl;

$R_S$ is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group allyl, methoxymethyl, methoxyethyl, benzyloxymethyl;

$R_E$ is selected from the group consisting of methyl, $C_2$-$C_5$ alkyl; substituted alkyl, $C_3$-$C_5$ alkenyl; or, benzyl and substituted benzyl groups;

$R_L$ is selected from a H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene)ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups; allyloxycarbonyl, allyl ether, carbonate type protecting groups;

$X_2$ is selected from a hydroxyl group, thioalkyl, thioaryl, halogen, imidoyl, phosphate and related phosphate ester type leaving groups, a $^t$butyldiphenylsilyloxy or other such substituted silyloxy protecting group; and the stereochemistry may be alpha or beta.

In a third aspect the invention provides for a monosaccharide building block in the L-idopyrano configuration, for the preparation of synthetic heparinoids, said building block of General Formula III,

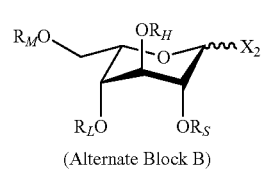

General Formula III (Alternate Block B)

wherein, $X_2$ is defined as in General Formula II,
$R_S$ is defined as in General Formula II,
$R_H$ is defined as in General Formula I,
$R_L$ is defined as in General Formula I, and
$R_M$ includes but is not limited to a p-methoxyphenyl protecting group or other suitable oxidatively labile protecting group; a trityl group; or, other such suitable protecting groups as known to those skilled in the art.

In a fourth aspect the invention provides for a monosaccharide building block in the D-glucopyrano configuration for the preparation of synthetic heparinoids, said building block of General Formula IV,

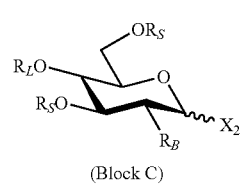

General Formula IV (Block C)

wherein, $X_2$ is defined as in General Formula II,
$R_B$ includes but is not limited to: an azido function, an amine; an NH-Dde or NH-DTPM group; or other suitably protected amino functions as known to those skilled in the art, or $R_S$ (adjacent $R_B$) and $R_B$ can combine together to form a cyclic carbamate;

$R_S$ (adjacent $R_B$) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ′butyldiphenylsilyloxy or other such substituted silyloxy protecting group allyl, methoxymethyl, methoxyethyl, benzyloxymethyl, or $R_{S4}$ and $R_B$ may be combined to form a cyclic carbamate;

$R_S$ (adjacent the oxygen) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ′butyldiphenylsilyloxy or other such substituted silyloxy protecting group, allyl, methoxymethyl, methoxyethyl, benzyloxymethyl.

In a fifth aspect the invention provides for a monosaccharide building block in the D-glucuronate configuration for the preparation of synthetic heparinoids, said building block of General Formula V,

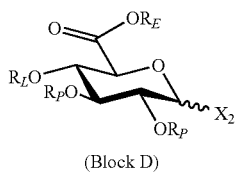

General Formula V (Block D)

wherein, $X_2$ is as defined in General Formula II, $R_P$ includes but is not limited to: 4-methoxyphenyl; substituted benzyl groups; alkylacyl, arylacyl and alkylarylacyl, or substituted alkylacyl, arylacyl and alkylarylacyl protecting groups; carbonate protecting groups; or, other suitable protecting groups as known to those skilled in the art.

$R_L$ is defined as in General Formula I, and
$R_E$ is defined as in General Formula II.

In a sixth aspect the invention provides for a monosaccharide building block in the D-glucopyrano configuration for the preparation of synthetic heparinoids, said building block of General Formula VI,

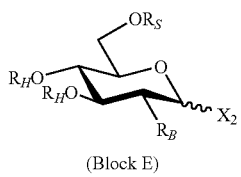

General Formula VI (Block E)

wherein, $X_2$ is as defined as in General Formula II,
$R_B$ is defined as in General Formula IV,
$R_H$ may be selected independently and are defined as in General Formula I, and
$R_S$ is defined as in General Formula I, or, wherein
$R_H$ (adjacent the ORs moiety) is selected from the group consisting of benzyl or substituted benzyl protecting group, allyl, allyloxycarbonyl;
$R_H$ (adjacent the Rb moiety) is selected from the group consisting of benzyl or substituted benzyl protecting group, allyl, allyloxycarbonyl, or this $R_H$ and $R_B$ independently can combine together to form a cyclic carbamate;
$R_S$ is selected from the group consisting of 4-methoxyphenyl; substituted benzyl groups; alkylacyl, arylacyl or alkylarylacyl; and substituted alkylacyl, arylacyl or alkylarylacyl protecting groups; carbonate protecting groups; a ′butyldiphenylsilyloxy or other such substituted silyloxy protecting group allyl, methoxymethyl, methoxyethyl, benzyloxymethyl, or $R_{S5}$ and $R_H$ can be combined to form a cyclic acetal or ketal moiety;

$R_B$ is selected from the group consisting of an azido function, an amine; an NH-Dde or NH-DTPM group, or $R_H$ (adjacent the $R_B$) and $R_B$ can combine together to form a cyclic carbamate;

$X_2$ is selected from a hydroxyl group; thioalkyl, thioaryl, halogen, trichloroacetimidoyl, phosphate and related phosphate ester type leaving groups, a ′butyldiphenylsilyloxy or other such substituted silyloxy protecting group; and the stereochemistry may be alpha or beta.

In a seventh aspect the invention provides for a monosaccharide building block in the D-glucopyrano configuration for the preparation of synthetic heparinoids, said building block of General Formula VII,

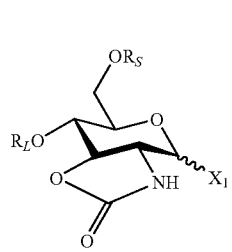

General Formula VII (Common Intermediate for Blocks A, C and E)

wherein, $X_1$ is defined as in General Formula I, $R_L$ is defined as in General Formula I, and $R_S$ is defined as in General Formula I. $R_L$ and $R_S$ may also together combine to form a benzylidene or substituted benzylidene ring, or $X_1$ is selected from the group consisting of hydroxy, alkoxy, aryloxy, benzyloxy, substituted benzyloxy, thioalkyl, thioaryl, halogen, trichloroacetimidoyl, phosphate and related phosphate ester type leaving groups, a ′butyldiphenylsilyloxy or other such substituted silyloxy protecting group; a lipoaminoacid or other such group suitable for conjugation to delivery systems or solid supports; and the stereochemistry may be alpha or beta;

$R_L$ is selected from an H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene)ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups; allyloxycarbonyl, allyl ether, and carbonate type protecting groups;

$R_S$ is selected from the group consisting of 4-methoxyphenyl, 4-methoxybenzyl; substituted benzyl groups; alkylacyl, arylacyl or alkylarylacyl, and substituted alkylacyl, arylacyl or alkylarylacyl protecting groups; carbonate protecting groups; and tert-Butyldiphenylsilyl;

$R_L$ and $R_S$ may also together combine to form an alkylidene, isopropylidene, benzylidene or substituted benzylidene ring.

In an eighth aspect the invention provides for a disaccharide building block for the preparation of synthetic heparinoids, said building block of General Formula VIII, General Formula VIII

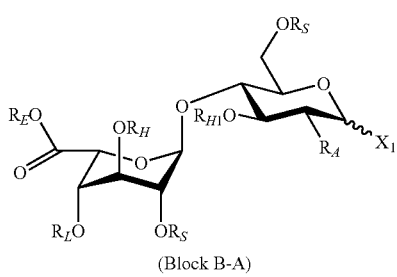

(Block B-A)

wherein, $X_1$ is defined as in General Formula I,
$R_{H1}$ is defined as being selected from $R_H$ of General Formula I, with the addition that $R_{H1}$ and $R_A$ can combine together to form a cyclic carbamate,
$R_A$ is defined as in General Formula I, with the addition that $R_{H1}$ and $R_A$ can combine together to form a cyclic carbamate
$R_S$ is defined as in General Formula I,
$R_H$ is defined as in General Formula I,
$R_L$ is defined as in General Formula I, and
$R_E$ is defined as in General Formula II, or
$X_1$ is selected from the group consisting of hydroxy, alkenyloxy, alkoxy, aryloxy, benzyloxy, substituted benzyloxy, thioalkyl, thioaryl, halogen, imidoyl, phosphate and related phosphate ester type leaving groups, a ′butyldiphenylsilyloxy or other such substituted silyloxy protecting group; a lipoaminoacid or other such group suitable for conjugation to delivery systems or solid supports; and the stereochemistry may be alpha or beta;
$R_H$ is selected from the group consisting of benzyl or substituted benzyl protecting group, allyl, allyloxycarbonyl;
$R_{H1}$ is selected from the group consisting of benzyl or substituted benzyl protecting group, allyl, allyloxycarbonyl, or $R_{H1}$ and $R_A$ can combine together to form a cyclic carbamate;
$R_A$ is selected from the group consisting of an azido function, an amine; an NH-Dde, NH-DTPM, NH-Fmoc, NH-Boc, NH-Troc, N-phthalimido, NH—Ac, NH-allyloxycarbonyl; or $R_H$, and $R_A$ can combine together to form a cyclic carbamate;
$R_S$ (on block A) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ′butyldiphenylsilyloxy or other such substituted silyloxy protecting group; allyl, methoxymethyl, methoxyethyl, benzyloxymethyl or benzoyl;
$R_S$ (on block B) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ′butyldiphenylsilyloxy or other such substituted silyloxy protecting group; allyl, methoxymethyl, methoxyethyl, benzyloxymethyl;
$R_E$ is selected from the group consisting of methyl, $C_2$-$C_5$ alkyl; substituted alkyl, $C_3$-$C_5$ alkenyl; or, benzyl and substituted benzyl groups;
$R_L$ is selected from an H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene) ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups; allyloxycarbonyl, allyl ether, and carbonate type protecting groups.

In a ninth aspect the invention provides for a disaccharide building block for the preparation of synthetic heparinoids, said building block of General Formula IX, General Formula IX

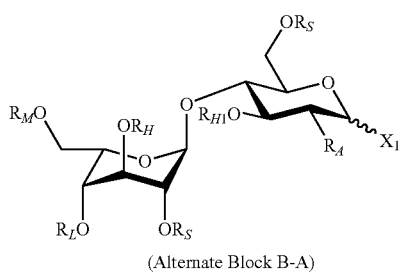

(Alternate Block B-A)

wherein, $X_1$ is as defined as in General Formula I,
$R_A$ is defined as in General Formula XIII,
$R_{H1}$ is defined as in General Formula XIII,
$R_S$ is defined as in General Formula I,
$R_L$ is defined as in General Formula I, and
$R_M$ is defined as in General Formula III, or, alternatively,
$X_1$ is selected from the group consisting of hydroxy, alkenyloxy, alkoxy, aryloxy, benzyloxy, substituted benzyloxy; thioalkyl, thioaryl, halogen, imidoyl, phosphate and related phosphate ester type leaving groups, a ′butyldiphenylsilyloxy or other such substituted silyloxy protecting group; a lipoaminoacid or other such group suitable for conjugation to delivery systems or solid supports; and the stereochemistry may be alpha or beta;
$R_A$ is selected from the group consisting of an azido function, an amine; an NH-Dde, NH-DTPM, NH-Fmoc, NH-Boc, NH-Troc, N-phthalimido, NH—Ac, NH-Allyloxycarbonyl; or $R_{H1}$ and $R_A$ can combine together to form a cyclic carbamate;
$R_S$ (on block A) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ′butyldiphenylsilyloxy or other such substituted silyloxy protecting group; allyl, methoxymethyl, methoxyethyl, and benzyloxymethyl;
$R_S$ (on block B) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ′butyldiphenylsilyloxy or other such substituted silyloxy protecting group; allyl, methoxymethyl, methoxyethyl, and benzyloxymethyl;
$R_H$ is selected from the group consisting of benzyl or substituted benzyl protecting group, allyl, and allyloxycarbonyl;
$R_{H1}$ is selected from the group consisting of benzyl or substituted benzyl protecting group, allyl, and allyloxycarbonyl, or $R_{H1}$ and $R_A$ can combine together to form a cyclic carbamate;
$R_M$ is selected from a p-methoxyphenyl or p-methoxybenzyl protecting group or other suitable oxidatively labile protecting group; and a trityl group;
or $R_M$ and $R_L$ are combined together to form an isopropylidene, benzylidene, substituted benzylidene, cyclohexylidene or other acetal or ketal protecting group; or
$R_L$ is selected from an H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene)ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups; allyloxycarbonyl, allyl ether, and carbonate type protecting groups.

In a tenth aspect the invention provides for a disaccharide building block for the preparation of synthetic heparinoids, said building block of General Formula X,

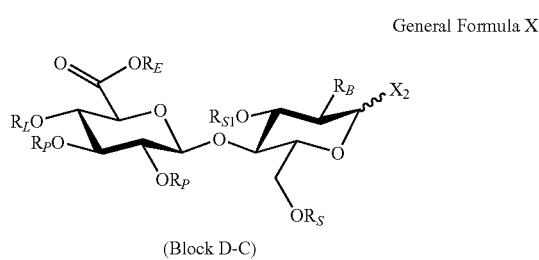

General Formula X (Block D-C)

wherein, $X_2$ is as defined in General Formula II, $R_{S1}$ is defined as being selected from $R_S$ of General Formula I, with the addition that $R_{S1}$ and $R_B$ can combine together to form a cyclic carbamate.

$R_B$ is defined as in General Formula IV, with the addition that $R_{S1}$ and $R_B$ can combine together to form a cyclic carbamate.

$R_S$ is defined as in General Formula I, $R_P$ are defined as in General Formula V, $R_L$ is defined as in General Formula I, and $R_E$ is defined as in General Formula II, or $X_2$ is selected from the group consisting of hydroxy, alkenyloxy, alkoxy, aryloxy, benzyloxy, substituted benzyloxy; thioalkyl, thioaryl, halogen, imidoyl, phosphate and related phosphate ester type leaving groups, a 'butyldiphenylsilyloxy or other such substituted silyloxy protecting group; a lipoaminoacid or other such group suitable for conjugation to delivery systems or solid supports; and the stereochemistry may be alpha or beta;

$R_S$ is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a 'butyldiphenylsilyloxy or other such substituted silyloxy protecting group allyl, methoxymethyl, methoxyethyl, and benzyloxymethyl;

$R_{S1}$ is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a 'butyldiphenylsilyloxy or other such substituted silyloxy protecting group allyl, methoxymethyl, methoxyethyl, and benzyloxymethyl, or $R_{S1}$ and $R_B$ may be combined to form a cyclic carbamate;

$R_E$ is selected from the group consisting of methyl, $C_2$-$C_5$ alkyl; substituted alkyl, $C_3$-$C_5$ alkenyl; or, benzyl and substituted benzyl groups;

$R_B$ is selected from the group consisting of an azido function, an NH-Dde or NH-DTPM group, or $R_{S4}$ and $R_B$ can combine together to form a cyclic carbamate;

$R_P$ (adjacent O—$R_L$) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; and carbonate protecting groups;

$R_P$ (adjacent the link to block C) is selected from the group consisting of hydroxy, 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, and $C_3$-$C_5$ alkenyl;

$R_L$ is selected from an H atom; a levulinoyl, chloroacetyl, 4-acetoxybenzoyl, 4-acetamidobenzoyl, 4-azidobenzoyl, or other substituted benzoyl type protecting group; a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene)ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups; allyloxycarbonyl, allyl ether, and carbonate type protecting groups.

In an eleventh aspect the invention provides for a disaccharide building block for the preparation of synthetic heparinoids, said building block of General Formula XI,

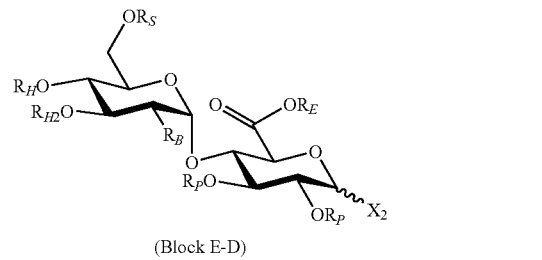

General Formula XI (Block E-D)

wherein, $X_2$ is as defined in General Formula II, $R_P$ are defined as in General Formula V, $R_E$ is defined as in General Formula II, $R_B$ is defined as in General Formula IV, with the addition that $R_B$ and $R_{H2}$ can combine to form a cyclic carbamate, $R_{H2}$ is defined as being selected from $R_H$ of General Formula I, with the addition that $R_B$ and $R_{H2}$ can combine to form a cyclic carbamate, $R_H$ is defined as in General Formula I, and $R_S$ is defined as in General Formula I, or $X_2$ is selected from a hydroxyl group; thioalkyl, thioaryl, halogen, trichloroacetimidoyl, phosphate and related phosphate ester type leaving groups, a 'butyldiphenylsilyloxy or other such substituted silyloxy protecting group; and the stereochemistry may be alpha or beta;

$R_P$ (adjacent the O link) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; carbonate protecting groups;

$R_P$ (adjacent $X_2$) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, and $C_3$-$C_5$ alkenyl;

$R_E$ is selected from the group consisting of methyl, $C_2$-$C_5$ alkyl; substituted alkyl, $C_3$-$C_5$ alkenyl; or, benzyl and substituted benzyl groups;

$R_B$ is selected from the group consisting of an azido function, an amine; an NH-Dde or NH-DTPM group, or $R_{H2}$ and $R_{B1}$ can combine together to form a cyclic carbamate;

$R_H$ is selected from the group consisting of benzyl or substituted benzyl protecting group, allyl, and allyloxycarbonyl;

$R_{H2}$ is selected from the group consisting of benzyl or substituted benzyl protecting group, allyl, allyloxycarbonyl, or $R_{H2}$ and $R_{B1}$ independently can combine together to form a cyclic carbamate;

$R_S$ is selected from the group consisting of 4-methoxyphenyl; 4-methoxybenzyl, substituted benzyl groups; alkylacyl, benzoyl arylacyl or alkylarylacyl, and substituted alkylacyl, 4-chlorobenzoyl, arylacyl or alkylarylacyl protecting groups; allyloxycarbonyl, ethoxycarbonyl, tertbutoxycarbonyl, carbonate protecting groups; a 'butyldiphenylsilyloxy or other such substituted silyloxy protecting group; allyl, methoxymethyl, methoxyethyl, and benzyloxymethyl; or $R_S$ and $R_H$ can be combined to form a cyclic acetal or ketal moiety.

In a twelfth aspect the invention provides for a disaccharide building block for the preparation of synthetic heparinoids, said building block of General Formula XII,

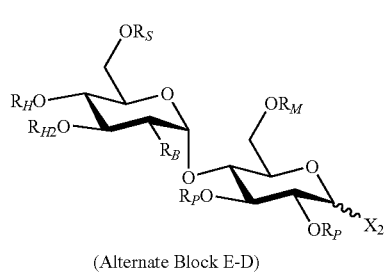

General Formula XII (Alternate Block E-D)

wherein, $X_2$ is as defined in General Formula II,
$R_P$ are defined as in General Formula V,
$R_M$ is defined as in General Formula III,
$R_B$ and $R_{H2}$ are as defined in General Formula XI,
$R_H$ is defined as in General Formula I, and
$R_S$ is defined as in General Formula I, or
$X_2$ is selected from a hydroxyl group; thioalkyl, thioaryl, halogen, trichloroacetimidoyl, phosphate and related phosphate ester type leaving groups, a 'butyldiphenylsilyloxy or other such substituted silyloxy protecting group; and the stereochemistry may be alpha or beta;

$R_P$ (adjacent the O linking group) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; and carbonate protecting groups;

$R_P$ (adjacent $X_2$) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, and $C_3$-$C_5$ alkenyl;

$R_B$ is selected from the group consisting of an azido function, an amine; an NH-Dde or NH-DTPM group, or $R_{H2}$ and $R_{B1}$ can combine together to form a cyclic carbamate;

$R_H$ is selected from the group consisting of benzyl or substituted benzyl protecting group, allyl, and allyloxycarbonyl;

$R_{H2}$ is selected from the group consisting of benzyl or substituted benzyl protecting group, allyl, allyloxycarbonyl, or $R_{H2}$ and $R_{B1}$ independently can combine together to form a cyclic carbamate;

$R_S$ is selected from the group consisting of 4-methoxyphenyl; 4-methoxybenzyl, substituted benzyl groups; alkylacyl, benzoyl, arylacyl or alkylarylacyl, and substituted alkylacyl, 4-chlorobenzoyl, arylacyl or alkylarylacyl protecting groups; allyloxycarbonyl, ethoxycarbonyl, tertbutoxycarbonyl, carbonate protecting groups; or is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a 'butyldiphenylsilyloxy or other such substituted silyloxy protecting group allyl, methoxymethyl, methoxyethyl, and benzyloxymethyl;

or $R_S$ and $R_H$ can be combined to form a cyclic acetal or ketal moiety;

$R_M$ is selected from the group consisting of a p-methoxyphenyl protecting group or other suitable oxidatively labile protecting group; a trityl group.

In a thirteenth aspect the invention provides for a disaccharide building block for the preparation of synthetic heparinoids, said building block of General Formula XIII,

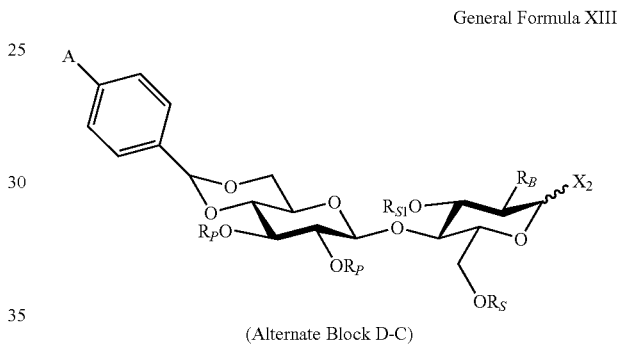

General Formula XIII (Alternate Block D-C)

wherein, $X_2$ is defined as in General Formula II,
$R_B$ and $R_{S1}$ are defined as in General Formula X,
$R_S$ is defined as in General Formula I,
$R_P$ is defined as in General Formula V, and
A includes but is not limited to; H, methoxy, methyl; other suitable substituents will be known to those in the art, or
$X_2$ is selected from a hydroxyl group; thioalkyl, thioaryl, halogen, imidoyl, phosphate and related phosphate ester type leaving groups, a 'butyldiphenylsilyloxy or other such substituted silyloxy protecting group; and the stereochemistry may be alpha or beta;

$R_B$ is selected from the group consisting of an azido function, an amine; an NH-Dde or NH-DTPM group, or $R_{S4}$ and $R_B$ can combine together to form a cyclic carbamate;

$R_S$ is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a 'butyldiphenylsilyloxy or other such substituted silyloxy protecting group allyl, methoxymethyl, methoxyethyl, and benzyloxymethyl;

$R_{S1}$ is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a 'butyldiphenylsilyloxy or other such substituted silyloxy protecting group allyl, methoxymethyl, methoxyethyl, and benzyloxymethyl;

or $R_{S4}$ and $R_B$ may be combined to form a cyclic carbamate;

$R_P$ (adjacent the O linking atom to the benzyl) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; and carbonate protecting groups;

$R_P$ (adjacent the O linking atom to C) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, and $C_3$-$C_5$ alkenyl; and A includes but is not limited to; H, methoxy, methyl; other suitable substituents will be known to those in the art.

In a fourteenth aspect the invention provides for a trisaccharide building block for the preparation of synthetic heparinoids, said building block of General Formula XIV,

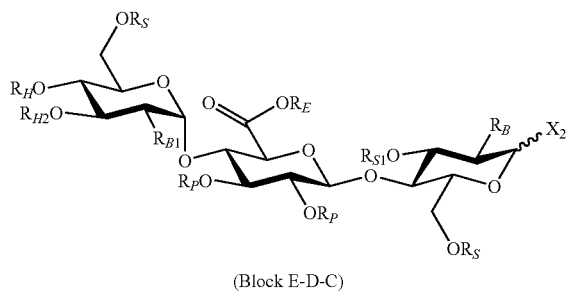

General Formula XIV (Block E-D-C)

wherein, $X_2$ is defined as in General Formula II,
$R_B$ and $R_{S1}$ are defined as in General Formula X,
$R_S$ is defined as in General Formula I,
$R_P$ is defined as in General Formula V,
$R_E$ is defined as in General Formula II,
$R_{B1}$ is defined as being selected from $R_B$ of General Formula IV, with the addition that $R_{B1}$ can combine together with $R_{H2}$ to form a cyclic carbamate,
$R_{H2}$ is defined as being selected from $R_H$ of General Formula I, with the addition that $R_{H2}$ can combine together with $R_{B1}$ to form a cyclic carbamate, and
$R_H$ is defined as in General Formula I or
$X_2$ is selected from a hydroxyl group; thioalkyl, thioaryl, halogen, trichloroacetimidoyl, phosphate and related phosphate ester type leaving groups, a $^t$butyldiphenylsilyloxy or other such substituted silyloxy protecting group; and the stereochemistry may be alpha or beta;
$R_P$ (adjacent block E) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; and carbonate protecting groups;
$R_P$ (adjacent Block C) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, and $C_3$-$C_5$ alkenyl;
$R_E$ is selected from the group consisting of methyl, $C_2$-$C_5$ alkyl; substituted alkyl, $C_3$-$C_5$ alkenyl; or, benzyl and substituted benzyl groups;
$R_{B1}$ is selected from the group consisting of an azido function, an amine; an NH-Dde or NH-DTPM group, or $R_{H2}$ and $R_{B1}$ can combine together to form a cyclic carbamate;

$R_H$ is selected from the group consisting of benzyl or substituted benzyl protecting group, allyl, and allyloxycarbonyl;
$R_{H2}$ is selected from the group consisting of benzyl or substituted benzyl protecting group, allyl, and allyloxycarbonyl, or $R_{H2}$ and $R_{B1}$ independently can combine together to form a cyclic carbamate;
$R_S$ (on block E) is selected from the group consisting of 4-methoxyphenyl; 4-methoxybenzyl, substituted benzyl groups; alkylacyl, benzoyl, arylacyl or alkylarylacyl, and substituted alkylacyl, 4-chlorobenzoyl, arylacyl or alkylarylacyl protecting groups; allyloxycarbonyl, ethoxycarbonyl, tertbutoxycarbonyl, carbonate protecting groups; or is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group allyl, methoxymethyl, methoxyethyl, and benzyloxymethyl;
or $R_S$ and $R_H$ can be combined to form a cyclic acetal or ketal moiety;
$R_S$ (on block C and adjacent the ring O) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group allyl, methoxymethyl, methoxyethyl, and benzyloxymethyl;
$R_S$ (on block C and adjacent the O linking atom) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group allyl, methoxymethyl, methoxyethyl, and benzyloxymethyl;
or $R_S$ and $R_B$ may be combined to form a cyclic carbamate;
$R_B$ is selected from the group consisting of an azido function, an amine; an NH-Dde or NH-DTPM group, or $R_{S4}$ and $R_B$ can combine together to form a cyclic carbamate.

In a fifteenth aspect the invention provides for a trisaccharide building block for the preparation of synthetic heparinoids, said building block of General Formula XV,

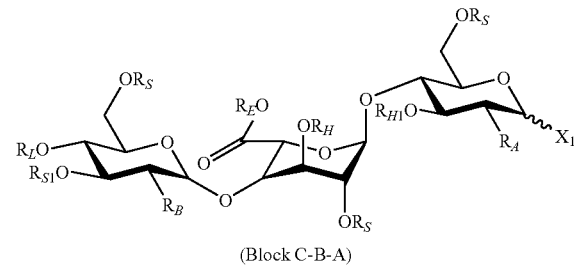

General Formula XV (Block C-B-A)

wherein, $X_1$ is defined as in General Formula I
$R_A$ and $R_{H1}$ are defined as in General Formula VIII,
$R_S$ is defined as in General Formula I,
$R_H$ is defined as in General Formula I,
$R_E$ is defined as in General Formula II,
$R_B$ and $R_{S1}$ are defined as in General Formula X, and
$R_L$ is defined as in General Formula I, or
$X_1$ is selected from the group consisting of hydroxy, alkenyloxy, alkoxy, aryloxy, benzyloxy, substituted benzyloxy; thioalkyl, thioaryl, halogen, imidoyl, phosphate and related phosphate ester type leaving groups, a $^t$butyldiphenylsilyloxy or other such substituted silyloxy protecting group; a lipoaminoacid or other such group suitable for conjugation to delivery systems or solid supports; and the stereochemistry may be alpha or beta;

$R_H$ is selected from the group consisting of benzyl or substituted benzyl protecting group, allyl, and allyloxycarbonyl;

$R_{H1}$ is selected from the group consisting of benzyl or substituted benzyl protecting group, allyl, and allyloxycarbonyl;

$R_A$ is selected from the group consisting of an azido function, an amine; an NH-Dde, NH-DTPM, NH-Fmoc, NH-Boc, NH-Cbz, NH-Troc, N-phthalimido, NH—Ac, NH-Allyloxycarbonyl; or $R_H$ and $R_A$ can combine together to form a cyclic carbamate;

other substituted benzoyl type protecting group; a benzyl group, a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene)ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups; allyloxycarbonyl, allyl ether, and carbonate type protecting groups.

In a sixteenth aspect the invention provides for a tetrasaccharide building block for the preparation of synthetic heparinoids, said building block of General Formula XVI,

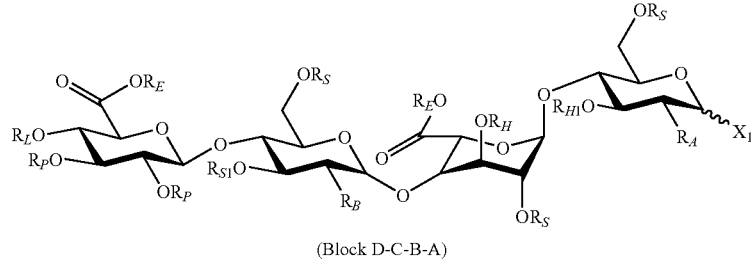

General Formula XVI (Block D-C-B-A)

$R_S$ (on block A) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ⁿbutyldiphenylsilyloxy or other such substituted silyloxy protecting group; allyl, methoxymethyl, methoxyethyl, and benzyloxymethyl;

$R_S$ (on block B) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ⁿbutyldiphenylsilyloxy or other such substituted silyloxy protecting group; allyl, methoxymethyl, methoxyethyl, and benzyloxymethyl;

$R_S$ (on block C) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ⁿbutyldiphenylsilyloxy or other such substituted silyloxy protecting group allyl, methoxymethyl, methoxyethyl, and benzyloxymethyl;

$R_{S4}$ is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ⁿbutyldiphenylsilyloxy or other such substituted silyloxy protecting group; allyl, methoxymethyl, methoxyethyl, and benzyloxymethyl, or $R_{S4}$ and $R_B$ may be combined to form a cyclic carbamate;

$R_E$ is selected from the group consisting of methyl, $C_2$-$C_5$ alkyl; substituted alkyl, $C_3$-$C_5$ alkenyl; or, benzyl and substituted benzyl groups;

$R_B$ is selected from the group consisting of an azido function, an amine; an NH-Dde or NH-DTPM group, or $R_{S4}$ and $R_B$ can combine together to form a cyclic carbamate;

$R_L$ is selected from an H atom; a levulinoyl, chloroacetyl, 4-acetoxybenzoyl, 4-acetamidobenzoyl, 4-azidobenzoyl, or wherein, $X_1$ is defined as in General Formula I $R_A$ and $R_{H1}$ are defined as in General Formula VIII, $R_S$ is defined as in General Formula I, $R_H$ is defined as in General Formula I, $R_E$ is defined as in General Formula II, $R_B$ and $R_{S1}$ are defined as in General Formula X, $R_P$ is as defined in General Formula V, and $R_L$ is as defined in General Formula I, or $X_1$ is selected from the group consisting of hydroxy, alkenyloxy, alkoxy, aryloxy, benzyloxy, substituted benzyloxy; thioalkyl, thioaryl, halogen, imidoyl, phosphate and related phosphate ester type leaving groups, a ⁿbutyldiphenylsilyloxy or other such substituted silyloxy protecting group; a lipoaminoacid or other such group suitable for conjugation to delivery systems or solid supports; and the stereochemistry may be alpha or beta, $R_H$ is selected from the group consisting of benzyl or substituted benzyl protecting group, allyl, and allyloxycarbonyl;

$R_{H1}$ is selected from the group consisting of benzyl or substituted benzyl protecting group, allyl, allyloxycarbonyl, or $R_{H1}$ and $R_A$ can combine together to form a cyclic carbamate;

$R_A$ is selected from the group consisting of an azido function, an amine; an NH-Dde, NH-DTPM, NH-Fmoc, NH-Boc, NH-Cbz, NH-Troc, N-phthalimido, NH—Ac, NH-Allyloxycarbonyl; or $R_{H1}$ and $R_A$ can combine together to form a cyclic carbamate, $R_S$ (on block A) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ⁿbutyldiphenylsilyloxy or other such substituted silyloxy protecting group; allyl, methoxymethyl, methoxyethyl, and benzyloxymethyl;

$R_S$ (on block B) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a ⁿbutyldiphenylsilyloxy or other such substituted silyloxy protecting group; allyl, methoxymethyl, methoxyethyl, and benzyloxymethyl;

$R_S$ (on block C and adjacent the ring oxygen) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group; allyl, methoxymethyl, and methoxyethyl, benzyloxymethyl;

$R_S$ (on block C and adjacent the linking O) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group; allyl, methoxymethyl, methoxyethyl, and benzyloxymethyl, or $R_{S4}$ and $R_B$ may be combined to form a cyclic carbamate, $R_E$ (on block D) is selected from the group consisting of methyl, $C_2$-$C_5$ alkyl; substituted alkyl, $C_3$-$C_5$ alkenyl; or, benzyl and substituted benzyl groups;

$R_E$ (on block B) is selected from the group consisting of methyl, $C_2$-$C_5$ alkyl; substituted alkyl, $C_3$-$C_5$ alkenyl; or, benzyl and substituted benzyl groups;

$R_B$ is selected from the group consisting of an azido function, an amine; an NH-Dde or NH-DTPM group, or $R_{S4}$ and $R_B$ can combine together to form a cyclic carbamate;

$R_P$ (adjacent $R_L$) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; and carbonate protecting groups;

$R_P$ (on group D and adjacent group C) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, $C_3$-$C_5$ alkenyl;

$R_L$ is selected from an H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other such suitable substituted benzyl type protecting group; γ-aminobutyryl, 4-N-[1-(4,4-dimethyl-2,6-dioxocyclohex-1-ylidene)ethylamino]-butyryl, 4-N-[1-(1,3-dimethyl-2,4,6(1H,3H,5H)-trioxopyrimidin-5-ylidene)methylamino]-butyryl, 4-N-Alloc-butyryl, 4-N-Fmoc-butyryl, 4-N-Boc-butyryl type protecting groups; allyloxycarbonyl, allyl ether, carbonate type protecting groups.

In an seventeenth aspect the invention provides for a tetrasaccharide building block for the preparation of synthetic heparinoids, said building block of General Formula XVII, wherein, $X_2$ is defined as in General Formula IV,
$R_H$ is defined as in General Formula I,
$R_E$ is defined as in General Formula II,
$R_B$ and $R_{S1}$ are defined as in General Formula X,
$R_S$ is defined as in General Formula I,
$R_P$ is defined as in General Formula V,
$R_L$ is defined as in General Formula I, and
$R_{B1}$ and $R_{H2}$ are defined as in General Formula XIV, or
$R_H$ is selected from the group consisting of benzyl or substituted benzyl protecting group, allyl, and allyloxycarbonyl;
$R_{H2}$ is selected from the group consisting of benzyl or substituted benzyl protecting group, allyl, and allyloxycarbonyl, or $R_{H2}$ and $R_{B1}$ independently can combine together to form a cyclic carbamate;

$R_S$ (on block B) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group; allyl, methoxymethyl, methoxyethyl, and benzyloxymethyl;

$R_S$ (on block C and adjacent the ring O) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group; allyl, methoxymethyl, methoxyethyl, and benzyloxymethyl;

$R_S$ (on block C and adjacent the O linking atom) is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group; allyl, methoxymethyl, methoxyethyl, and benzyloxymethyl; or this $R_S$ and $R_B$ may be combined to form a cyclic carbamate;

$R_S$ (on block E) is selected from the group consisting of 4-methoxyphenyl; 4-methoxybenzyl, substituted benzyl groups; alkylacyl, benzoyl, arylacyl or alkylarylacyl, and substituted alkylacyl, 4-chlorobenzoyl, arylacyl or alkylarylacyl protecting groups; allyloxycarbonyl, ethoxycarbonyl, tertbutoxycarbonyl, carbonate protecting groups; or is selected from the group consisting of 4-methoxyphenyl; substituted benzyl groups; alkylacyl, arylacyl or alkylarylacyl, and substituted alkylacyl, arylacyl or alkylarylacyl protecting groups; carbonate protecting groups; a $^t$butyldiphenylsilyloxy or other such substituted silyloxy protecting group; allyl, methoxymethyl, and methoxyethyl, benzyloxymethyl; or this $R_S$ and $R_H$ can be combined to form a cyclic acetal or ketal moiety;

General Formula XVII (Block E-D-C-B)

$R_E$ (on block D) is selected from the group consisting of methyl, $C_2$-$C_5$ alkyl; substituted alkyl, $C_3$-$C_5$ alkenyl; or, benzyl and substituted benzyl groups;

$R_E$ (on block B) is selected from the group consisting of methyl, $C_2$-$C_5$ alkyl; substituted alkyl, $C_3$-$C_5$ alkenyl; or, benzyl and substituted benzyl groups;

$R_B$ is selected from the group consisting of an azido function, an amine; an NH-Dde or NH-DTPM group, or $R_{S4}$ and $R_B$ can combine together to form a cyclic carbamate;

$R_{B1}$ is selected from the group consisting of an azido function, an amine; an NH-Dde or NH-DTPM group, or $R_{H2}$ and $R_{B1}$ can combine together to form a cyclic carbamate;

$R_P$ (on block D adjacent block E) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; and carbonate protecting groups;

$R_P$ (on block D adjacent block C) is selected from the group consisting of 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, and $C_3$-$C_5$ alkenyl;

$X_2$ is selected from a hydroxyl group; thioalkyl, thioaryl, halogen, trichloroacetimidoyl, phosphate and related phosphate ester type leaving groups, a 'butyldiphenylsilyloxy or other such substituted silyloxy protecting group; and the stereochemistry may be alpha or beta.

In an eighteenth aspect the invention provides for a pentasaccharide building block for the preparation of synthetic heparinoids, said building block of General Formula XVIII, alkylacyl, arylacyl or alkylarylacyl, and substituted alkylacyl, arylacyl or alkylarylacyl protecting groups; carbonate protecting groups; a 'butyldiphenylsilyloxy or other such substituted silyloxy protecting group; allyl, methoxymethyl, methoxyethyl, and benzyloxymethyl, or $R_{S4}$ and $R_B$ may be combined to form a cyclic carbamate; $R_S$ on block E C B A, ($R_{S1,2,3,5}$ in the claims) can be a 'butyldiphenylsilyloxy or other such substituted silyloxy protecting group; allyl, methoxymethyl, methoxyethyl, and benzyloxymethyl.

In a nineteenth aspect, the invention provides a method for the preparation of compounds of the eighth aspect, involving the step of reacting a compound of the second or third aspect with a compound of the first or seventh aspect to form a new glycosidic bond.

In a twentieth aspect, the invention provides a method for the preparation of compounds of the eighth aspect, involving the step of selectively removing the protecting group $R_M$ from compounds of the ninth aspect and oxidizing the product of said deprotection.

In a twenty first aspect, the invention provides a method for the preparation of compounds of the tenth aspect, involving the step of reacting a compound of the fifth aspect with a compound of the fourth or seventh aspect to form a new glycosidic bond.

In a twenty second aspect, the invention provides a method for the preparation of compounds of the eleventh aspect, involving the step of reacting a compound of the fifth aspect with a compound of the sixth or seventh aspect to form a new glycosidic bond.

General Formula XVIII

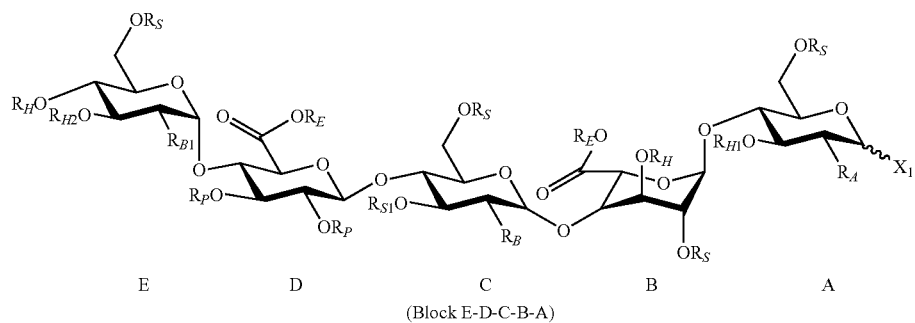

(Block E-D-C-B-A)

wherein, $X_1$ is defined as in General Formula I $R_A$ and $R_{H1}$ are defined as in General Formula VIII, and $R_{H1}$ can also be allyl and alloxycarbonyl or $R_A$ and $R_{H1}$ can combine together to form a cyclic carbamate.

$R_S$ is defined as in General Formula I, $R_H$ is defined as in General Formula I or $R_H$ is selected from the group consisting of benzyl or substituted benzyl protecting group, allyl, and allyloxycarbonyl, $R_E$ is defined as in General Formula II, $R_B$ and $R_{S1}$ are defined as in General Formula X, $R_P$ is defined as in General Formula V, and may be benzyl, $R_P$ (adjacent the link from D to C) may also be silyl protecting groups, carbamate protecting groups, $C_3$-$C_5$ alkenyl, and $R_{B1}$ and $R_{H2}$ are defined as in General Formula XIV or $R_{H2}$ is selected from the group consisting of benzyl or substituted benzyl protecting group, allyl, allyloxycarbonyl, or $R_{H2}$ and $R_{B1}$ independently can combine together to form a cyclic carbamate, $R_{S1}$ on block C($R_{S4}$ in the claims) is selected from the group consisting of 4-methoxyphenyl; substituted benzyl groups;

In a twenty third aspect, the invention provides a method for preparation of compounds of the thirteenth aspect involving the reaction of a compound of the fourth or seventh aspect with a suitable donor molecule, to form a new glycosidic bond.

In a twenty fourth aspect, the invention provides a method for the preparation of compounds of the fourteenth aspect involving the step of using any one or more of the compounds of the fourth, fifth, sixth, seventh, tenth, eleventh, twelfth or thirteenth aspect in a glycosidic bond forming reaction.

In a twenty fifth aspect, the invention provides a method for the preparation of compounds of the fifteenth aspect involving the step of using any one or more compounds of the first, second, third, fourth, seventh, eighth and ninth aspects in a glycosidic bond forming reaction.

In a twenty sixth aspect, the invention provides a method for the preparation of compounds of the sixteenth aspect involving the step of using any one or more of the compounds of the first, second third, fourth, fifth, seventh, eighth, ninth, tenth, thirteenth or fifteenth aspect in a glycosidic bond forming reaction.

In a twenty seventh aspect, the invention provides a method for the preparation of compounds of the seventeenth aspect involving the step of using any one or more of the compounds of the second, third, fourth, fifth, seventh, tenth, eleventh, twelfth, thirteenth or fourteenth aspect in a glycosidic bond forming reaction.

In a twenty eighth aspect, the invention provides a method for the preparation of compounds of the eighteenth aspect involving the step of using any one or more of the compounds of the 1, 2, 3, 4, 5, 7, 8, 9, 10, 11, 12, 13, 14, or 15, 16 or $17^{th}$ aspect in a glycosidic bond forming reaction.

BEST MODE

Figure 1:
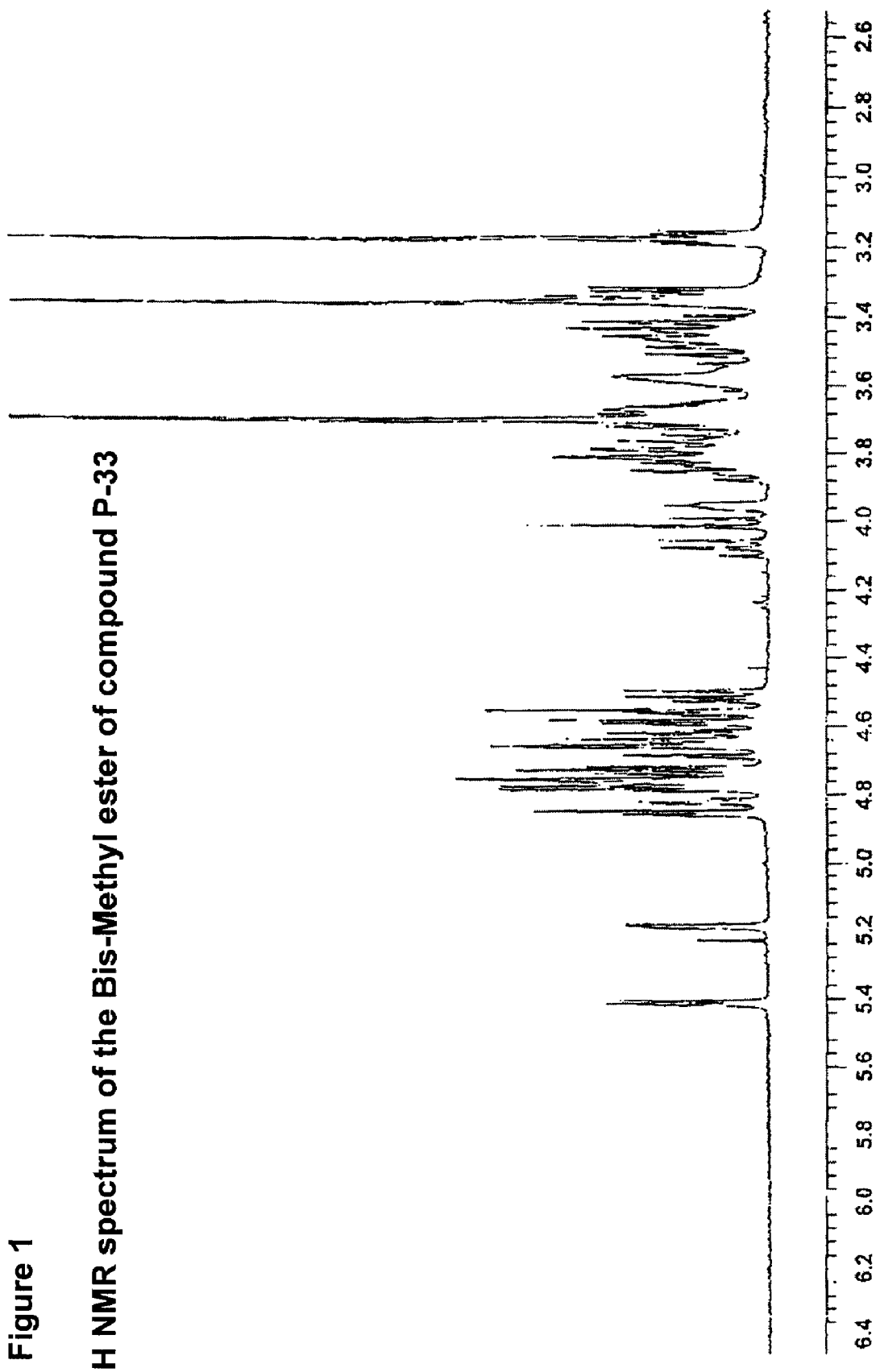
FIG. 1 is a proton NMR spectrum of the Bis-methyl ester of compound P-33.

Embodiments of the invention will be described with reference to the following examples: Standard operating protocols (SOP's) are provided for many of the examples.

LIST OF ABBREVIATIONS

AcO: Acetyl,
All: Allyl,
Alloc: Allyloxycarbonyl,
Bn: Benzyl,
Bz: Benzoyl,
CAN: $(NH_4)_2Ce^{IV}(NO_3)_6$, ceric ammonium (IV) nitrate,
ClAc: Monochloroacetyl,
Cres: p-Tolyl,
DCC: Dicyclohexylcarbodiimide,
Dde: 1-(4,4-dimethyl-2,6-dioxocyclohex-ylidene)ethyl,
DEAD: Diethyl azodicarboxylate,
DIPEA: Diisopropylethylamine,
DMAP: 4-N,N-dimethylaminopyridine,
DMF: N,N-Dimethylformamide,
DMTST: Dimethyl (methylthio)sulfoniumtetrafluoromethansulfonate,
DTPMB: 2,6-di-tert-butyl-4-methylpyridine
DTPM: (1,3-dimethyl-2,4,6 (1H, 3H, 5H)-trioxopyrimidin-5-ylidene)methyl,
Lev: 4-Oxopentanoyl,
MCPBA: 3-chloroperbenzoic acid,
Mes: Methanesulfonyl,
Mp: 4-Methoxyphenyl,
Mpm: 4-methoxybenzyl,
NBS: N-Bromosuccinimide,
NIS: N-Iodosuccinimide,
NMP: N-Methylpyrollidone
NPht: N-Phthaloyl
PDC: Pyridiniumdichromate,
Pent: n-Pentenyl,
$Ph_3P$: Triphenylphosphine,
Piv: Pivaloyl,
TBAF: Tetrabutylammoniumfluoride,
TBDMS: tert-Butyldimethylsilyl,
TBDPS: tert-Butyldiphenylsilyl,
TCA: Trichloroacetimidyl,
TEMPO: 2,2,6,6-Tetramethyl-1-piperidinyloxyl,
TFA: Trifluoroacetic acid,
TFAA: Trifluoroacetic acid anhydride,
Tf: Trifluoromethanesulfonyl,
$TfN_3$: Trifluoromethanesulfonyl azide, prepared from $NaN_3$ and $Tf_2O$,
TfOH: Trifluoromethanesulfonic acid,
THF: Terahydrofuran,
TMS: Trimethylsilyl,
Tos: p-Toluenesulfonyl,
p-TosOH: p-Toluenesulfonic acid,
Trit: Triphenylmethyl.

Standard Operating Procedures
Standard Operating Procedure 1: Formation of Benzylidene acetals
Standard Operating Procedure 2: Formation of p-Methoxybenzylidene acetals
Standard Operating Procedure 3: Formation of isopropylidene acetals:
Standard Operating Procedure 4: Dealkylidenation (Removal of isopropylidene, benzylidene and p-methoxybenzylidene)
Standard Operating Procedure 5: Regioselective opening of the p-methoxybenzyliden acetal to a 6-O-pMethoxybenzyl ether
Standard Operating Procedure 6: Regioselective opening of a benzylidene ring to a 4-O-benzyl ether
Standard Operating Procedure 7: Introduction of a benzyl or p-methoxybenzyl ether
Standard Operating Procedure 8: Introduction of a tert-butyl-diphenylsilyl ether
Standard Operating Procedure 9: Cleavage of a tert-Butyl-diphenylsilyl ether
Standard Operating Procedure 10: Introduction of a N-DTPM-group
Standard Operating Procedure 11: Cleavage of a N-DTPM-group
Standard Operating Procedure 12: Introduction of an azide group via diazo transfer reaction
Standard Operating Procedure 13: Hydrolysis of thioglycosides (NBS)
Standard Operating Procedure 14: Hydrolysis of thioglycosides (NIS)
Standard Operating Procedure 15: Chemoselective Oxidation to Uronic acids
Standard Operating Procedure 16: Methyl ester formation on the Uronic acids
Standard Operating Procedure 17: Regioselective 6-O-Benzoylation
Standard Operating Procedure 18: Common procedure for O-Benzoylation
Standard Operating Procedure 19: Common procedure for O-Acetylation
Standard Operating Procedure 20: PDC-oxidation of alcohols to carboxylic acids
Standard Operating Procedure 21: Chemoselective 1-O-Benzoyl cleavage
Standard Operating Procedure 22: Deacylation under Zemplen conditions
Standard Operating Procedure 23: Introduction of the 4-Oxopentanoyl (=Levulinoyl) group
Standard Operating Procedure 24: Cleavage of the 4-Oxopentanoyl (=Levulinoyl) group
Standard Operating Procedure 25: Formation of Trichloroacetimidates
Standard Operating Procedure 26: Regioselective introduction of a 6-O-pMethoxyphenyl group under Mitsunobu conditions
Standard Operating Procedure 27: Cleavage of the p-Methoxyphenyl ether Standard Operating Procedure 28: Cleavage of p-Methoxybenzyl ethers
Standard Operating Procedure 29: Formation of a 2,3-cyclic carbamate
Standard Operating Procedure 30: Cleavage of the N-phthaloyl group
Standard Operating Procedure 31: Introduction of a thiocresyl ether at the reducing end
Standard Operating Procedure 32: Glycosylation with thioglycosides NIS-promoted glycosylation
DMTST promoted glycosylations:
Standard Operating Procedure 33: Glycosylations with trichloroacetimidates
Standard Operating Procedure 34: Glycosylations using 2,3-cyclocarbamoyl protected pThiocresyl glycosides as glycosyl donors
Standard Operating Procedure 35: Introduction of an Alloc-group
Standard Operating Procedure 36: Cleavage of an Alloc-group
Standard Operating Procedure 37: Lewis acid mediated benzylation
Standard Operating Procedure 38: benzylation under mild basic conditions
Standard Operating Procedure 39: Ester cleavage under very mild conditions Standard Operating Procedure 1: Formation of Benzylidene Acetals The starting material (47.5 mmol) was dissolved in acetonitrile (100-200 mL) and reacted with benzaldehyde dimethyl acetal (1.2 equiv.) and a catalytic amount of p-toluenesulphonic acid monohydrate (0.01-0.1 equiv). The reaction was stirred at 50° C. under reduced pressure (350 mbar) until the TLC shows completion. Subsequently, the mixture was neutralized with triethylamine (pH=9) and concentrated in vacuo. The remaining residue was dissolved in an organic solvent (e.g. dichloromethane or ethyl acetate) and extracted with $H_2O$, saturated brine solution, dried over $Na_2SO_4$ and concentrated. Final purification was achieved either by crystallization or by silica gel chromatography. The typical yields for the product formation varied between 70 and 95%.

Standard Operating Procedure 2: Formation of p-Methoxybenzylidene Acetals

The starting material (47.5 mmol) was dissolved in DMF/acetonitrile (1/1, 100-200 mL) and reacted with p-methoxybenzaldehyde dimethyl acetal (1.2 equiv.) and a catalytic amount of p-toluenesulphonic acid monohydrate (0.01-0.1 equiv). The reaction was stirred between 50-60° C. under reduced pressure (350 mbar) until the TLC shows completion. Subsequently, the mixture was neutralized with triethylamine (pH≈9) and concentrated in vacuo. The remaining residue was dissolved in an organic solvent (e.g. dichloromethane or ethyl acetate) and extracted with $H_2O$, saturated brine solution, dried over $Na_2SO_4$ and concentrated. Final purification was achieved either by crystallization or by silica gel chromatography. The typical yields for the product formation varied between 70 and 85%.

Standard Operating Procedure 3: Formation of Isopropylidene Acetals:

A solution of starting material (10 mmol) and catalytic amounts of camphorsulfonic acid (0.01-0.1 equiv) in 2,2-dimethoxypropane (50 mL) was stirred at 25° C. until completion, neutralized with triethylamine and concentrated. The remaining residue was dissolved in an organic solvent (e.g., dichloromethane or ethyl acetate) and extracted with $H_2O$ and saturated brine solution. The organic layer was dried over $Na_2SO_4$ and concentrated. Final purification was achieved either by crystallization or by silica gel chromatography. The typical yields for the product formation varied between 75 and 93%.

Standard Operating Procedure 4: Dealkylidenation (Removal of isopropylidene, benzylidene and p-methoxybenzylidene)

A solution of the acetal (31 mmol) in 150 mL dichloromethane was cooled to 0° C. and reacted with 80% aqueous TFA (20.0 mL, cooled to 0° C.). After stirring at 0° C. until completion, the reaction mixture was neutralized with 30% NaOH solution and extracted with water and saturated brine solution. The organic layer was dried over $Na_2SO_4$ and concentrated. Final purification was achieved either by crystallization or by silica gel chromatography. The typical yields for the product formation varied between 70 and 95%.

Modification Using p-TosOHxOH$_2$ in MeOH/CH$_3$CN for Cleavage:

The acetal (16.6 mmol) was dissolved in 100 mL of dry acetonitrile and 25 mL MeOH and the solution was reacted with catalytic amounts of p-TosOHxOH$_2$. The reaction mixture was heated at elevated Temperature (between 40 and 60° C.) until completion and then neutralized with Et$_3$N, concentrated in vacuo and purified either by crystallization or by silica gel chromatography. The typical yields for the product formation varied between 70 and 95%.

Standard Operating Procedure 5: Regioselective Opening of the p-Methoxybenzyliden Acetal to a 6-O-pMethoxybenzyl Ether A suspension of the starting sugar (10.2 mmol), molecular sieves 3 Å (6.5 g, freshly activated) and Na(CN)BH$_3$ (3.85 g, 58.2 mmol) in dry DMF (90 mL) was stirred for 1 hr at r.t. and cooled down to 0° C. Subsequently, a solution of TFA (11.2 mL, 143.9 mmol in 51 mL dry DMF) was added dropwise and stirring continued at 50 to 60° C. until completion of the reaction. The reaction mixture was cooled to 20° C., diluted with ethyl acetate and extracted with a saturated aqueous NaHCO$_3$ solution and filtered through a celite pad. The combined organic layers were washed with saturated brine solution, dried over MgSO$_4$ and concentrated. Final purification was achieved either by crystallization or by silica gel chromatography. The typical yields for the product formation varied between 70 and 90%.

Standard Operating Procedure 6: Regioselective Opening of a Benzylidene Ring to a 4-O-benzyl Ether A solution of the starting material (3.4 mmol) in 25 mL dichloromethane is cooled to 0° C. and to it is added of a solution of BH$_3$ in THF (1 M, 34 mL) and a solution of Bu$_2$BOTf in dichloromethane (1 M, 3.7 mL). The reaction is stirred at 0° C. till completion and then quenched with 10 mL Et$_3$N and 10 mL MeOH, concentrated and coevaporated three times with toluene. Final purification was achieved either by crystallization or by silica gel chromatography. The typical yield for the product formation varied between 75 and 90%.

Standard Operating Procedure 7: Introduction of a Benzyl or p-methoxybenzyl Ether The starting material (40.2 mmol) was dissolved in dry N,N'-dimethylformamide (100 mL) at 0° C. and reacted with NaH (48.24 mmol, 1.2 eq per OH to be benzylated). Then benzyl bromide (1.1 eq per OH to be benzylated) was added dropwise and stirring continued at 0° C. until completion. The same conditions were applied for the introduction of an allyl ether (Allylbromide served as allylating reagent).

The excess of NaH was neutralized by careful addition of acetic acid, followed by concentration of the reaction mixture in vacuo. The residue was dissolved in ethyl acetate and subsequently washed with water, 10% aqueous HCl solution, saturated aqueous NaHCO$_3$ solution, saturated brine solution, dried over $Na_2SO_4$ and concentrated in vacuo. Final purification was achieved either by crystallization or by silica gel chromatography. The typical yield for the product formation varied between 70 and 92%.

The same procedure was followed for the formation of the p-methoxybenzyl ether except that p-methoxybenzyl chloride was added to the reaction instead of benzyl bromide and the reaction was performed between 50 and 60° C.

Standard Operating Procedure 8: Introduction of a tert-butyldiphenylsilyl Ether

A mixture of the starting material (29.0 mmol) and imidazole (70.1 mmol) was dissolved in 80 mL anhydrous DMF and heated to 55° C. To the solution was added tert-butyldiphenylchlorosilane (8.30 mL, 31.9 mmol) and stirring continued at 55° C. until completion. The reaction mixture was then cooled to 20° C. and quenched with aqueous $NaHCO_3$ solution. After concentration in vacuo, the residue was taken up in ethyl acetate and the organic phase washed successively with water, 10% aqueous citric acid, water, saturated brine solution, dried over $Na_2SO_4$ and evaporated. Final purification was achieved either by crystallization or by silica gel chromatography. The typical yields for the product formation varied between 85 and 95%.

Standard Operating Procedure 9: Cleavage of a tert-Butyldiphenylsilyl Ether

To a solution of the silyl ether (2.15 mmol) in 2.5 mL dry THF and acetic acid (3.44 mmol) was added 1 M TBAF solution in THF (3.22 mL) and stirring continued till completion of the reaction. Subsequently, the reaction mixture was concentrated in vacuo. Final purification was achieved either by crystallization or by silica gel chromatography. The typical yields for the product formation varied between 85 and 97%.

Standard Operating Procedure 10: Introduction of a N-DTPM-Group

To a solution of the starting amine (24.5 mmol) in methanol (60 mL) is added a solution of the DTPM reagent (5.43 g, 25.7 mmol) in methanol (60 mL) at 60° C. After completion of the reaction, the reaction mixture was concentrated in vacuo, taken up in dichloromethane, extracted with water and saturated brine solution, dried over $MgSO_4$ and evaporated. Final purification was achieved either by crystallization or by silica gel chromatography. The typical yields for the product formation varied between 85 and 97%.

Standard Operating Procedure 11: Cleavage of a N-DTPM-Group

The starting material (40.94 mmol) was dissolved in dry DMF (50 mL) and reacted with ethylene diamine (20 mL) at room temperature until completion. The reaction mixture was concentrated in vacuo and coevaporated with toluene. The residue was suspended in $CHCl_3$ and filtered through a Celite pad. The filtrate was evaporated and final purification of the residue was achieved either by crystallization or by silica gel chromatography. The typical yields for the product formation varied between 85 and 92%.

Standard Operating Procedure 12: Introduction of an Azide Group Via Diazo Transfer Reaction a) Preparation of a trifluoromethansulfonylazide Solution:

A solution of sodium azide (492 mmol) in water (80 mL) was prepared under $N_2$-atmosphere. To this stirred solution was added dichloro-methane (100 mL) at 0° C., followed by the addition of triflic anhydride (16.5 mL) over 10 min. The mixture was further stirred for 2 hours at 0° C., the organic layer was separated and the aqueous layer was extracted with dichloromethane (2×40 mL). The combined organic layers were washed with saturated, aqueous $NaHCO_3$ solution (80 mL), water (80 mL) and dried over $Na_2SO_4$. After filtration, this solution was directly used for the diazotransfer reaction.

b) Diazotransfer Reaction:

To a solution of the starting material (26.0 mmol) and 4-N,N'-(dimethylamino)pyridine (14.5 g) in acetonitrile (100 mL) was added dropwise $TfN_3$-solution (85 mL) at room temperature within 10 min. The reaction was stirred till complete conversion of the starting material into the product. The reaction mixture was concentrated in vacuo to 30 mL and suspended in chloroform. After filtration through a Celite pad, the filtrate was concentrated and the residue was purified by filtration through a short silica gel pad. The typical yields for the product formation varied between 85 and 95%.

Standard Operating Procedure 13: Hydrolysis of Thioglycosides (NBS)

The starting thioglycoside (33.4 mmol) was suspended in 240 mL Acetone and 18 mL of distilled water and stirred for 45 min at −20° C. After addition of NBS (155 mmol) stirring was continued at −20° C. After completion, the reaction was stopped by addition of $NaS_2O_3/NaHCO_3$ (20% aqueous solution, 1/1) and the mixture diluted with ethyl acetate, subsequently washed with water and saturated brine solution. The organic layer was dried over $Na_2SO_4$ and concentrated in vacuo. Final purification was achieved either by crystallization or by silica gel chromatography. The typical yields for the product formation varied between 75 and 90%.

Standard Operating Procedure 14: Hydrolysis of Thioglycosides (NIS)

The starting thioglycoside (33.4 mmol) was suspended in 240 mL Acetone and 18 mL of distilled water and stirred for 45 min at −20° C. After addition of NIS (56.8 mmol) and TMSOTf (2.84 mmol) stirring was continued until completion. The reaction was stopped by addition of $NaS_2O_3/NaHCO_3$ (20% aqueous solution, 1/1), diluted with ethyl acetate and washed with water and saturated brine solution. The organic layer was dried over $Na_2SO_4$ and concentrated in vacuo. Final purification was achieved either by crystallization (e.g. petroleum spirit/ethylacetate) or by silica gel chromatography. The typical yields for the product formation varied between 79 and 92%.

Standard Operating Procedure 15: Chemoselective Oxidation to Uronic Acids

A solution of the starting material (20.0 mmol) in dichloromethane (141 mL) was cooled to 0° C. and subsequently mixed with TEMPO (0.205 mmol in 12.8 mL dichloromethane), Aliquat 336 (N-methyl-N,N-dioctyl-1-octanaminium chloride) (12.8 mL of a 0.08 M solution in dichloromethane) and KBr (2.08 mmol in 4.17 mL $H_2O$) and stirring continued at 0° C. After 5 mins, a suspension of $Ca(OCl)_2$ (43.6 mmol) and $NaHCO_3$ (43.6 mmol) in 135 mL $H_2O$ was added within 15 mins to the reaction mixture and stirring at 0° C. was continued till completion. The reaction was concentrated in vacuo and freeze dried. The crude residue was used as such for the next reactions.

Standard Operating Procedure 16: Methyl Ester Formation on the Uronic Acids

The crude residue of the oxidation to the uronic acid was dissolved in 50 mL Toluene and 50 mL Methanol and titurated with $TMSCHN_2$-solution (2M in hexane) until completion. The reaction mixture was quenched with acetic acid to destroy excess of esterification reagent and evaporated in vacuo. Final purification was achieved by silica gel chromatography. The typical yields for the product formation varied between 65 and 80% over the steps oxidation and esterification.

Standard Operating Procedure 17: Regioselective 6-O-Benzoylation

The starting material (32.04 mmol) was dissolved in dry dichloromethane (50 mL) and dry pyridine (10 mL) and cooled down to −45° C. Benzoyl chloride (32.04 mmol) was added dropwise and stirring continued at −45° C. until completion. The reaction was concentrated in vacuo and coevaporated with toluene three times. The remaining residue was dissolved in dichloromethane and washed with 10% aqueous citric acid solution, saturated aqueous $NaHCO_3$ solution and saturated brine solution, dried over $Na_2SO_4$ and evaporated in vacuo. Final purification was achieved either by crystallization or by silica gel chromatography. The typical yields for the product formation varied between 75 and 94%.

Standard Operating Procedure 18: Common Procedure for O-Benzoylation

To a solution of the starting material (11.9 mmol) and DMAP (13.6 mmol) in 1,2-dichloroethane was added dropwise benzoylchloride (1.7 g, 12.1 mmol). at 0° C. The mixture was then left to stir until completion (dependent on the substrate between 20 to 55° C.). Subsequently, the reaction mixture was diluted with dichloromethane and washed with water, 5% $NaHSO_4$ solution, saturated aqueous $NaHCO_3$ solution and saturated brine solution. The organic layer was dried over $MgSO_4$ followed by removal of the solvent in vacuo to give a crude residue. Final purification was achieved either by crystallization or by silica gel chromatography. The typical yields for the product formation varied between 80 and 96%.

Standard Operating Procedure 19: Common Procedure for O-Acetylation

To a suspension of the starting material (235 mmol, 3 acetylation sites) in pyridine (350 mL) at 0° C. was added dropwise acetic anhydride (175 mL). After completion of the addition, the reaction was allowed to return to room temperature and stirred until completion. The reaction mixture was evaporated to dryness and 3× coevaporated with toluene. The residue was taken up in dichloromethane and washed with 5% aqueous $NaHSO_4$-solution, saturated aqueous $NaHCO_3$-solution, water and saturated brine solution. The organic layer was dried over $MgSO_4$ and evaporated. Final purification of the residue was achieved either by crystallization or by silica gel chromatography. The typical yields for the product formation varied between 88 and 98%.

Standard Operating Procedure 20: PDC-Oxidation of Alcohols to Carboxylic Acids

The starting material (1.15 mol) was dissolved in anhydrous DMF (7.0 mL) and reacted with PDC (11.5 mmol) under stirring at room temperature until complete conversion into the uronic acid. The reaction mixture was subsequently poured into 50 mL water and the whole extracted with diethyl ether. The combined ether layers were washed with 10% aqueous citric acid solution, filtered through a short silica gel pad, dried over $MgSO_4$, evaporated and dried under high vacuum.

Standard Operating Procedure 21: Chemoselective 1-O-Benzoyl Cleavage

The starting material (36.8 mmol) was dissolved in dry DMF (80 mL) and cooled to 0° C. Subsequently, hydrazine acetate (44.06 mmol) was added and stirring continued until completion. After addition of acetone and acetic acid the reaction mixture was concentrated in vacuo. The residue was dissolved in dichloromethane and extracted with 10% aqueous citric acid solution, saturated $NaHCO_3$ solution, water and saturated brine solution, dried over $MgSO_4$, evaporated and dried under high vacuum. Final purification was achieved either by crystallization or by silica gel chromatography. The typical yields for the product formation varied between 72 and 88%.

Standard Operating Procedure 22: Deacylation Under Zemplen Conditions

The starting material (23.7 mmol) was suspended in dry MeOH (70 mL) and stirred for 30 mins at 0° C. Subsequently, NaOMe (0.1 equiv./0-Acyl group) was added (positive flush of $N_2$) and stirring was continued at 0° C. until completion. Finally, the reaction was neutralized with 10% aqueous HCl and the solvent evaporated. Final purification was achieved either by crystallization or by silica gel chromatography. The typical yield for the product formation varied between 90 and 98%.

Standard Operating Procedure 23: Introduction of the 4-Oxopentanoyl (=Levulinoyl) Group Preparation of the $Lev_2O$ Solution:

To a solution of DCC (31.2 mmol) in 100 mL dichloromethane was added levulinic acid (62.4 mmol) and DIPEA (62.42 mmol). The supernatant was used as such for the levulination reaction.

Reaction

The above $Lev_2O$ solution was added to a solution of the starting sugar (15.6 mmol) dissolved in 25 mL of dry dichloromethane and stirring was continued until completion. Subsequently, the reaction mixture was filtered through a Celite pad and all combined organic layers were extracted with 10% aqueous citric acid solution, saturated aqueous brine solution, dried with $Na_2SO_4$ and concentrated. Final purification was achieved either by crystallization or by silica gel chromatography. The typical yields for the product formation varied between 85 and 96%.

Standard Operating Procedure 24: Cleavage of the 4-Oxopentanoyl (=Levulinoyl) Group A solution of the starting sugar (1.28 mmol) and acetic acid (1.35 mL) in pyridine (5.0 mL) was cooled to 0° C. followed by addition of hydrazine hydrate (200 µL). Stirring at 0° C. was continued until completion and the reaction mixture diluted with dichloromethane, subsequently extracted with 10% aqueous citric acid, 10% aqueous $NaHCO_3$ solution, saturated brine solution, dried over $Na_2SO_4$, filtered and concentrated. Final purification was achieved either by crystallization or silica gel chromatography. The typical yields for the product formation varied between 80 and 95%.

Standard Operating Procedure 25: Formation of Trichloroacetimidates a) with DBU:

A solution of the starting sugar (1.99 mmol) and trichloroacetonitrile (601 µL, 5.87 mmol) in 5 mL dry dichloromethane was stirred at room temperature for 30 min. The reaction mixture was then cooled to 0° C. and DBU (100 µmol) added. Stirring was continued until completion (dependent on the substrate, stirring was performed from 0° C. to 20° C.). The reaction mixture was concentrated to one half of its volume and directly loaded on a short plug of silica gel and purified via silica gel chromatography. The typical yields for the product formation varied between 78 and 95%.

b) with $K_2CO_3$:

A solution of the starting sugar (1.99 mmol) and trichloroacetonitrile (601 µL, 5.87 mmol) in 5 mL dry dichloromethane is stirred at r.t. for 30 min. The reaction mixture was then cooled down to 0° C. and anhydrous $K_2CO_3$ (19.9 mmol) added. The reaction was stirred at 0° C. till completion and then filtered through a celite pad. The filtrate was dried over $Na_2SO_4$ and evaporated. Final purification was achieved either by crystallization or by silica gel chromatography. The typical yield for the product formation varied between 78 and 95%.

Standard Operating Procedure 26: Regioselective Introduction of a 6-O-p-Methoxyphenyl Group Under Mitsunobu Conditions A solution of the starting sugar (13.52 mmol), 4-methoxyphenol (20.3 mmol) and triphenylphosphine (20.3 mmol) in 85 mL dry dichloromethane was stirred at 0° C. for 45 min. After addition of DEAD-reagent (22.9 mmol) at 0° C., the reaction mixture was further stirred at room temperature until completion, filtered through a celite pad, diluted with dichloromethane and extracted with 10% aqueous $NaHCO_3$/NaOH solution (1/1), 10% aqueous citric acid solution and aqueous saturated brine solution. The organic layer was dried over $Na_2SO_4$ and concentrated. Final purification was achieved by silica gel chromatography. The typical yield for the product formation varied between 70 and 89%.

Standard Operating Procedure 27: Cleavage of the p-Methoxyphenyl Ether

The starting material (1.18 mmol) was dissolved in 30 mL acetonitrile and 7.5 mL water and cooled to 0° C. Subsequently, CAN (3.83 mmol) was added and stirring continued at 0° C. until completion. The reaction mixture was diluted with ethyl acetate and extracted with water. The aqueous layer was made alkaline by addition of solid $NaHCO_3$ and back extracted with ethyl acetate. The combined organic layers were extracted with saturated aqueous $NaHCO_3$ solution and saturated brine solution, dried over $MgSO_4$ and evaporated. Final purification was achieved by silica gel chromatography. The typical yields for the product formation varied between 73 and 89%.

Standard Operating Procedure 28: Cleavage of p-Methoxybenzyl Ethers

The starting material (0.60 mmol) was dissolved in 27 mL acetonitrile and 3.0 mL water and cooled to 0° C. Subsequently, CAN (4.5 equiv.) was added and stirring continued from 0° C. to room temperature until completion. The reaction mixture was diluted with ethyl acetate and extracted with water. The aqueous layer was made alkaline by addition of solid $NaHCO_3$ and back extracted with ethyl acetate. The combined organic layers were extracted with saturated aqueous $NaHCO_3$ solution and saturated brine solution, dried over $MgSO_4$ and evaporated. Final purification was achieved by silica gel chromatography. The typical yields for the product formation varied between 73 and 85%.

Standard Operating Procedure 29: Formation of a 2,3-cyclic Carbamate

To a stirred solution of the starting material (3.56 mmol) in dichloromethane (100 mL) and 10% aqueous solution of $NaHCO_3$ (75 mL) was added a solution of triphosgene (1.25 mmol) in 10 mL dry dichloromethane. The reaction was stirred at room temperature till completion. The organic phase was washed with water, dried over $Na_2SO_4$, filtered and concentrated. Final purification was achieved either by crystallization or silica gel chromatography. The typical yield for the product formation varied between 75 and 95%.

Standard Operating Procedure 30: Cleavage of the N-phthaloyl Group

The N-phthaloylated starting material (45.9 mmol) was dissolved in n-butanol (200 mL) and treated with 1,2-diaminoethane (50 mL) at 100° C. After stirring at 100° C. until completion, the reaction mixture was concentrated in vacuo, coevaporated with toluene three times and dried under high vacuum. Final purification was achieved by silica gel chromatography. The typical yield for the product formation varied between 78 and 92%.

Standard Operating Procedure 31: Introduction of a Thiocresyl Ether at the Reducing End A solution of the 1-O-glycosyl acetate (10.48 mmol) and p-thiocresol (12.58 mmol) in dry dichloromethane (30 mL) was stirred at 0° C. and subsequently activated by the addition of boron trifluoride diethylether complex (12.58 mmol) over 5 min. Stirring was continued (0° C.→20° C.) until completion and the reaction stopped by the addition of triethyl amine (14.0 mmol). The reaction mixture was diluted with dichloromethane and extracted with saturated $NaHCO_3$-solution, water and saturated brine solution, dried over $MgSO_4$ and evaporated in vacuo. Final purification was achieved by crystallization or silica gel chromatography. The typical yield for the product formation varied between 81 and 92%.

Standard Operating Procedure 32: Glycosylation with Thioglycosides a) NIS-Promoted Glycosylation A mixture of glycosyl acceptor (1 mmol), thioglycoside (1 mmol) and 1.0 g of freshly activated molecular sieves in 20 mL of a dry solvent (e.g. $CH_3CN$, $CH_2Cl_2$, Toluene, Ether) was stirred for 45 min at r.t and cooled down to the reaction temperature. Subsequently, N-Iodosuccinimide (1.7 mmol) was added and stirring continued for 20 min at the reaction temperature. After the addition of a Lewis acid as promoter (e.g. TfOH, 85-170 µmol), stirring was continued at the reaction temperature until completion. The reaction mixture was quenched with triethyl amine, filtered through a celite pad and extracted with a 10% aqueous $KHCO_3$/$Na_2S_2O_3$ solution, water and saturated brine solution, dried over $MgSO_4$ and evaporated. Final purification was achieved by silica gel column chromatography. The typical yields for the product formation varied between 65 and 85%.

b) DMTST Promoted Glycosylations:

A mixture of glycosyl acceptor (1 mmol), thioglycoside (1 mmol) and 1.0 g of freshly activated molecular sieves in 20 mL of a dry solvent (e.g., $CH_3CN$, $CH_2Cl_2$, Toluene, Ether) was stirred for 45 min at r.t. and cooled down to the reaction temperature. Subsequently, DMTST (3-5 equiv.) was added and stirring continued at the reaction temperature until completion. The reaction mixture was quenched with triethyl amine, filtered through a celite pad and extracted with aqueous $NaHCO_3$-solution, water and saturated brine solution, dried over $Na_2SO_4$, concentrated in vacuo and purified by silica gel column chromatography. The typical yields for the product formation varied between 50 and 85%.

Standard Operating Procedure 33:

Glycosylations with Trichloroacetimidates

A suspension of the trichloroacetimidate (1.54 mmol), glycosyl acceptor (1.13 mmol) and freshly activated molecular sieves (1.0 g) in an anhydrous solvent (e.g., $CH_3CN$, $CH_2Cl_2$, Toluene, Ether, 20 mL) was stirred at r.t. for 1 h and then cooled to reaction temperature. Subsequently, a catalytic amount of a promoter (e.g., TMSOTf, 0.01-0.1 equiv.) was added and stirring continued at reaction temperature until completion. The reaction was quenched with triethylamine) and filtered through a Celite pad. The combined organic layers were washed with aqueous $NaHCO_3$-solution and saturated brine solution, dried over $Na_2SO_4$, concentrated in vacuo and purified by silica gel column chromatography. The typical yields for the product formation varied between 50 and 85%.

Standard Operating Procedure 34: Glycosylations Using 2,3-cyclocarbamoyl Protected pThiocresyl Glycosides as Glycosyl Donors PhSCl (0.2 mmol, 2 equiv.) in dry dichloromethane (1 mL) was added dropwise to a mixture of AgOTf (0.2 mmol) in dry dichloromethane (2 mL) at −78° C. containing freshly activated molecular sieves 3 Å. After stirring for 15 mins at −78° C., a solution of the thioglycoside (0.1 mmol, 1 equiv.) and DTBMP (0.2 mmol, 2 equiv.) in dry dichloromethane (2 mL) was slowly added. After further stirring for 15 mins at −78° C., the glycosyl acceptor (0.2 mmol, 2 equiv.) in dry dichloromethane (1 mL) was slowly added and stirring continued until completion. The reaction was quenched with saturated aqueous NaHCO$_3$ solution (1 mL), warmed to r.t. and diluted with dichloromethane. The organic layer was dried over MgSO$_4$, filtered and evaporated. Final purification was achieved by silica gel chromatography. The typical yields for the product formation varied between 60 and 90%.

Standard Operating Procedure 35: Introduction of an Alloc-Group

A solution of starting material (2 mmol), dry pyridine (5 mmol) and dry THF (5 mL) was cooled to 0° C. Subsequently, Allylchloroformate (2.2 mmol) were added dropwise and stirring was continued until completion. The reaction mixture was diluted with dichloromethane and subsequently washed with 10% aqueous citric acid solution, saturated NaHCO$_3$ solution, water and saturated brine solution. The organic layer was dried over Na$_2$SO$_4$, filtered and evaporated. Final purification was achieved either by crystallization or by silica gel chromatography. The typical yields for the product formation varied between 80 and 95%.

Standard Operating Procedure 36: Cleavage of an Alloc-Group

A mixture of the Allyloxycarbonate (1.17 mmol), dimedone (1.33 mmol) and Pd(Ph$_3$P)$_4$ (0.30 mmol) was dissolved in dry THF (60 mL) and stirred under Ar atmosphere until completion of the reaction. The reaction mixture was concentrated in vacuo and purified by silica gel chromatography. The typical yields for the product formation varied between 78 and 97%.

Standard Operating Procedure 37: Lewis Acid Mediated Benzylation

To a stirred mixture of the starting material (1 mmol) and benzyl trichloroacetimidate in dry hexane/dichloromethane (10 mL, 2/1) was added Lewis acid (0.01-0.05 equiv., e.g. TMSOTf, TfOH) and stirring was continued at r.t. until completion. The reaction was quenched with triethyl amine and concentrated. Final purification was achieved by silica gel chromatography. The typical yields for the product formation varied between 50 and 92%.

Standard Operating Procedure 38: Benzylation Under Mild Basic Conditions

The starting material (3.49 mmol) was dissolved in dry DMSO (20 mL) and cooled to 0° C. To the stirred solution were added successively benzyl bromide (3.5 equiv./OH-group), barium oxide (1.5 equiv/OH-group), catalytic amounts of TBAI (0.05 eqiv./OH-group) and potassium hydroxide (3.5 equiv./OH-group). Stirring was continued from 0° C. to r.t. until completion. The reaction was quenched with methanol, and further stirred for 30 min. After dilution with ether, the organic layer was washed with water and brine solution, dried over MgSO$_4$ and concentrated in vacuo. Final purification was achieved by silica gel chromatography.

Standard Operating Procedure 39: Ester Cleavage Under Aqueous Conditions

The starting material (0.3 mmol ester groups) was dissolved in 11.8 mL of a mixture of water and THF (3:7), cooled to 0° C. and reacted with 1 M aqueous NaOH-solution (5.0 mL). Stirring was continued until completion and the reaction mixture titurated with 10% aqueous HCl-solution to a pH of 9.5. After evaporation of the THF, the mixture was freeze dried and the remaining residue purified by silica gel chromatography to yield the product. The typical yields for the product formation varied between 85 and 95%.

Example 1

Synthesis of Building Blocks A-1 and A-2 from N-Acetyl Glucosamine

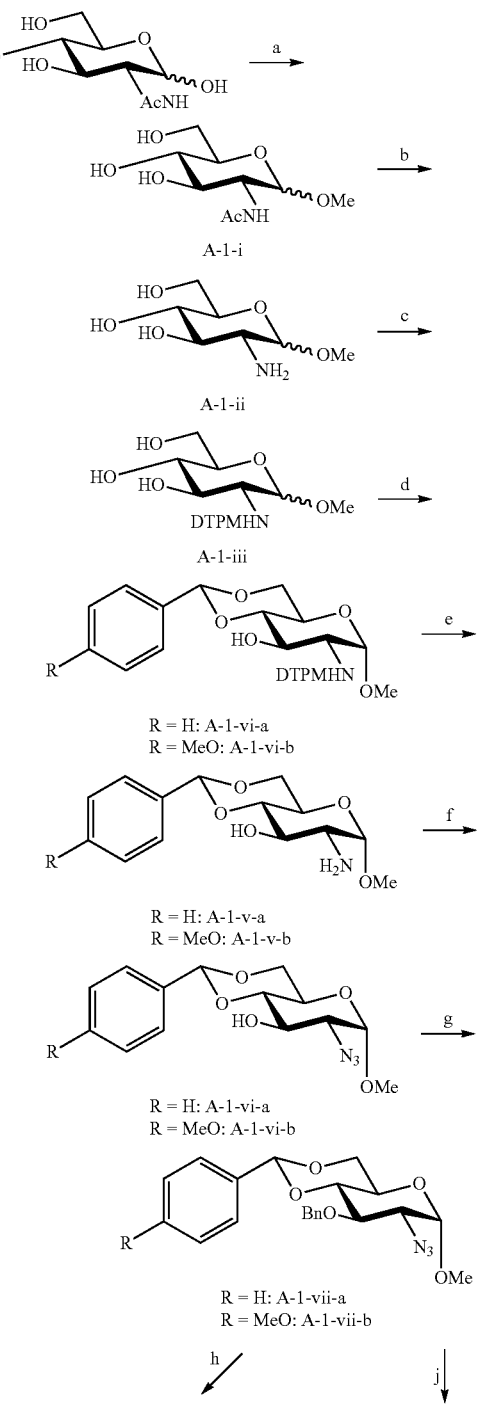

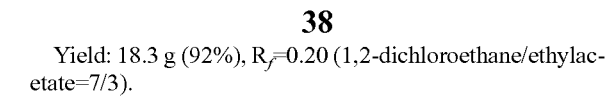

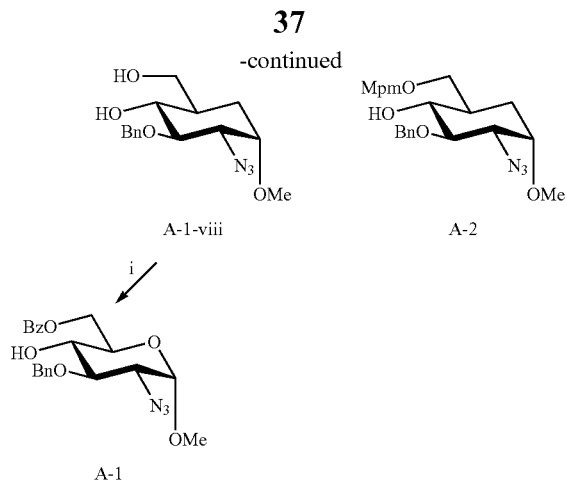

Example 1: Synthesis of building blocks A-1 and A-2 from N-Acetyl glucosamine, yields are reported for R=H, conditions; a) Amberlite IR 120 (ion exchange resin) (H⁺), MeOH, 60° C., (70%); b) 1 M NaOH, 120° C.; c) 1. SOP 10; 2. Ac₂O, pyridine; 3. NaOMe, MeOH (70%, 4 steps); d) SOP 1 (91% for R=H) or SOP 2 for R=Ome; e) SOP 11, (95%); f) SOP 12, (85%, 2 steps); g) SOP 7, (91%); h) SOP 4, (91%); i) SOP 17, (82%); j) SOP 5.

Preparation of A-1-i:

N-Acetyl-2-deoxy-α/β-D-glucopyranoside (8.5 g, 38.4 mmol) was suspended in 100 mL dry methanol. Subsequently, 12.0 g Amberlite IR 120 iron exchange resin (H⁺-form) was added and the reaction mixture refluxed for 70 hrs at 65° C. After cooling to 25° C., the iron exchange resin was removed by filtration and several times extracted with methanol. The combined methanol layers were neutralized with triethyl amine and concentrated in vacuo. The crude residue was purified by crystallization to furnish the title compound in 70% yield (α/β-mixture).

Preparation of A-1-iii:

Methyl glycoside A-1-I (20.6 mmol) was suspended in 100 mL aqueous NaOH solution (1 M) and stirred under reflux at 120° C. until completion. After cooling and neutralization with 10% aqueous HCl, the mixture was concentrated in vacuo and crude A-1-ii suspended in 200 mL methanol and reacted with N-[(1,3-dimethyl-2,4,6 (1H,3H,5H)-trioxopyrimidin-5-ylidene) methyl]-N',N"-dimethylamine (23.6 mmol) at 50° C. (pH 9.0) until completion. After evaporation and drying, crude A-1-iii was reacted with 150 mL acetylation mixture (pyridine/Ac₂O, 2/1, v/v) until completion, concentrated in vacuo, coevaporated with toluene and dried. The residue was suspended in ethyl acetate and extracted with water, 10% aqueous HCl, saturated, aqueous NaHCO₃ solution and H₂O, dried over Na₂SO₄ and concentrated. The crude residue was dissolved in dry methanol and reacted with a catalytic amount of NaOMe. After completion, the reaction was neutralized with Amberlite IR 120 and filtered. The organic layer was evaporated and dried to furnish the title compound A-1-iii in 70% yield (over 4 steps).

Preparation of A-1-iv-a:

Methyl-2-deoxy-2-N-[1-(1,3-dimethyl-2,4,6(1H,3H,5H)-trioxopyrimidin-5-ylidene) methyl]-α-D-glucopyranoside A-1-iii (16.0 g, 44.5 mmol) in acetonitrile (200 mL) was reacted with benzaldehyde dimethyl acetal (14.0 mL, 92.3 mmol) and a catalytic amount of p-toluenesulphonic acid monohydrate. After 2 hours at 55° C., the mixture was neutralized and evaporated. The remaining residue was extracted, washed and evaporated.

Yield: 18.3 g (92%), $R_f$=0.20 (1,2-dichloroethane/ethylacetate=7/3).

Preparation of A-1-v-a:

Methyl-4,6-O-benzylidene-2-deoxy-2-N-[1-(1,3-dimethyl-2,4,6(1H, 3H, 5H)-trioxopyrimidin-5-ylidene) methyl]-α-D-glucopyranoside A-1-iv-a (18.30 g, 40.90 mmol) in DMF (50 mL) was reacted with ethylenediamine (20 mL) at room temperature. After stirring for 35 minutes, the mixture was concentrated. Yield: 10.90 g (94.7%), $R_f$=0.18 (chloroform/methanol=9/1).

Preparation of A-1-vi-a:

To a solution of methyl-2-amino-4,6-O-benzylidene-2-deoxy-α-D-glucopyranoside (7.5 g, 26.7 mmol) and 4-N,N'-(dimethylamino)pyridine (14.5 g) in acetonitrile (100 mL) was added TfN₃-solution (85 mL) at room temperature. The reaction mixture was concentrated and the residue was purified by filtration through a short silica gel pad.

Yield: 7.00 g (85.3%), $R_f$=0.18 (chloroform/methanol=9/1).

Preparation of A-1-vii-a:

Methyl 2-azido-2-deoxy-4,6-benzylidene-α-D-glucopyranoside A-1-vii-a (10.87 g, 35.40 mmol) in N,N'-dimethylformamide (50 mL) was reacted with NaH (95%, 0.92 g, 36.4 mmol) and benzyl bromide (5.47 mL, 45.9 mmol). After completion, the excess of NaH was quenched, followed by concentration. The residue was extracted, washed and concentrated.

Yield: 12.93 g (92.0%), $R_f$=0.37 (petroleum spirit/ethyl acetate=3/1).

Preparation of A-1:

Methyl-2-azido-3-O-benzyl-2-deoxy-α-D-glucopyranoside (9.87 g, 31.9 mmol) in dichloromethane (50 mL) and pyridine (10 mL) was treated with benzoyl chloride (3.72 mL, 32.04 mmol) at −45° C. for 2 hours. The reaction was concentrated and the residue extracted, washed and evaporated.

Yield: 10.78 g (81.7%), $R_f$=0.31 (petroleum spirit/ethylacetate=1/1).

Compound A-1:

¹H-NMR (400 MHz, CDCl₃): δ=8.03 (d, 2H, Aryl), 7.57 (m, 1H, Aryl), 7.45-7.29 (m, 7H, Aryl), 4.93 (d, 1H, $J_{gem}$=10.8 Hz, OCH₂), 4.82 (d, 1H, $J_{gem}$=10.8 Hz, OCH₂), 4.81 (d, 1H, $J_{1,2}$=3.6 Hz, H-1α), 4.73 (dd, 1H, $J_{5,6a}$=4.4 Hz, $J_{gem}$=12.0 Hz, H-6a), 4.47 (dd, 1H, $J_{5,6b}$=2.0 Hz, H-6b), 3.85 (dd, 1H, $J_{3,4}$=8.8 Hz, H-3), 3.57 (ddd, 1H, $J_{4,5}$=10.0 Hz, H-4), 3.45 (s, 3H, Ome), 3.37 (dd, 1H, $J_{2,3}$=10.0 Hz, H-2), 2.80 (bs, 1H, 4-OH).

Example 2

Synthesis of Building Blocks A-3 and A-4

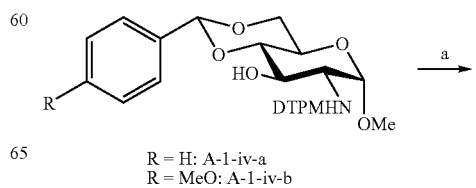

R = H: A-1-iv-a
R = MeO: A-1-iv-b

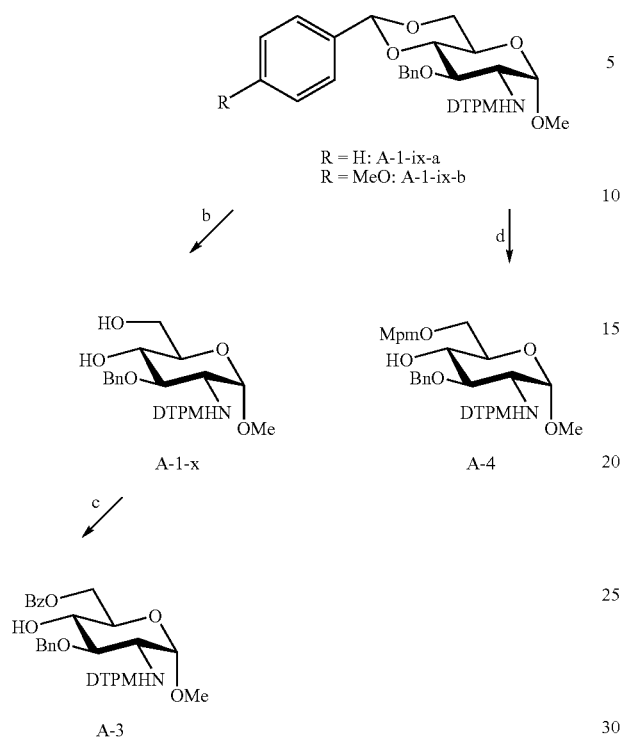
Example 2: Synthesis of building block A-3 and A-4, conditions: a) SOP 7, (72% for R=H); b) SOP 4, (82%); c) SOP 17, (84%); d) SOP 5.
Compound A-3:
$^1$H-NMR (400 MHz, CDCl$_3$): δ=10.16 (dd, 1H, J$_{NH,2}$=9.4 Hz, J$_{NH,=C-H}$=14.0 Hz, NH), 8.11 (d, 1H, =C—H), 7.68-7.22 (3m, 8H, Aryl), 4.84 (d, 1H, J$_{1,2}$=3.5 Hz, H-1α), 4.83 (dd, 1H, J$_{6a,6b}$=12.3 Hz, J$_{5,6a}$=3.5 Hz, H-6a), 4.73 (d, 1H, J$_{gem}$=11.7 Hz, OCH$_2$), 4.46 (dd, 1H, J$_{5,6b}$=2.1 Hz, H-6b), 3.91 (m, 1H, H-5), 3.72 (dd, 1H, J$_{3,4}$≈J$_{2,3}$=8.8 Hz, H-3), 3.57 (ddd, 1H, J$_{4,5}$=9.5 Hz, H-4), 3.48 (s, 3H, Ome), 3.38 (ddd, 1H, J$_{2,3}$=10.5 Hz, H-2), 3.32 (s, 3H, Nme), 3.31 (s, 3H, Nme), 3.05 (bs, 1H, 4-OH).
Example 3
Synthesis of L-ido Configured Glycosyl Donor B-1
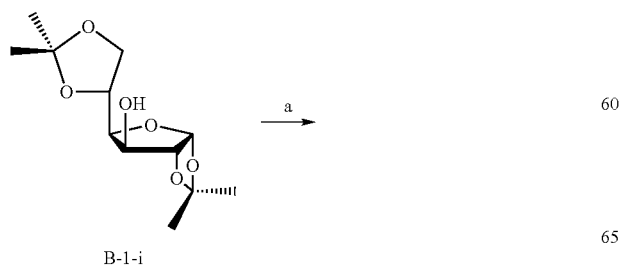
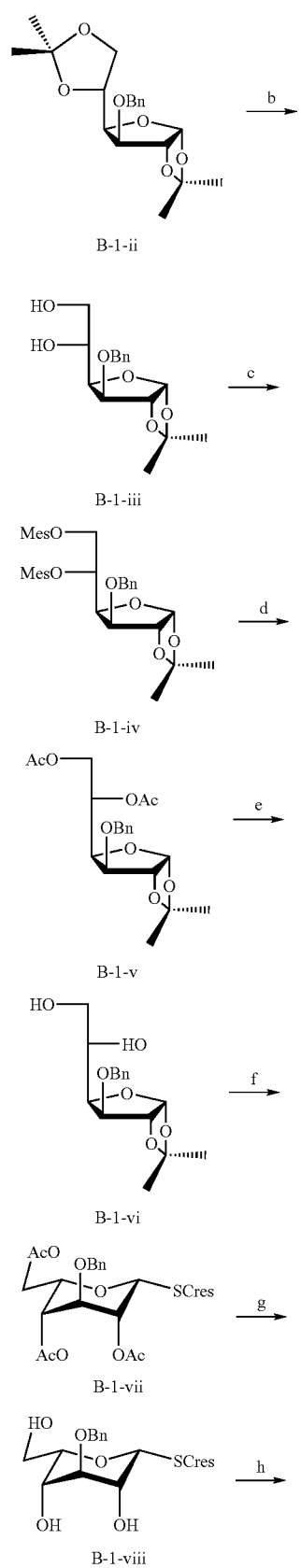

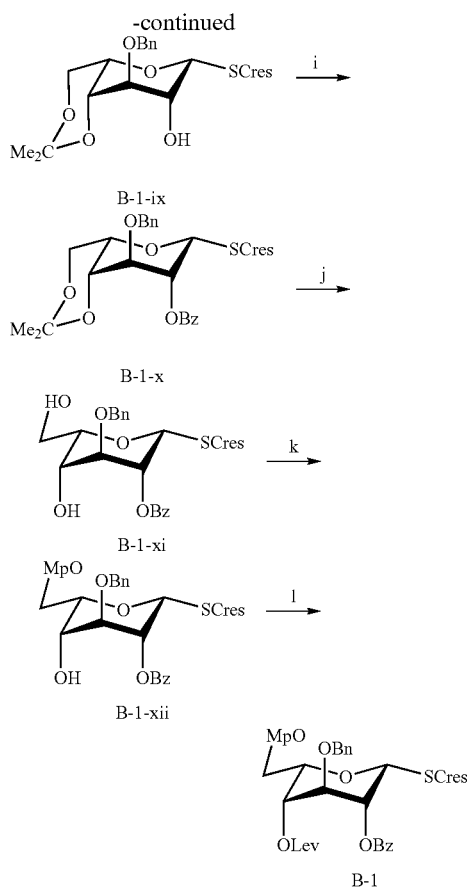

Example 3: Synthesis of Building Block B-1, conditions: a) SOP 7, (95%); b) 60% aqueous Acetic acid, 60° C. (90%); c) Methanesulfonyl chloride, Pyridine, 0° C.-RT (87%); d) Cesium Acetate, Ac$_2$O, 120° C. (95%); e) SOP 22, (92%); f) 1. 90% TFA, 0° C.; 2. Ac$_2$O, Pyridine; 3. SOP 31, (73%, 3 steps); g) SOP 22, (98%); h) SOP 3, (92%); I) SOP 18, (98%); j) 80% acetic acid, 100° C. (98%); k) SOP 26, (89%); l) SOP 23, (98%).

Preparation of B-1-iii:

B-1-ii (15.60 mmol) was dissolved in 60% aqueous acetic acid (50 mL) and stirred at 60° C. until completion. After neutralization with solid NaHCO$_3$, the mixture was evaporated and co evaporated with toluene. Crude B-1-iii was dissolved in CHCl$_3$/H$_2$O, the organic layer separated, dried over Na$_2$SO$_4$ and evaporated. The remaining residue was purified by a short silica gel chromatography to yield B-1-iii in 90% (4.36 g).

Preparation of B-1-iv:

17.72 mmol of B-1-iii was dissolved in 25 mL dry pyridine, to which mesyl chloride (methylsulfonyl chloride, 42.5 mmol) was added dropwise at 0° C. The mixture was stirred at 4° C. until completion and was subsequently poured into warm water (50° C., 90 mL), cooled and the precipitate isolated by filtration. B-1-iv was obtained after drying in 87% yield (7.19 g).

Preparation of B-1-v:

B-1-iv (6.43 mmol) and cesium acetate (64.3 mmol) were suspended in 25 mL acetic anhydride and refluxed at 125° C. until completion. The reaction mixture was concentrated in vacuo, co evaporated with toluene and the residue extracted from ethyl acetate/H$_2$O (1/1). The organic layer was collected and washed with saturated aqueous NaHCO$_3$ solution and saturated brine solution, dried over Na$_2$SO$_4$ and evaporated. Purification was achieved by silica gel chromatography. Yield: 2.68 g (95%).

Preparation of B-1-vii:

B-1-vi (5.61 mmol) was dissolved in aqueous TFA (90%, 15 mL) and further stirred at 0° C. until completion. The reaction mixture was neutralized with aqueous NaOH solution at 0° C., concentrated in vacuo and dried. The residue was suspended in 90 mL acetylation mixture (pyridine/acetic anhydride=2/1) and 50 mL dichloromethane at 0° C. and further stirred until completion. After concentration in vacuo and co evaporation with toluene, the residue was dissolved in ethyl acetate/H$_2$O (1/1), the organic layer collected and washed with 10% aqueous citric acid solution, saturated aqueous NaHCO$_3$ solution and brine solution, dried over Na$_2$SO$_4$ and evaporated. The crude residue and p-thiocresol (6.0 mmol) were dissolved in 40 mL anhydrous dichloromethane and cooled to 0° C., reacted with BF$_3$×OEt$_2$ (8.41 mmol) and further stirred at r.t. until completion. The reaction was stopped with saturated NaHCO$_3$ solution and the organic layer was washed with water, dried over Na$_2$SO$_4$ and evaporated. Final purification was achieved by silica gel chromatography to yield B-1-vii in 73% over 3 steps.

Preparation of B-1-xi:

B-1-x (8.0 mmol) was dissolved in 80% aqueous AcOH and heated at 100° C. until completion. The mixture was cooled to r.t., neutralized with solid NaHCO$_3$ and dissolved in ethyl acetate/water (1/1). After removal of the aqueous layer, the organic layer was dried over MgSO$_4$ and evaporated to dryness furnishing B-1-xi in 98% yield.

Compound B-1:

$^1$H-NMR (400 MHz, CDCl$_3$): δ=8.07 (d, 2H, Aryl), 7.57-7.30 (m, 10H, Aryl), 7.10 (d, 2H, Aryl), 6.88-6.81 (m, 4H, Mp), 5.55 (d, 1H, J$_{1,2}$<1.5 Hz, H-1β), 5.45 (m, 1H, H-2), 5.26 (ddd, 1H, H-5), 5.13 (m, 1H, H-4), 4.91 (d, 1H, J$_{gem}$=12.1 Hz, OCH$_2$), 4.78 (d, 1H, J$_{gem}$=12.1 Hz, OCH$_2$), 4.16 (dd, 1H, J$_{gem}$=9.6 Hz, J$_{5,6a}$=7.6 Hz, H-6a), 4.08 (dd, 1H, J$_{5,6b}$=5.2 Hz, H-6b), 3.93 (m, 1H, H-3), 3.77 (s, 3H, OCH$_3$), 2.58-2.36 (m, 4H, (CH$_2$)$_2$ Lev), 2.32 (s, 3H, SCH$_3$), 2.05 (s, 3H, CH$_3$C=O).

Example 4

Synthesis of L-ido Configured Gilycosyl Donor B-2

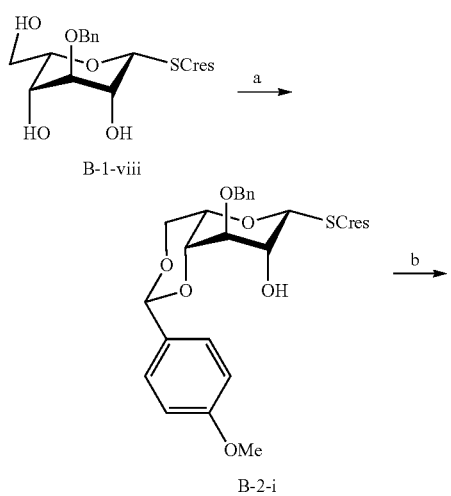

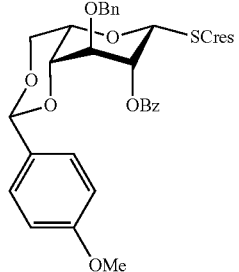
B-2-ii
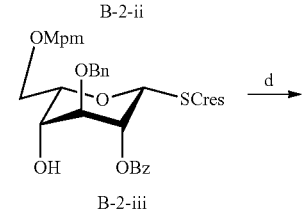
B-2-iii
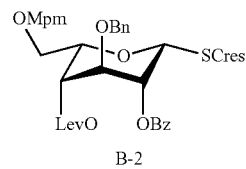
B-2
Example 4: Synthesis of L-ido Configured Glycosyl Donor B-2; a) SOP 2; b) SOP 18; c) SOP 5; d) SOP 23.
Example 5
Synthesis of Building Block C-1, C-1a and C-1b
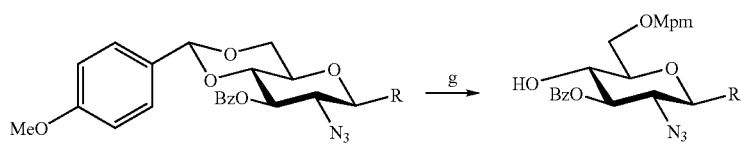
C-1a-iii: R = SMe
C-1b-iii: R = SCres
C-1a: R = SMe
C-1b: R = SCres
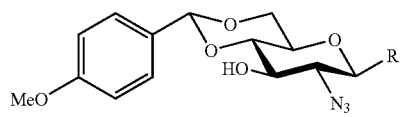
C-1a-ii: R = SMe
C-1b-ii: R = SCres
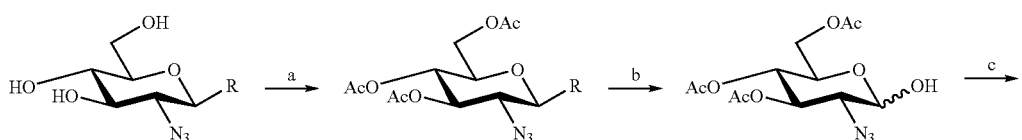
C-1-i-a: R = SMe
C-1-i-b: R = SCres
C-1-ii-a: R = SMe
C-1-ii-b: R = SCres
C-1-iii
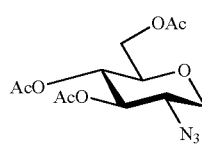
C-1-iv
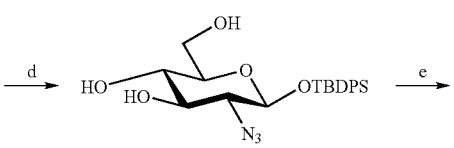
C-1-v
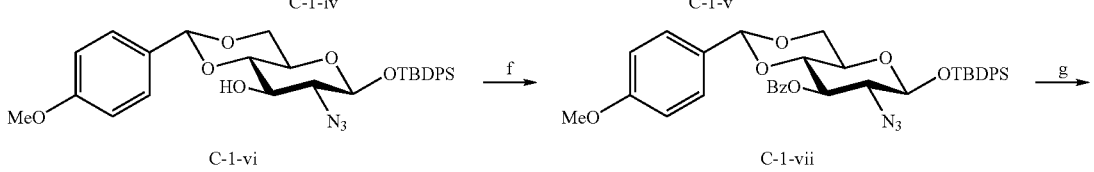
C-1-vi
C-1-vii

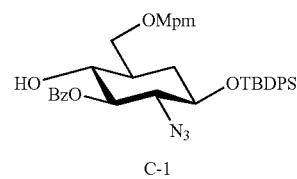

C-1

Example 5: Synthesis of Building Blocks C-1, C-1a and C-1b, conditions: a) SOP 19; b) SOP 13, (78%, 2 steps); c) SOP 8, (91%); d) SOP 22; e) SOP 2, (85%, 2 steps for C-1-vi); f) SOP 18; g) SOP 5, (75%, 2 steps for C-1).

Preparation of C-1-iia:

To methyl 2-azido-2-deoxy-1-thio-β-D-glucopyranoside. (10 g, 42.50 mmol) in pyridine (50 mL) at 0° C. was added acetic anhydride (20 g) and the reaction stirred for 1 hour. The reaction mixture was evaporated to dryness and the residue extracted to give the title triacetate (15.23 g, quantitative,), $R_f$=0.7 (CHCl$_3$/Petroleum ethers, 1:1).

Preparation of C-1-iii:

To a solution of methyl 3,4,6-tri-O-acetyl-2-azido-2-deoxy-1-thio-β-D-glucopyranoside (14.1 g, 39 mmol) in wet acetone (200 mL) was added NBS (3 equiv.). The resulting mixture was allowed to stir for 2 h. The mixture was then quenched, concentrated and the residue purified by silica gel chromatography to give the title hemiacetal as an oil (10.1 g, 78%), $R_f$=0.5 (EtOAc/Petroleum ether, 1:1).

Preparation of C-1-vi:

A mixture of 2-azido-2-deoxy-β-D-glucopyranosyl tert-butyldiphenylsilane (5.5 g, 12.42 mmol), 4-methoxybenzaldehyde dimethylacetal (4.4 g, 24 mmol), and 4-toluenesulphonic acid (100 mg) in acetonitrile/DMF (200 mL, 5:3) were heated at 60° C. for 1 hour. The reaction mixture was then neutralized and evaporated to give the crude compound as an oil. The residue was purified by silica chromatography to give the product (6.7 g, 96%, 85% from C-1-iv); $R_f$=0.8 (dichloromethane/Petroleum ethers; 10:2).

Preparation of C-1-vii:

A mixture of DMAP (1.63 g, 13.2 mmol) and benzoyl chloride (1.7 g, 12.1 mmol) and 2-azido-2-deoxy-4,6-O-(4-methoxybenzylidene)-β-D-glucopyranosyl tert-butyldiphenylsilane (6.7 g, 11.9 mmol) in 1,2-dichloroethane (100 mL) was stirred at 60° C. for 1 h. The reaction mixture was quenched, extracted, washed and concentrated to give a crude residue. The residue was passed through a plug of silica to give the product (5.5 g, 69%); $R_f$=0.7 (dichloromethane/Petroleum ethers; 4:1).

Preparation of C-1:

To a mixture of 2-azido-2-deoxy-3-O-benzoyl-4,6-O-(4-methoxybenzylidene)-β-D-glucopyranosyl tert-butyldiphenylsilane (10 g, 15 mmol), sodiumcyanoborohydride (5 g, 75.6 mmol) and molecular sieves in DMF (200 mL) at 0° C. was added trifluoroacetic acid (28 g, 247 mmol) at 0° C. and then left to run overnight at r.t. The reaction mixture was quenched, filtered and concentrated and the residue purified by column chromatography to give the title compound (7.0 g, 70%), $R_f$=0.4 (ethylacetate/petroleum ethers, 3:7).

Compound C-1:

$^1$H-NMR (400 MHz, CDCl$_3$): δ=8.08 (d, 2H, Aryl), 7.72 (m, 4H, Aryl), 7.59 (m, 1H, Aryl), 7.47 (m, 3H, Aryl), 7.42 (m, 2H, Aryl), 7.34 (m, 3H, Aryl), 7.13 (d, 2H, Mpm) 6.83 (d, 2H, Mpm), 4.96 (dd, 1H, $J_{2,3}$≈$J_{3,4}$=9.7 Hz, H-3), 4.53 (d, 1H, $J_{1,2}$=7.6 Hz, H-1β), 4.37 (2d, 2H, OCH$_2$), 3.83 (ddd, 1H, H-4), 3.79 (s, 3H, OCH$_3$), 3.65 (dd, 1H, H-2), 3.53 (dd, 1H, $J_{gem}$=10.8 Hz, $J_{5,6a}$=4.1 Hz, H-6a), 3.46 (dd, 1H, $J_{5,6b}$=4.1 Hz, H-6b), 3.12 (m, 1H, H-5), 3.02 (d, 1H, $J_{4,OH}$=3.5 Hz, 4-OH), 1.12 (s, 9H, C(CH$_3$)$_3$).

Example 6

Synthesis of Building Block C-2

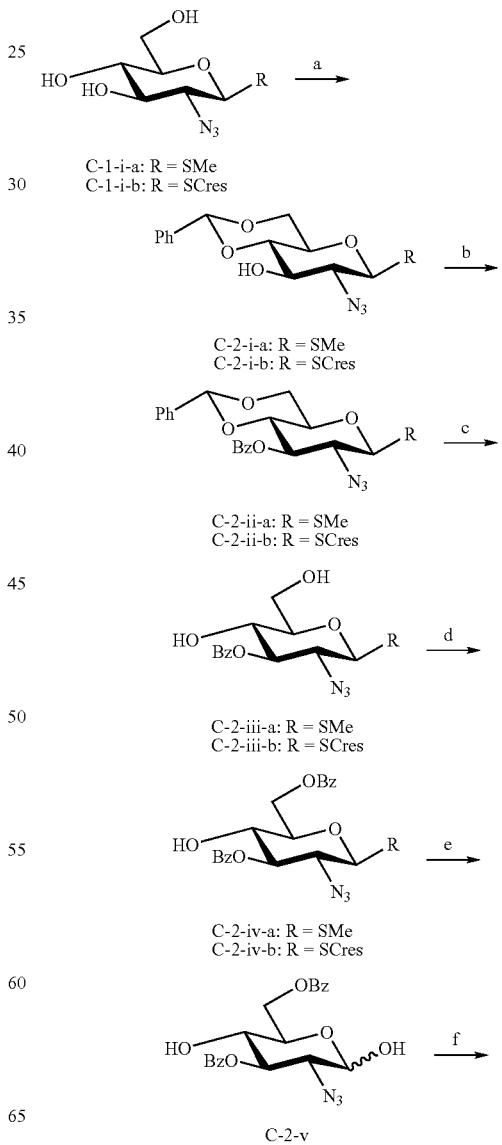

47

-continued

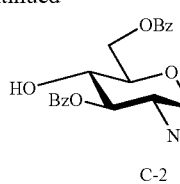

C-2

Example 6: Synthesis of Building Block C-2, conditions: a) SOP 1, (90% for R=SMe); b) SOP 18, (87% for R=SMe); c) SOP 4, p-TosOH, MeOH, CH$_3$CN (86% for R=SMe); d) SOP 17, (92% for R=SMe); e) SOP 13, (94%); f) SOP 8, (82%).

Compound C-2:

$^1$H-NMR (400 MHz, CDCl$_3$): δ=8.09 (d, 2H, Aryl), 7.97 (d, 2H, Aryl), 7.72 (m, 4H, Aryl), 7.60 (m, 1H, Aryl), 7.50-7.27 (m, 11H, Aryl), 4.98 (dd, 1H, $J_{2,3}$≈$J_{3,4}$=9.7 Hz, H-3), 4.58 (d, 1H, $J_{1,2}$=7.8 Hz, H-1β), 4.51 (dd, 1H, $J_{gem}$=11.3 Hz, $J_{5,6a}$=4.7 Hz, H-6a), 4.36 (dd, 1H, $J_{5,6b}$=2.2 Hz, H-6b), 3.72-3.68 (m, 2H, H-2, H-4), 3.31 (m, 1H, H-5), 3.23 (d, 1H, $J_{4,OH}$=4.5 Hz, 4-OH), 1.13 (s, 9H, C(CH$_3$)$_3$).

Example 7

Synthesis of Several Carbamoylated Building Blocks C-3a to C-3d and C-4a to C-4-d, Containing a 6-O benzoyl or 6-O-p-methoxybenzyl Protection

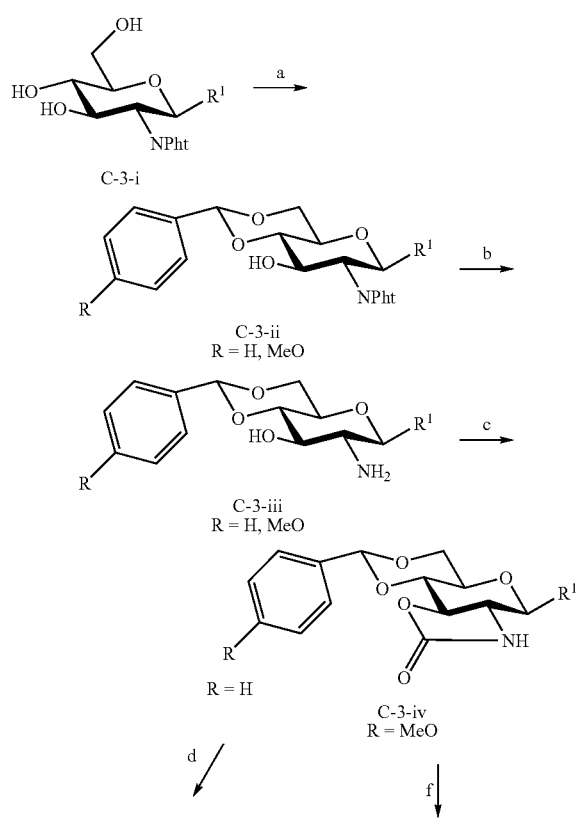

48

-continued

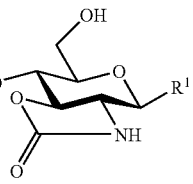

C-3-v

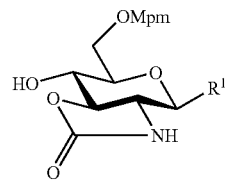

C-4a: R$^1$ = SCres
C-4b: R$^1$ = SEt
C-4c: R$^1$ = OTBDPS
C-4d: R$^1$ = SMe

C-3a: R$^1$ = SCres
C-3b: R$^1$ = SEt
C-3c: R$^1$ = OTBDPS
C-3d: R$^1$ = SMe

Example 7: Synthesis of several carbamoylated building blocks C-3a to C-3d and C-4a to C-4-d, containing a 6-O-benzoyl or 6-O-p-methoxybenzyl protection, conditions: a) R=MeO: SOP 2; R=H: SOP 1, (82%, R$^1$=SCres, R=H); b) SOP 30, (87%, R$^1$=SCres, R=H); c) SOP 29, (95%, R$^1$=SCres, R=H); d) SOP 4, (72%, R$^1$=SCres); e) SOP 17, (85%); f) SOP 5.

Compound C-3a:

$^1$H-NMR (400 MHz, CDCl$_3$): δ=8.06 (d, 2H, Aryl), 7.62 (m, 1H, Aryl), 7.48 (t, 2H, Aryl), 7.38 (d, 2H, Aryl), 6.97 (d, 2H, Aryl), 5.06 (bs, 1H, NH), 4.79 (dd, 1H, $J_{gem}$=12.0 Hz, $J_{5,6a}$=3.6 Hz, H-6a), 4.70 (d, 1H, $J_{1,2}$=9.2 Hz, H-1β), 4.63 (dd, 1H, $J_{5,6b}$=2.0 Hz, H-6b), 4.18 (dd, 1H, $J_{2,3}$ $J_{3,4}$=10.4 Hz, H-3), 3.89 (dd, 1H, $J_{4,5}$=9.2 Hz, H-4), 3.72 (m, 1H, H-5), 3.23 (ddd, 1H, H-2), 3.12 (bs, 1H, 4-OH), 2.29 (s, 3H, SCH$_3$).

Example 8

Synthesis of Several 6-Omp and Cyclic 2,3-carbamoyl Protected Building Blocks C-5a to C-5c

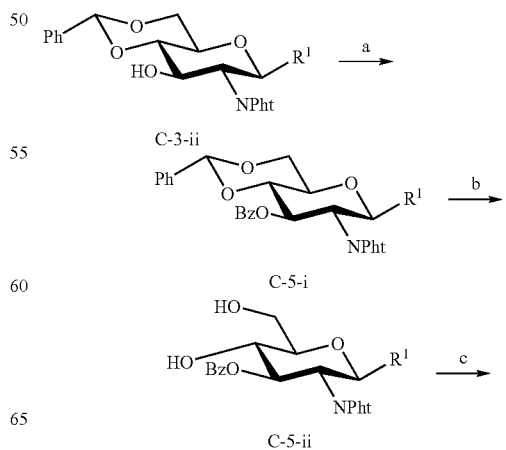

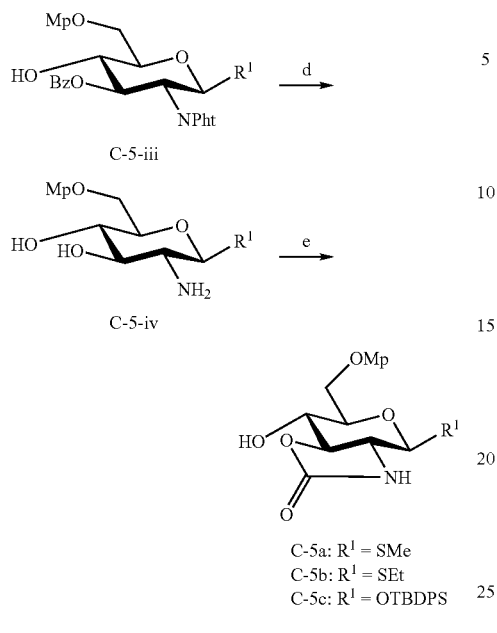

C-5-iii

C-5-iv

C-5a: R¹ = SMe
C-5b: R¹ = SEt
C-5c: R¹ = OTBDPS

Example 8: Synthesis of several 6-OMp and cyclic 2,3-carbamoyl protected building blocks C-5a to C-5c, conditions: a) SOP 18, (92% for R¹=OTBDPS); b) SOP 4, (82%); c) SOP 26, (75% for R¹=OTBDPS); d) SOP 30, (87%); e) SOP 29, (95%).

Compound C-5c:

$^1$H-NMR (400 MHz, CDCl$_3$): δ=7.69 (m, 2H, Aryl), 7.63 (m, 2H, Aryl), 7.46-7.31 (m, 6H, Aryl), 6.82 (bs, 4H, Mp), 5.04 (bs, 1H, NH), 4.78 (d, 1H, $J_{1,2}$=7.6 Hz, H-1β), 4.15-4.10 (m, 3H, H's not assigned), 3.97 (dd, 1H, J=11.6 Hz, J=9.6 Hz, H not assigned), 3.78 (s, 3H, OMe), 3.56 (m, 1H, H not assigned), 3.48 (m, 1H, H not assigned), 2.80 (bs, 1H, 4-OH), 1.08 (s, 9H, C—(CH$_3$)$_3$).

Example 9

Synthesis of Building Blocks C-6-a and C-6-b and C-7

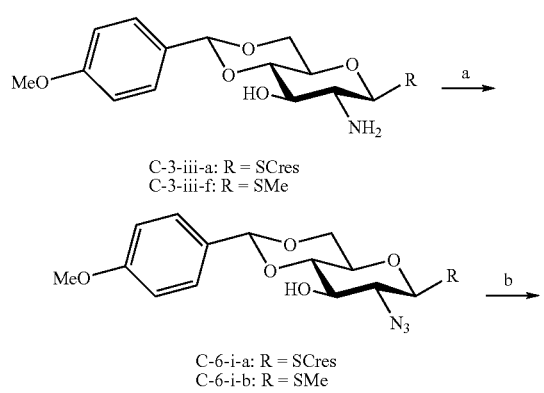

C-3-iii-a: R = SCres
C-3-iii-f: R = SMe

C-6-i-a: R = SCres
C-6-i-b: R = SMe

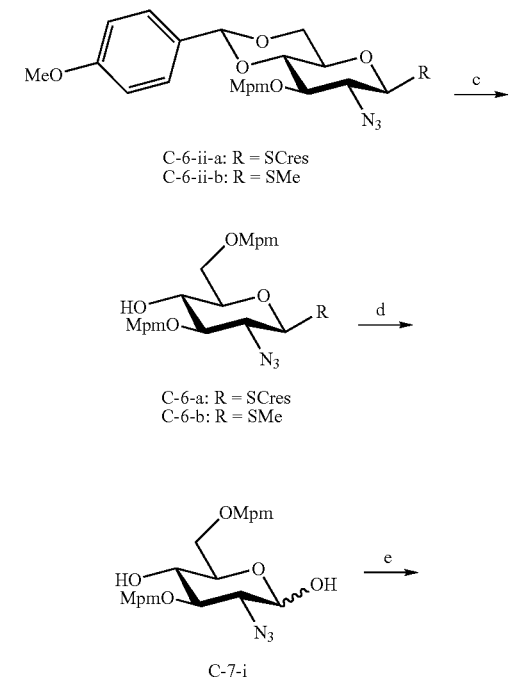

C-6-ii-a: R = SCres
C-6-ii-b: R = SMe

C-6-a: R = SCres
C-6-b: R = SMe

C-7-i

C-7

Example 9: Synthesis of building blocks C-6-a, C-6-b and C-7, conditions; a) SOP 12, (83%); b) SOP 7; c) SOP 5, (75%, 2 steps); d) SOP 14 (82%); e) SOP 8 (91%).

Compound C-6-a:

$^1$H-NMR (400 MHz, CDCl$_3$): δ=7.43 (d, 2H, Aryl), 7.25 (m, 4H, Aryl), 7.08 (d, 2H, Aryl), 6.88 (m, 4H, Aryl), 4.81 (d, 1H, $J_{gem}$=10.8 Hz, OCH$_2$), 4.74 (d, 1H, $J_{gem}$=10.8 Hz, OCH$_2$), 4.53 (d, 1H, $J_{gem}$=11.1 Hz, OCH$_2$), 4.48 (d, 1H, $J_{gem}$=10.8 Hz, OCH$_2$), 4.35 (d, 1H, $J_{1,2}$=10.0 Hz, H-1β), 3.82 (s, 3H, OCH$_3$), 3.79 (s, 3H, OCH$_3$), 3.76 (dd, 1H, $J_{gem}$=10.5 Hz, $J_{5,6a}$=5.4 Hz, H-6a), 3.70 (dd, 1H, $J_{5,6b}$=5.4 Hz, H-6b), 3.56 (ddd, 1H, H-4), 3.42 (m, 1H, H-5), 3.34 (dd, 1H, $J_{3,4}$=8.8 Hz, H-3), 3.24 (dd, 1H, $J_{2,3}$=9.4 Hz, H-2), 2.72 (d, 1H, $J_{4,OH}$=3.5 Hz, 4-OH), 2.38 (s, 3H, SCH$_3$).

Compound C-7:

$^1$H-NMR (400 MHz, CDCl$_3$): 7.63 (d, 4H, Aryl), 7.35-7.21 (m, 8H, Aryl), 7.08 (m, 2H, Aryl), 6.83-6.78 (m, 4H, Aryl), 4.72 (d, 1H, $J_{gem}$=11.0 Hz, OCH$_2$), 4.59 (d, 1H, $J_{gem}$=11.0 Hz, OCH$_2$), 4.29 (d, 1H, $J_{1,2}$=7.8 Hz, H-1β), 4.27 (d, 1H, $J_{gem}$=11.7 Hz, OCH$_2$), 4.21 (d, 1H, $J_{gem}$=11.7 Hz, OCH$_2$), 3.72 (s, 3H, OCH$_3$), 3.71 (s, 3H, OCH$_3$), 3.51 (ddd, 1H, $J_{3,4}$≈$J_{4,5}$=8.6 Hz, H-4), 3.40-3.32 (m, 3H, H-6a, H-6b, H-2), 3.05 (dd, 1H, $J_{2,3}$=9.8 Hz, H-3), 2.90 (m, 1H, H-5), 2.51 (d, 1H, $J_{4,OH}$=2.2 Hz, 4-OH), 1.12 (s, 9H, C(CH$_3$)$_3$).

Example 10

Synthesis of Building Block C-8a to C-8c

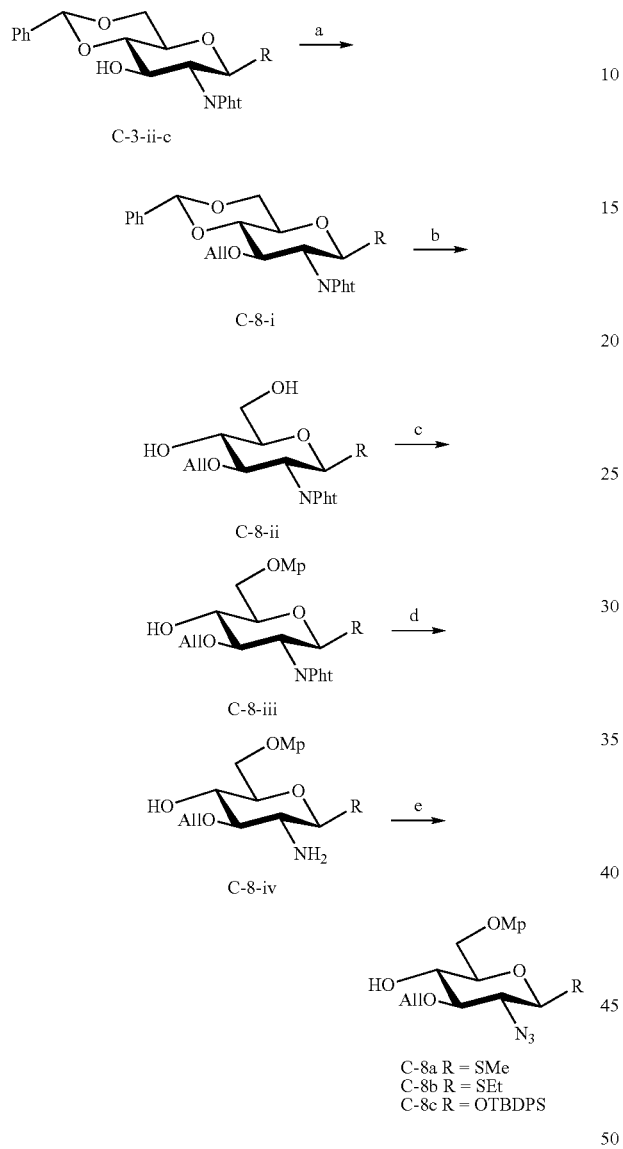

C-8a R = SMe
C-8b R = SEt
C-8c R = OTBDPS

Example 10: Synthesis of building blocks C-8a to C-8c, conditions: a) SOP 7, AllBr, DMF (65%, R=OTBDPS); b) SOP 4, (86%, R=OTBDPS); c) SOP 26, (70%, R=OTBDPS); d) SOP-30; e) SOP 12, (70%, 2 steps for R=OTBDPS).

Compound C-8c:

$^1$H-NMR (400 MHz, CDCl$_3$): δ=7.72 (m, 4H, Aryl), 7.43-7.16 (m, 6H, Aryl), 6.76 (m, 4H, Mp), 5.96 (m, 1H, =CH Allyl), 5.31 (m, 1H, =CH Allyl), 5.22 (m, 1H, =CH Allyl), 4.42 (d, 1H, J$_{1,2}$=7.6 Hz, H-1β), 4.39 (m, 1H, OCH$_2$ Allyl), 4.23 (m, 1H, OCH$_2$ Allyl), 3.97 (dd, 1H, J$_{gem}$=10.0 Hz, J$_{5,6a}$=3.6 Hz, H-6a), 3.92 (dd, 1H, J$_{5,6b}$=5.2 Hz, H-6b), 3.77 (s, 3H, OCH$_3$), 3.66 (ddd, 1H, J$_{4,5}$≈J$_{3,4}$=9.4 Hz, H-4), 3.42 (dd, 1H, J=9.8 Hz and J=7.8 Hz, H not assigned), 3.22 (m, 1H, H-5), 3.09 (dd, 1H, J=8.4 Hz and J=9.6 Hz, H not assigned), 2.48 (d, 1H, J$_{4,OH}$=2.8 Hz, 4-OH), 1.12 (s, 9H, C(CH$_3$)$_3$).

Example 11

Synthesis of Building Block D-1

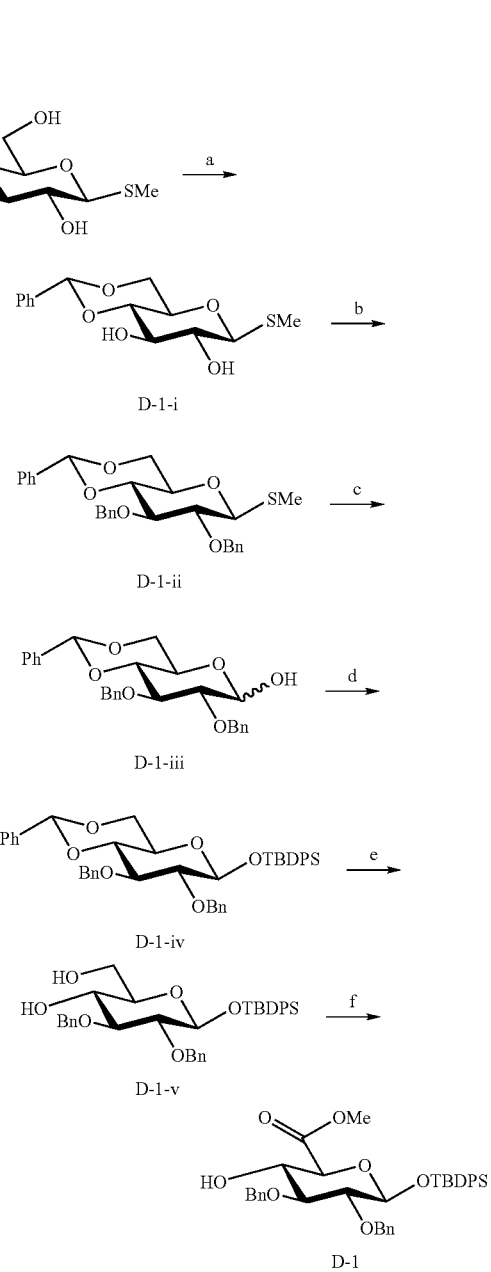

Example 11: Synthesis of building block D-1; a) SOP 1, (95%); b) SOP 7, (85%); c) SOP 13, (92%); d) SOP 8; e) SOP 4, (70%, 2 steps); f) 1. SOP 15; 2. SOP 16, (75%, 2 steps).

Compound D-1:

$^1$H-NMR (400 MHz, CDCl$_3$): δ=7.72 (m, 4H, Aryl), 7.41 (m, 2H, Aryl), 7.32-7.25 (m, 14H, Aryl), 5.04 (d, 1H, J$_{gem}$=11.0 Hz, OCH$_2$), 4.81 (m, 3H, OCH$_2$), 4.63 (d, 1H, J$_{1,2}$=7.4 Hz, H-1β), 3.88 (ddd, 1H, J$_{3,4}$≈J$_{4,5}$=9.2 Hz, H-4), 3.70 (s, 3H, OCH$_3$), 3.53 (dd, 1H, J=7.5 Hz, J=9.0 Hz, H not assigned), 3.47 (d, 1H, J$_{4,5}$=9.8 Hz, H-5), 3.42 (dd, 1H, J=8.9 Hz and J=8.9 Hz, H not assigned), 2.87 (d, 1H, J$_{4,OH}$=2.4 Hz, 4-OH), 1.11 (s, 9H, C(CH$_3$)$_3$).

Example 12

Synthesis of Building Block D-2a
2-O-Allyloxycarbonyl Protected Thioethyl Glycoside

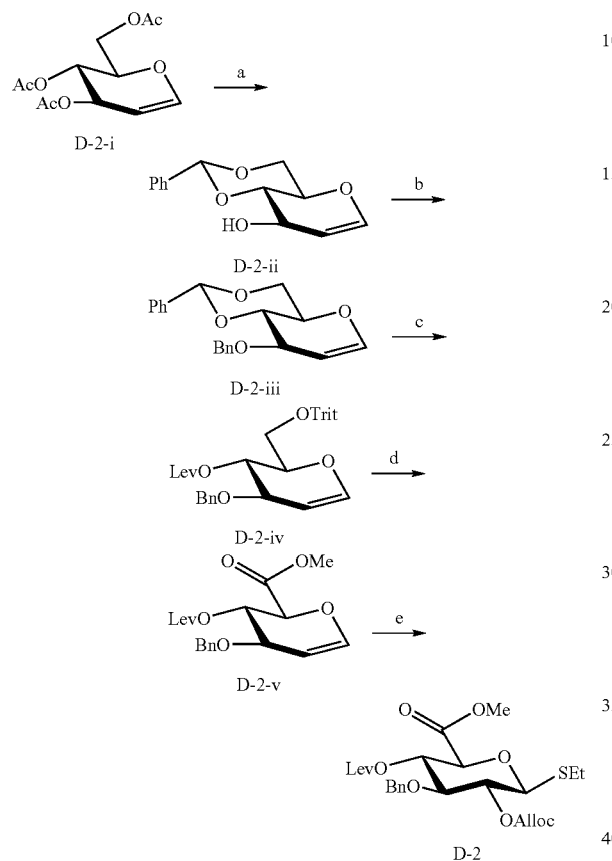

Example 12: Synthesis of Building Block D-2, conditions: a) 1. SOP 22; 2. SOP 1; b) SOP 7; c) 1. SOP 4; 2. TritCl, Pyridine, (ClCH$_2$)$_2$; 3. SOP 23; d) 1. CrO$_3$, H$_2$SO$_4$, Acetone, 0° C., 2. SOP 16; e) 1. Dimethyl dioxirane, Acetone; 2. EtSH, TFAA, CH$_2$Cl$_2$, 3. SOP 35.

Example 13

Synthesis of Building Block D-3

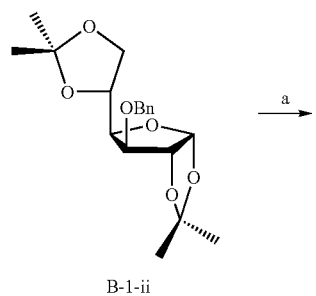

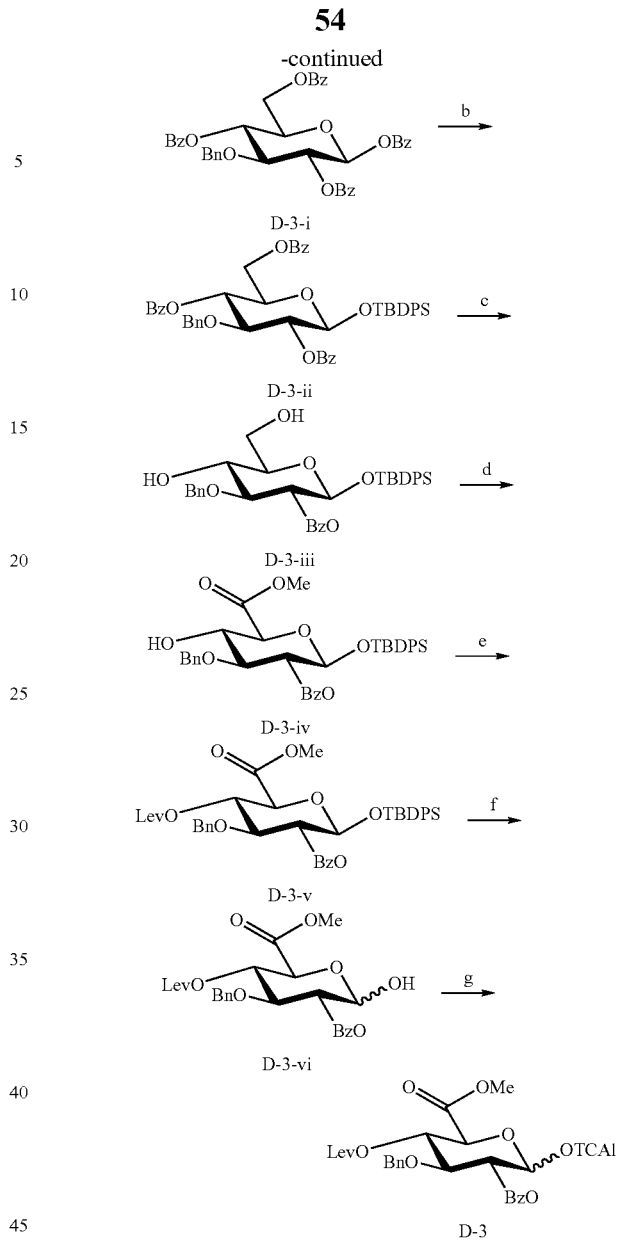

Example 13: Synthesis of Building Block D-3, conditions: a) 1. SOP 4, Amberlite IR 120, H$_2$O, 80° C.; 2. SOP 18, (85%, 2 steps) b) 1. SOP 21; 2. SOP 8, (70%, 2 steps); c) SOP 22, (96%); d) 1. SOP 15; 2. SOP 16, (80%, 2 steps); e) SOP 23, (92%); f) SOP 9, (95%); g) SOP 25a, (91%).

Preparation of D-3-I, Step 1:

The starting material (57 mmol) and Amberlite IR 120 iron exchange resin (H$^+$-form, 20 g) were suspended in water (180 mL) and stirred at 80° C. until completion. The iron exchange resin was removed by filtration and extracted with water. The combined aqueous layers were neutralized with triethyl amine and freeze dried.

Compound D-3-v:

$^1$H-NMR (400 MHz, CDCl$_3$): δ=7.95 (m, 2H, Aryl), 7.68 (m, 2H, Aryl), 7.58-7.12 (m, 16H, Aryl), 5.47 (dd, J$_{1,2}$=7.6 Hz, J$_{2,3}$=9.6 Hz, H-2), 5.31 (dd, J$_{3,4}$=9.6 Hz, H-4), 4.64 (d, 1H, 7.6 Hz, H-1β), 4.60 (d, 1H, J$_{gem}$=12.0 Hz, OCH$_2$), 4.55 (d, 1H, J$_{gem}$=12.0 Hz, OCH$_2$), 3.74 (dd, 1H, H-3), 3.70 (s, 3H, OCH$_3$), 3.63 (d, 1H, J$_{4,5}$=9.6 Hz, H-5), 2.68-2.16 (m, 4H, (CH$_2$)-Lev), 2.15 (s, 3H, CH$_3$), 0.96 (s, 9H, C(CH$_3$)$_3$).

Example 14

Syntheses of a Range of Block D Donor Sugars D-4 to D-7 from a Common Intermediate, a 4-O-levulinoyl Glucal

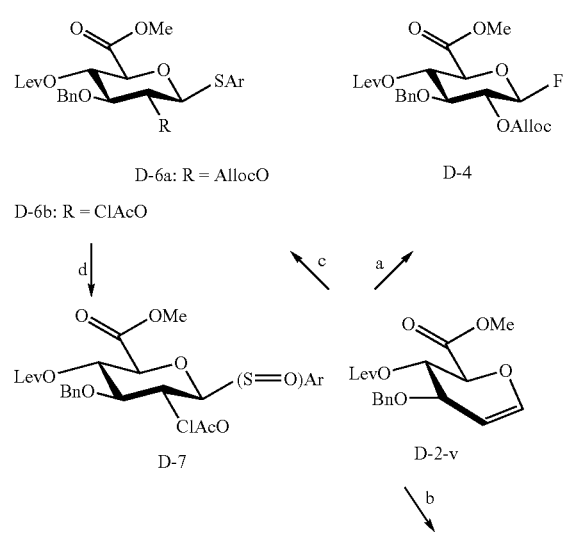

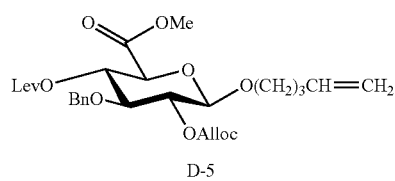

Example 14: Syntheses of D-4 to D-7 as donor sugars, conditions: a) 1. Dimethyl dioxirane, Acetone; 2. TBAF, THF; 3. SOP 35; b) 1. Dimethyl dioxirane, Acetone; 2. 4-penten-1-ol, ZnCl$_2$, CH$_2$Cl$_2$; 3. SOP 35; c) 1. Dimethyl dioxirane, Acetone; 2. ArSH, TFAA, CH$_2$Cl$_2$, (Ar=Ph, p-Tol); 3. SOP 35 or (ClAc)$_2$O, Pyridine, CH$_2$Cl$_2$ (for D-6b); d) MCPBA, CH$_2$Cl$_2$ (for D-6b as substrate).

Example 15

Synthesis of Building Block E-1 to E-4

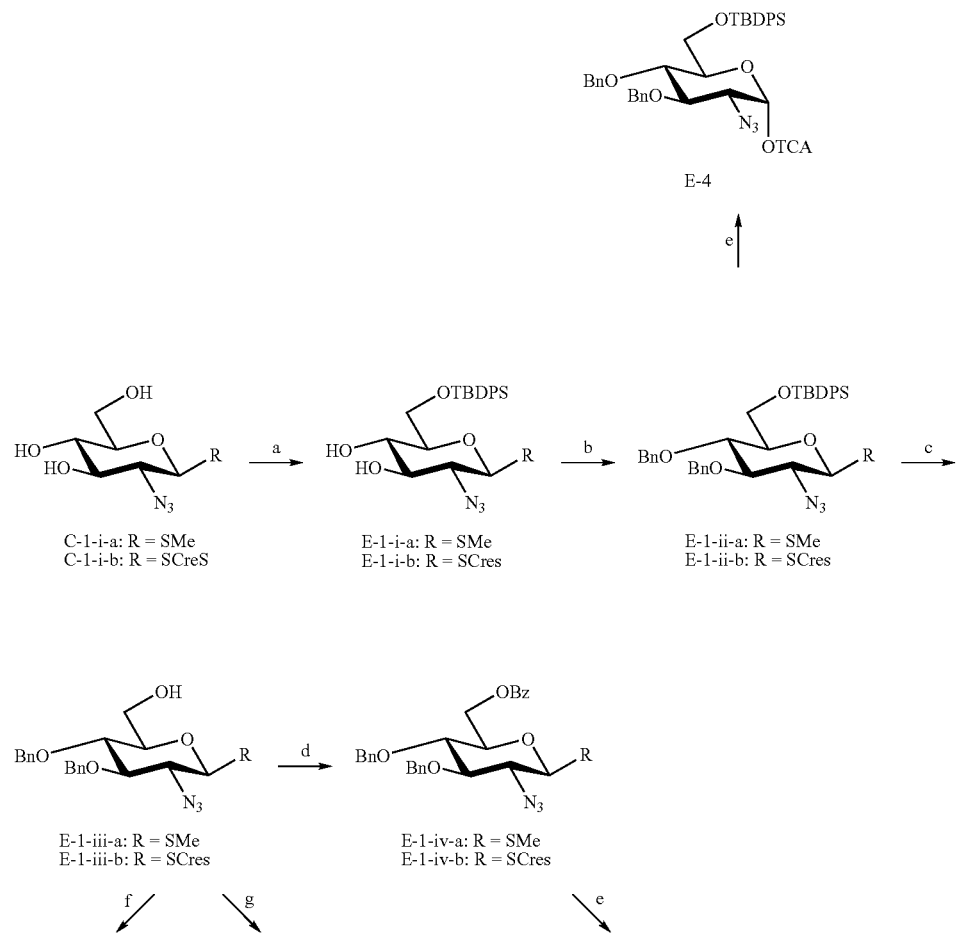

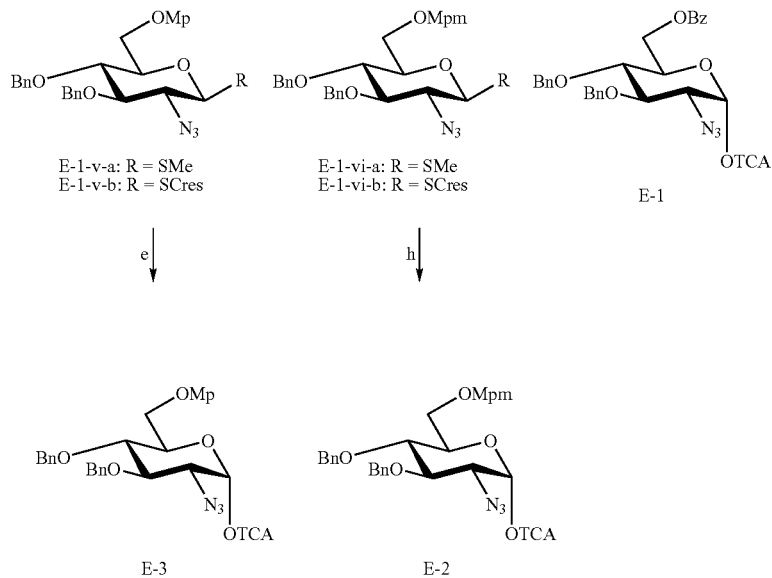

Example 15: Synthesis of Building Block E-1 to E-4, conditions: a) SOP 8; b) SOP 7; c) SOP 9, (84% over 3 steps, R=SMe); d) SOP 18, (82%, R=SMe); e) 1. SOP 13, (75%, for E-1-iv-a as starting material); 2. SOP 25b, (88%); f) 1. TosCl, Pyridine; 2. p-MeO—C$_6$H$_4$—O Na, NMP, 60° C.; g) SOP 7, (78%, R=SMe); h) 1. SOP 14; 2. SOP 25b, (79%, 2 steps, R=SMe).

Preparation of E-1-1-a:

A mixture of methyl 2-azido-2-deoxy-thio-β-D-glucopyranoside (10 g, 42.5 mmol) and imidazole (4.9 g, 71.25 mmol) in 20 mL DMF was treated with tert-butyldiphenylchlorosilane (11.6 mL, 44.63 mmol) for 2 h. The reaction mixture was concentrated, extracted, washed and dried. Yield: 23 g (crude light yellow syrup), R$_f$=0.74 (CHCl$_3$/methanol=9/1).

Preparation of E-1-ii-a:

The silyl ether from the previous step in 50 mL DMF, was treated with 2.68 g of 95% NaH (106.25 mmol) and 12.64 mL (106.25 mmol) of benzyl bromide at 0° C. After 1 h the excess NaH was quenched and the reaction concentrated, extracted, washed and concentrated to afford a yellow syrup yield: 28.5 g (crude yellow syrup), R$_f$=0.80 (hexane/ethyl acetate=7/3).

Preparation of E-1-iii-a:

The crude yellow syrup from the above reaction was treated with 36.5 mL AcOH and 106.3 mL (106.25 mmol) of 1 M solution of TBAF in THF overnight. The reaction was concentrated and purified by chromatography to afford the title compound. 14.9 g (84%, 3 steps) R$_f$=0.36 (petroleum spirit/ethyl acetate=7/3)

Preparation of E-1-iv-a:

Methyl 2-azido-2,3 di-O-benzyl-2-deoxy-thio-β-D-glucopyranoside (14.5 g, 34.9 mmol) in dichloromethane (200 mL) and anhydrous pyridine (8.6 mL, 106.2 mmol) was treated with benzoylchloride (4.93 mL, 42.5 mmol) at 0° C. for 1 hour. The reaction mixture was quenched, extracted, washed and evaporated. The residue was purified by silica gel column chromatography to afford the title compound as a white solid.

Yield: 14.9 g (82%), R$_f$=0.82 (Petroleum spirit/Ethyl acetate=7/3).

Preparation of E-1:

Methyl 2-azido-6-O-benzoyl-2,3-di-O-benzyl-2-deoxy-thio-β-D-glucopyranoside (8.68 g, 16.7 mmol) in acetone (50 mL) was treated with N-bromosuccinimide (8.92 g, 50.12 mmol) at 0° C. for 1 hour. The reaction mixture was then quenched, extracted, washed and evaporated, furnishing a yellow syrup which was purified by chromatography. Yield: 6.13 g (75%), R$_f$=0.57 (Petroleum spirit/Ethyl acetate=7/3). A cooled mixture of 2-azido-6-O-benzoyl-2,3 di-O-benzyl-2-deoxy-α/β-D-glucopyranose (5 g, 10.2 mmol), K$_2$CO$_3$ (7.0 g, 51 mmol) and trichloroacetonitrile (5.1 mL, 51 mmol) in 30 mL of dichloromethane was stirred for 2 h. The mixture was then filtered through celite and the filtrate was concentrated and purified on a short column of silica gel to obtain the title compound as an amorphous white solid.

Yield 5.69 g (88%), R$_f$=0.85 (Petroleum spirit/Ethyl acetate=7/3).

Compound E-1:

$^1$H-NMR (400 MHz, CDCl$_3$): δ=8.73 (s, 1H, C=NH), 8.00 (m, 2H, Aryl), 7.56 (m, 1H, Aryl), 7.43-7.25 (m, 12H, Aryl), 5.66 (d, 1H, J=8.4 Hz, H-1β), 4.95 (d, 1H, J$_{gem}$=10.8 Hz, OCH$_2$), 4.87 (d, 2H, J=10.8 Hz, OCH$_2$), 4.62 (d, 2H, J$_{gem}$=10.8 Hz, OCH$_2$), 4.58 (dd, 1H, J$_{gem}$=12.4 Hz, J$_{5,6a}$=2.0 Hz, H-6a), 4.46 (dd, 1H, J$_{5,6b}$=3.6 Hz, H-6b), 3.77-3.72 (m, 3H, H-5, 2H not assigned), 3.62 (dd, 1H, J=8.3 Hz, J=9.7 Hz, H not assigned).

Compound E-2:

$^1$H-NMR (400 MHz, CDCl$_3$): δ=8.70 (s, 1H, C=NH), 7.38-7.22 (m, 10H, Aryl), 7.13 (m, 2H, Aryl), 6.83 (d, 2H, Mpm), 6.44 (d, 1H, J$_{1,2}$=3.5 Hz, H-1α), 4.93 (d, 1H, J$_{gem}$=10.5 Hz, OCH$_2$), 4.89 (d, 1H, J$_{gem}$=10.5 Hz, OCH$_2$), 4.78 (d, 1H, J$_{gem}$=10.5 Hz, OCH$_2$), 4.57 (d, 1H, J$_{gem}$=11.7 Hz, OCH$_2$), 4.51 (d, 1H, J$_{gem}$=11.7 Hz, OCH$_2$), 4.39 (d, 1H, J$_{gem}$=11.7 Hz, OCH$_2$), 4.02 (dd, 1H, J$_{3,4}$≈J$_{2,3}$=9.5 Hz, H-3), 3.98 (m, 1H, H-5), 3.86 (dd, 1H, J$_{4,5}$=9.6 Hz, H-4), 3.76 (dd, 1H, H-2), 3.75 (s, 3H, OCH$_3$), 3.69 (dd, 1H, J$_{5,6a}$=3.5 Hz, J$_{gem}$=10.5 Hz, H-6a), 3.63 (dd, 1H, J$_{5,6b}$=1.8 Hz, H-6b).

Example 16

Synthesis of Building Blocks E-5 to E-8

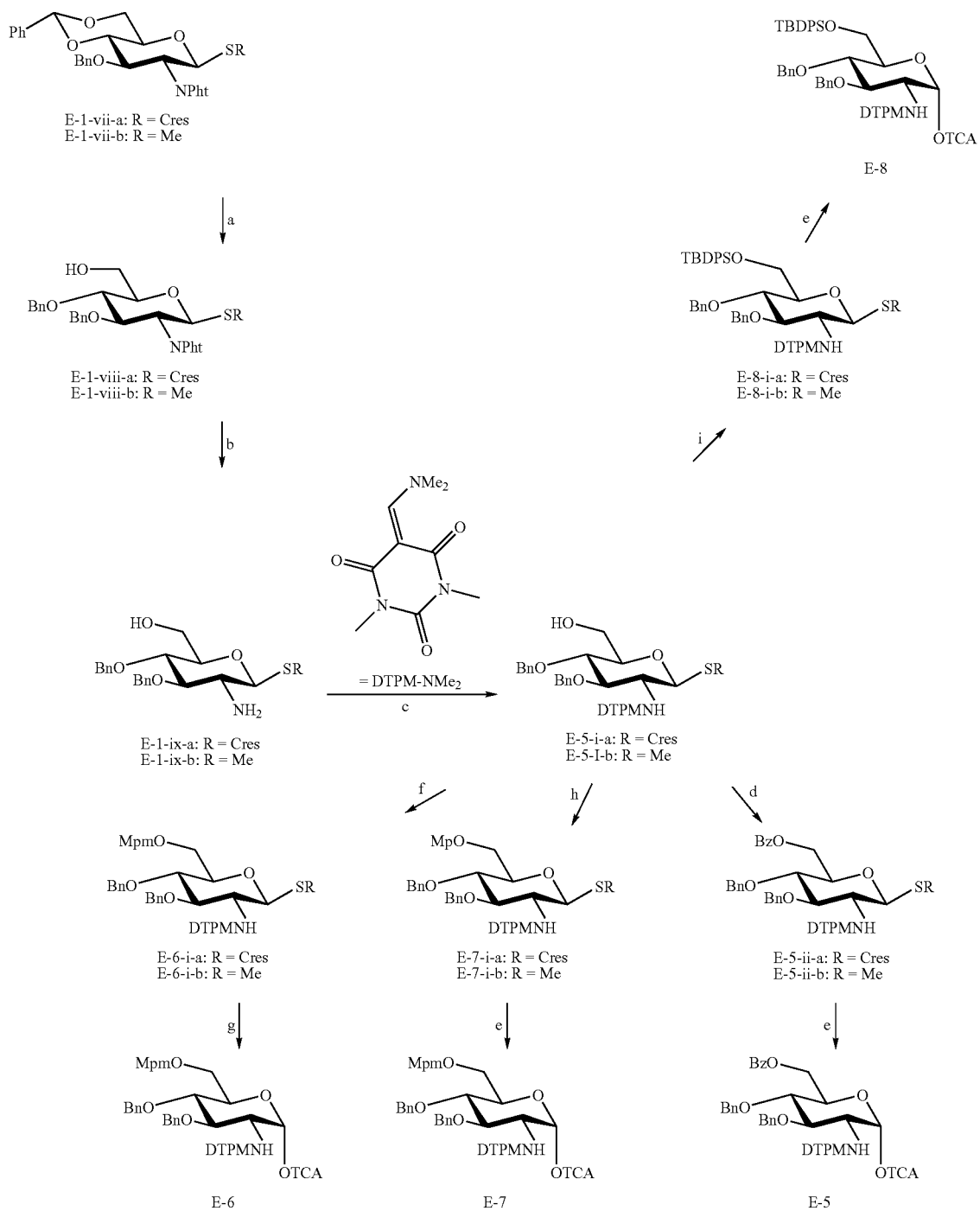

Example 16: Syntheses of Building Blocks E-5 to E-8, conditions: a) SOP 6, (85%, R=SMe); b) SOP 30, (86%, R=SMe); c) SOP 10, (88%, R=SMe); d) SOP 18, (92%, R=SMe); e) 1. SOP 13; 2. SOP 25b, (85%, 2 steps, R=SMe); f) SOP 7; g) 1. SOP 14; 2. SOP 25b; h) 1. TsCl, DMF; 2. p-MeO—C$_6$H$_4$—O Na, NMP, 60° C.; i) SOP 8.

Compound E-5:
$^1$H-NMR (400 MHz, CDCl$_3$): δ=10.20 (dd, 1H, $J_{NH,=C—H}$=14.0 Hz, $J_{NH,H\text{-}2}$=9.9 Hz, NH), 8.80 (s, 1H, C=NH), 8.16 (d, 1H, =C—H), 7.99 (m, 2H, Aryl) 7.58 (m, 1H, Aryl), 7.45 (m, 2H, Aryl), 7.30-7.17 (m, 10H, Aryl), 6.42 (d, 1H, $J_{1,2}$=3.6 Hz, H-1α), 4.89 (d, 1H, $J_{gem}$=8.4 Hz, OCH$_2$), 4.68-4.60 (m, 3H, OCH$_2$), 4.58 (dd, 1H, $J_{5,6a}$=2.0 Hz, $J_{gem}$=12.4 Hz, H-6a), 4.51 (dd, 1H, $J_{5,6b}$=4.0 Hz, H-6b), 4.22 (m, 1H, H-5), 4.03 (dd, 1H, $J_{3,4}$≈$J_{2,3}$=9.6 Hz, H-3), 3.80 (dd, 1H, $J_{4,5}$=9.4 Hz, H-4), 3.70 (ddd, 1H, H-2), 3.32 (s, 3H, NCH$_3$), 3.25 (s, 3H, NCH$_3$).

Example 17

Preparation of L-Iduronic Acid Containing Disaccharides B-A-1 to B-A-10

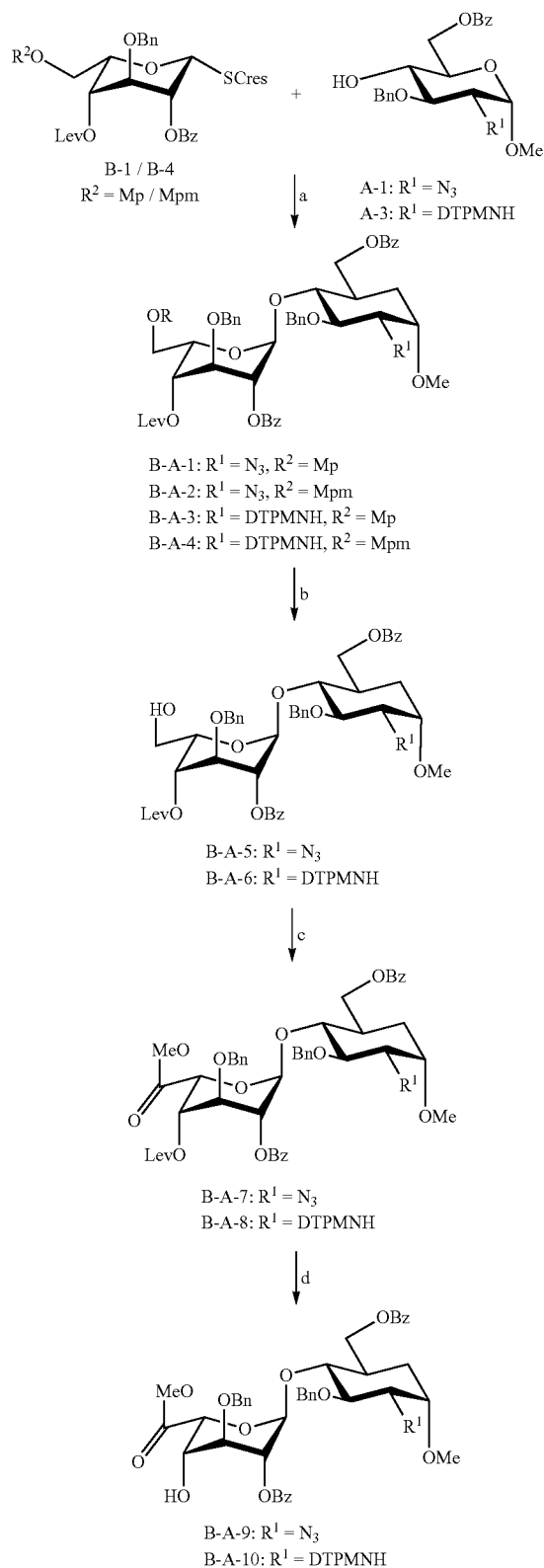

Example 17: Preparation L-iduronic acid containing disaccharides B-A-1 to B-A-10; a) SOP 32a, (76%, for B-A-1); b) SOP 27, (88%, for B-A-5); c) 1.SOP 20; 2. SOP 16, (84% for B-A-7, 2 steps); d) SOP 24, (94%, for B-A-9).

Formation of Disaccharide B-A-1 (Step a)

A suspension of A-1 (410 mg, 992 µmol), B-1 (680 mg, 992 µmol) and freshly activated molecular sieves 4 Å (1.0 g) in dry $CH_2Cl_2$ (20 mL) was stirred for 90 min at 0° C. N-Iodosuccinimide (405 mg, 1.8 mmol) was added and stirring continued for 20 min. After addition of trifluoromethanesulfonic acid (10.6 µl, 119.7 µmol), the reaction mixture was further stirred until completion (from 0° C. to 25° C.) and quenched with aqueous $NaHCO_3$-solution (10%). The mixture was diluted with $CH_2Cl_2$ and filtered through a celite pad. The filtrate was washed with a 10% $KHCO_3/Na_2S_2O_3$ solution, water and saturated brine solution, dried over $MgSO_4$ and evaporated. Final purification was achieved by silica gel column chromatography. Yield: 730 mg (76%).

Formation of Disaccharide B-A-7 (Step c)

Disaccharide B-A-5 (1.00 g, 1.15 mol) was dissolved in anhydrous DMF (7.0 mL) and reacted with pyridinium dichromate (4.33 g, 11.5 mmol) under stirring at room temperature until complete conversion into the uronic acid. The reaction mixture was subsequently poured into 50 mL water and the whole extracted with diethyl ether. The combined ether layers were washed with 10% aqueous citric acid solution, filtered through a short silica gel pad, dried over $MgSO_4$, evaporated and dried under high vacuum. The crude residue was dissolved in Toluene (3 mL) and methanol (3 mL) and titurated with $TMSCHN_2$ solution (2M in hexane) until completion. The excess of $TMSCHN_2$ was destroyed by addition of acetic acid and the mixture evaporated. Final purification was achieved via silica gel chromatography.

Yield: 871 mg (84%).

Compound B-A-9:

$^1$H-NMR (400 MHz, $CDCl_3$): δ=8.03 (m, 2H, Aryl), 7.91 (m, 2H, Aryl), 7.53 (m, 2H, Aryl), 7.42-7.23 (m, 14H, Aryl), 5.37 (d, 1H, $J_{1,2}$<1.5 Hz, H-1'α), 5.21 (m, 1H, H-2'), 4.97 (d, 1H, $J_{4,5}$=2.3 Hz, H-5'), 4.84 (d, 2H, $J_{gem}$=10.8 Hz, $OCH_2$), 4.81 (d, 1H, $J_{gem}$=10.8 Hz, $OCH_2$), 4.80 (d, 1H, $J_{1,2}$=3.6 Hz, H-1'α), 4.77 (1H, $J_{5,6a}$=1.8 Hz, H-6a), 4.70 (m, 2H, $OCH_2$), 4.47 (dd, 1H, $J_{5,6b}$=4.2 Hz, $J_{gem}$=12.3 Hz, H-6b), 4.05-3.97 (m, 3H, H-4', H-4, H-5), 3.91-3.87 (m, 2H, H-3', H-3), 3.49 (s, 3H, $OCH_3$), 3.44 (m, 1H, H-2), 3.43 (s, 3H, $OCH_3$).

Selected $^{13}$C-NMR (100 MHz, $CDCl_3$): δ=98.73 C-1' ($J_{CH}$=172.5 Hz), 98.35 C-1' ($J_{CH}$=171.8 Hz).

Example 18

Syntheses of Building Blocks E-D-1 to E-D-12

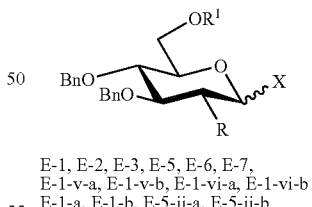

E-1, E-2, E-3, E-5, E-6, E-7,
E-1-v-a, E-1-v-b, E-1-vi-a, E-1-vi-b
E-1-a, E-1-b, E-5-ii-a, E-5-ii-b
E-6-i-a, E-6-i-b, E-7-i-a, E-7-i-b

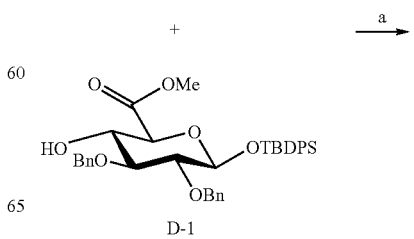

D-1

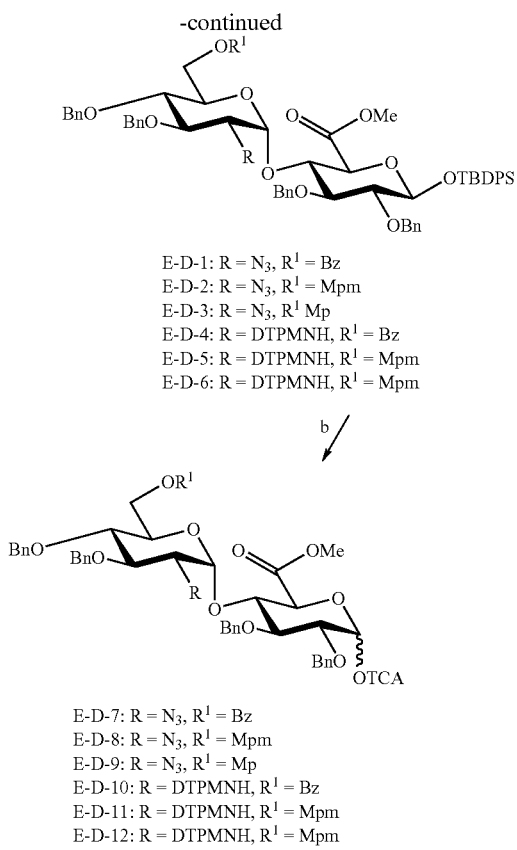

E-D-1: R = N₃, R¹ = Bz
E-D-2: R = N₃, R¹ = Mpm
E-D-3: R = N₃, R¹ Mp
E-D-4: R = DTPMNH, R¹ = Bz
E-D-5: R = DTPMNH, R¹ = Mpm
E-D-6: R = DTPMNH, R¹ = Mpm b ↓

E-D-7: R = N₃, R¹ = Bz
E-D-8: R = N₃, R¹ = Mpm
E-D-9: R = N₃, R¹ = Mp
E-D-10: R = DTPMNH, R¹ = Bz
E-D-11: R = DTPMNH, R¹ = Mpm
E-D-12: R = DTPMNH, R¹ = Mpm

Example 18: Syntheses of disaccharides E-D-1 to E-D-12, conditions: a) SOP 32a/b for X=SMe/SCres or SOP 33 for X=OTCA, (88% for E-D-1 via E-1, 84% for E-D-4 via E-5, as (α/β mixtures), b) 1. SOP 9; 2. SOP 25a, (90% for E-D-7 over 2 steps).

Preparation of E-D-1:Methyl (2-azido-6-O-benzoyl-3,4-di-O-benzyl-2-deoxy-β-D-glucopyranosyl)-(1→4)-tert-butyldiphenylsilyl 2,3-di-O-benzyl-β-D-glucopyranosid)uronote A mixture of 2-azido-6-O-benzoyl-2,3 di-O-benzyl-2-deoxy-α/β-D-glucopyranosyl trichloroacetimidate (2.5 g, 3.94 mmol), and methyl (tert-butyldiphenylsilyl 2,3-di-O-benzyl-β-D-glucopyranoside)uronote (1.6 g, 2.55 mmol) and molecular sieves 4 A (2.5 g) in 50 mL diethyl ether was treated with TBDMSOTf (180 μl, 788.76 μmol) at −20° C. for 1 h. The reaction was quenched filtered, concentrated and the residue purified by silica gel column chromatography to obtain the desired disaccharide 2.48 g, 88%. $R_f$=0.67 (toluene/ethyl acetate 9/1).

Compound E-D-1:

E-D-1 was formed according to SOP 33 with ether as solvent at −30° C. and TBDMSOTf as promoter in 86% yield (α/β-mixture).

¹H-NMR (400 MHz, CDCl₃): δ=8.00 (m, 2H, Aryl), 7.68 (m, 4H, Aryl), 7.56 (m, 1H, Aryl), 7.42 (m, 4H, Aryl), 7.36-7.17 (m, 24H, Aryl), 5.47 (d, 1H, $J_{1,2}$=3.8 Hz, H-1'α), 5.02 (d, 1H, $J_{gem}$=11.4 Hz, OCH₂), 4.97 (d, 1H, $J_{gem}$=11.0 Hz, OCH₂), 4.84 (m, 4H, OCH₂), 4.75 (d, 1H, $J_{gem}$=11.4 Hz, OCH₂), 4.66 (d, 1H, $J_{1,2}$=7.5 Hz, H-1β), 4.57 (d, 1H, $J_{gem}$=10.9 Hz, OCH₂), 4.45 (m, 2H, H-6'a, H-6'b), 4.15 (dd, J=8.8 Hz and J=9.6 Hz), 3.86 (m, 1H), 3.65 (s, 3H, OCH₃, 3.68-3.58 (m, 3H), 3.55 (d, 1H, $J_{4,5}$=10.0 Hz, H-5), 3.31 (dd, 1H, $J_{2,3}$=10.2 Hz, H-2'), 1.12 (s, 9H, C(CH₃)₃).

Compound E-D-4:

E-D-4 was formed according to SOP 33 with ether as solvent at −30° C. and TBDMSOTf as promoter in 84% yield (α/β-mixture).

Selected ¹H-NMR (400 MHz, CDCl₃): δ=10.02 (dd, 1H, $J_{NH,=C—H}$=14.4 Hz, $J_{NH,H-2}$=9.6 Hz, N—H), 8.02 (m, 2H, Aryl), 7.79 (d, 1H, =C—H), 7.72-6.93 (m, 33H, Aryl), 5.60 (d, 1H, $J_{1,2}$=3.6 Hz, H-1α), 4.49 (d, 1H, $J_{1,2}$=7.8 Hz, H-1β), 3.66 (s, 3H, OCH₃), 3.29 (s, 3H, NCH₃), 3.28 (s, 3H, NCH₃), 1.14 (s, 9H, C(CH₃)₃).

Preparation of E-D-7: Methyl (2-azido-6-O-benzoyl-3,4-di-O-benzyl-2-deoxy-α-D-glucopyranosyl)-(1→4)-2,3-di-O-benzyl-β-D-glucopyranosyl trichloroacetimidyl)uronote A solution of methyl (2-azido-6-O-benzoyl-3,4-di-O-benzyl-2-deoxy-α-D-glucopyranosyl)-(1→4)-tert-butyldiphenylsilyl 2,3-di-O-benzyl-β-D-glucopyranoside) uronate (2.09 g, 1.90 mmol) in acetic acid (1.74 mL, 30.45 mmol) and 1 M solution of tetrabutylammoniumfluoride (7.6 mL, 7.61 mmol) was stirred at room temperature overnight. The reaction mixture was then concentrated and the residual syrup was purified by silica gel column chromatography to obtain the desired hemiacetal.

Yield: 1.57 g (95.8%), $R_f$=0.21 (toluene/ethyl acetate 9/1).

A mixture of methyl (2-azido-6-O-benzoyl-3,4-di-O-benzyl-2-deoxy-α-D-glucopyranosyl)-(1-4)-2,3-di-O-benzyl-β-D-glucopyranosyl) uronote (594 mg, 690.70 μmol), trichloroacetonitrile (280 μl, 2.74 mmol) and DBU (31 μl, 209.3 μmol) in 8.0 mL dichloromethane was stirred at 0° C. for 1 h. The mixture was then concentrated and purified on a short column of silica gel to obtain the title compound as an amorphous white solid. Yield: 662 mg (95.3%), $R_f$=0.46 (toluene/ethyl acetate 9/1).

Compound E-D-7:

Selected ¹H-NMR (400 MHz, CDCl₃): δ=8.68 (s, 1H, C=NH), 8.00 (m, 2H, Aryl), 7.56 (m, 2H, Aryl), 7.43-7.23 (m, 22H, Aryl), 6.48 (d, 1H, $J_{1,2}$=4.3 Hz, H-1α), 5.59 (d, 1H, $J_{1,2}$=3.6 Hz, H-1'α), 5.03 (1H, $J_{gem}$=10.8 Hz, OCH₂), 4.93-4.83 (m, 4H, OCH₂), 4.70 (d, 1H, $J_{gem}$=12.0 Hz, OCH₂), 4.64 (d, 1H, $J_{gem}$=12.0 Hz, OCH₂), 4.60 (d, 1H, $J_{gem}$=11.2 Hz, OCH₂), 4.47 (m, 2H, H-6'a, H-6'b), 4.42 (m, 1H, not assigned), 4.15 (m, 2H, not assigned), 3.97 (dd, 1H, J=8.2 Hz and J=10.2 Hz, not assigned), 3.80 (m, 1H, not assigned), 3.76 (m, 3H, OCH₃), 3.72-3.64 (m, 2H, not assigned), 3.30 (dd, 1H, $J_{2,3}$=10.4 Hz, H-2').

Example 19

Syntheses of Disaccharides E-D-13 to E-D-44

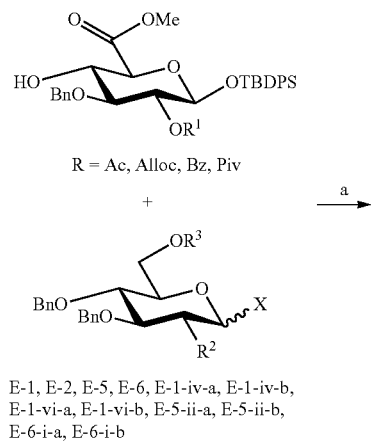

R = Ac, Alloc, Bz, Piv

+ a →

E-1, E-2, E-5, E-6, E-1-iv-a, E-1-iv-b,
E-1-vi-a, E-1-vi-b, E-5-ii-a, E-5-ii-b,
E-6-i-a, E-6-i-b

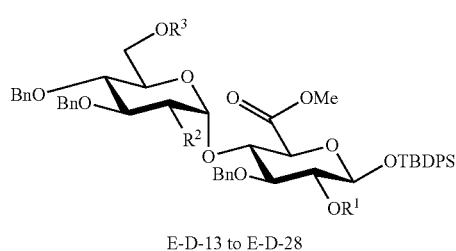

E-D-13 to E-D-28

↓ b

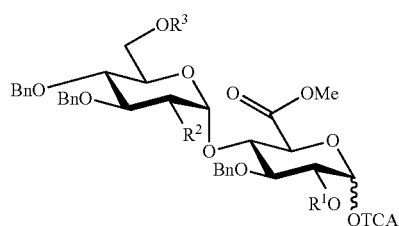

E-D-29 to E-D-44

E-D-13 & E-D-29: R³ = Bz, R² = N₃, R¹ = Alloc
E-D-14 & E-D-30: R³ = Bz, R² = NHDTPM, R¹ = Alloc
E-D-15 & E-D-31: R³ = Mpm, R² = N₃, R¹ = Alloc
E-D-16 & E-D-32: R³ = Mpm, R² = NHDTPM, R¹ = Alloc
E-D-17 & E-D-33: R³ = Bz, R² = N₃, R¹ = Piv
E-D-18 & E-D-34: R³ = Bz, R² = NHDTPM, R¹ = Piv
E-D-19 & E-D-35: R³ = Mpm, R² = N₃, R¹ = Piv
E-D-20 & E-D-36: R³ = Mpm, R² = NHDTPM, R¹ = Piv
E-D-21 & E-D-37: R³ = Bz, R² = N₃, R¹ = Bz
E-D-22 & E-D-38: R³ = Bz, R² = NHDTPM, R¹ = Bz
E-D-23 & E-D-39: R³ = Mpm, R² = N₃, R¹ = Bz
E-D-24 & E-D-40: R³ = Mpm, R² = NHDTPM, R¹ = Bz
E-D-25 & E-D-41: R³ = Bz, R² = N₃, R¹ = Ac
E-D-26 & E-D-42: R³ = Bz, R² = NHDTPM, R¹ = Ac
E-D-27 & E-D-43: R³ = Mpm, R² = N₃, R¹ = Ac
E-D-28 & E-D-44: R³ = Mpm, R² = NHDTPM, R¹ = Ac Example 19: Syntheses of disaccharides E-D-13 to E-D-44, conditions: a) SOP 32a/b for X=SMe/SCres or SOP 33 for X=OTCA (70% for E-D-23, α/β mixture); b) 1. SOP 9; 2. SOP 25a.

Compound E-D-27:

E-D-27 was formed according to SOP 33 with ether as solvent at −20° C. and TBDMSOTf as promoter in 70% yield (α/β-mixture). Selected ¹H-NMR (400 MHz, CDCl₃): δ=7.58 (m, 2H, Aryl), 7.54 (m, 2H, Aryl), 7.36-7.00 (m, 23H, Aryl), 6.73 (m, 2H, Aryl), 5.37 (d, 1H, $J_{1,2}$=3.9 Hz, H-1'α), 5.12 (dd, 1H, $J_{2,3}$=8.8 Hz, H-2), 4.63 (d, 1H, $J_{gem}$=11.2 Hz, OCH₂), 4.58 (d, 1H, $J_{gem}$=11.2 Hz, OCH₂), 4.48 (d, 1H, $J_{1,2}$=7.3 Hz, H-1β), 3.66 (s, 3H, OCH₃), 3.55 (s, 3H, OCH₃), 3.34 (m, 1H), 3.22 (dd, 1H, J=3.4 Hz, J=10.7 Hz), 1.81 (s, 3H, Oac), 0.98 (s, 9H, C(CH₃)₃).

Example 20

Synthesis of Alternative E-D-Disaccharides E-D-45 to E-D-50

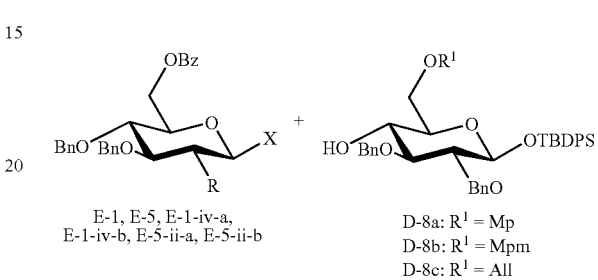

E-1, E-5, E-1-iv-a,
E-1-iv-b, E-5-ii-a, E-5-ii-b

D-8a: R¹ = Mp
D-8b: R¹ = Mpm
D-8c: R¹ = All

↓ a

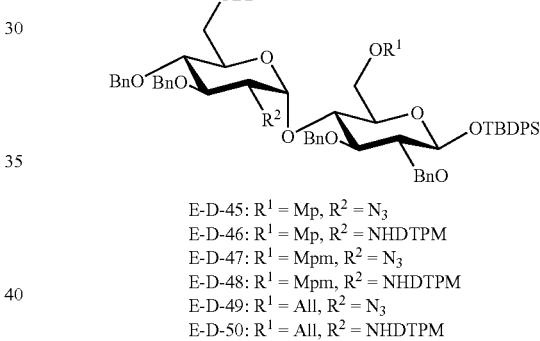

E-D-45: R¹ = Mp, R² = N₃
E-D-46: R¹ = Mp, R² = NHDTPM
E-D-47: R¹ = Mpm, R² = N₃
E-D-48: R¹ = Mpm, R² = NHDTPM
E-D-49: R¹ = All, R² = N₃
E-D-50: R¹ = All, R² = NHDTPM

Example 20: Synthesis of alternative E-D-disaccharides E-D-45 to E-D-50, conditions: a) SOP 32a/b for X=SMe/SCres or SOP 33 for X=OTCA, diethyl ether, TBDMS-Otf, −20 deg. C. (75% for E-D-45 as (α/β-mixture).

Example 21

Synthesis of Trisaccharides E-D-C-1 to E-D-C-16

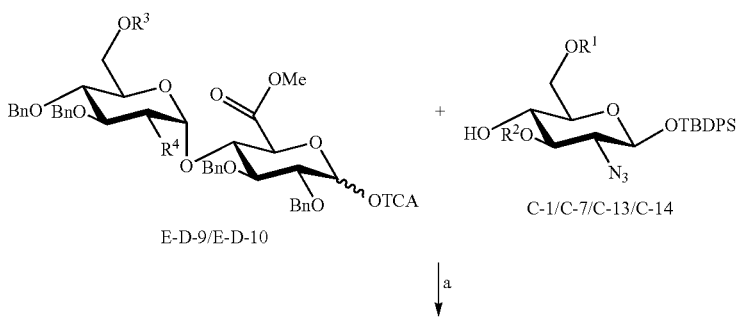

E-D-9/E-D-10

C-1/C-7/C-13/C-14

↓ a

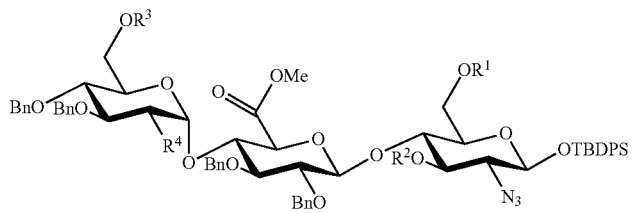

E-D-C-1: R¹ = Mpm, R² = Mpm, R³ = Mpm, R⁴ = NHDTPM
E-D-C-2: R¹ = Mp, R² = Mpm, R³ = Mpm, R⁴ = NHDTPM
E-D-C-3: R¹ = Mpm, R² = Mpm, R³ = Bz, R⁴ = NHDTPM
E-D-C-4: R¹ = Mp, R² = Mpm, R³ = Bz, R⁴ = NHDTPM
E-D-C-5: R¹ = Mpm, R² = Bz, R³ = Mpm, R⁴ = NHDTPM
E-D-C-6: R¹ = Mp, R² = Bz, R³ = Mpm, R⁴ = NHDTPM
E-D-C-7: R¹ = Mpm, R² = Bz, R³ = Bz, R⁴ = NHDTPM
E-D-C-8: R¹ = Mp, R² = Bz, R³ = Bz, R⁴ = NHDTPM
E-D-C-9: R¹ = Mpm, R² = Mpm, R³ = Mpm, R⁴ = N₃
E-D-C-10: R¹ = Mp, R² = Mpm, R³ = Mpm, R⁴ = N₃
E-D-C-11: R¹ = Mpm, R² = Mpm, R³ = Bz, R⁴ = N₃
E-D-C-12: R¹ = Mp, R² = Mpm, R³ = Bz, R⁴ = N₃
E-D-C-13: R¹ = Mpm, R² = Bz, R³ = Mpm, R⁴ = N₃
E-D-C-14: R¹ = Mp, R² = Bz, R³ = Mpm, R⁴ = N₃
E-D-C-15: R¹ = Mpm, R² = Bz, R³ = Bz, R⁴ = N₃
E-D-C-16: R¹ = Mp, R² = Bz, R³ = Bz, R⁴ = N₃

Example 21: Synthesis of trisaccharide E-D-C-1 to E-D-C-16, conditions: a) SOP 33, (70% for E-D-C 15 as an α/β mixture).

Compound E-D-C-15:

E-D-C-15 was formed according to SOP 33 with dichloromethane as solvent at 0 to 20° C. and TBDMSOTf as promoter in 70% yield (α/β-mixture).

¹H-NMR (400 MHz, CDCl₃): δ=7.93 (m, 2H, Aryl), 7.87 (m, 2H, Aryl), 7.66 (m, 2H, Aryl), 7.61 (m, 2H, Aryl), 7.46 (m, 2H, Aryl), 7.38-6.99 (m, 32H, Aryl), 6.79 (m, 2H, Aryl), 5.27 (d, 1H, $J_{1,2}$=3.8 Hz, H-1"α), 4.99 (dd, 1H, $J_{3,4}$≈$J_{2,3}$=9.5 Hz, H-3), 4.80-4.69 (m, 6H, OCH₂), 4.52 (m, 3H, OCH₂), 4.40 (d, 1H, $J_{1,2}$=8.0 Hz, H-1β), 4.38-4.32 (m, 2H, not assigned), 4.29 (d, 1H, $J_{1,2}$=7.5 Hz, H-1β), 4.15 (m, 1H, $J_{gem}$=12.0 Hz, OCH₂), 4.02 (dd, 1H, $J_{4,5}$=9.6 Hz, H-4), 3.80 (2 dd, 2H, H-3", H-4'), 3.71, (s, 3H, OCH₃), 3.67 (m, 1H, not assigned), 3.61-3.53 (m, 2H, H-5', H-2'), 3.46 (dd, 1H, $J_{gem}$=11.2 Hz, $J_{5,6a}$=2.4 Hz, H-6a), 3.41 (dd, 1H, $J_{2,3}$≈$J_{3,4}$=9.0 Hz, H-3'), 3.27 (s, 3H, OCH₃), 3.21 (dd, 1H, $J_{2,3}$=10.0 Hz, H-2"), 3.14 (dd, 1H, H-2'), 3.00 (dd, 1H, $J_{5,6b}$<2.0 Hz, H-6b), 2.75 (m, 1H, H-5) 1.05 (s, 9H, C(CH₃)₃).

Example 22

Synthesis of Trisaccharides E-D-C-17 to E-D-C-32

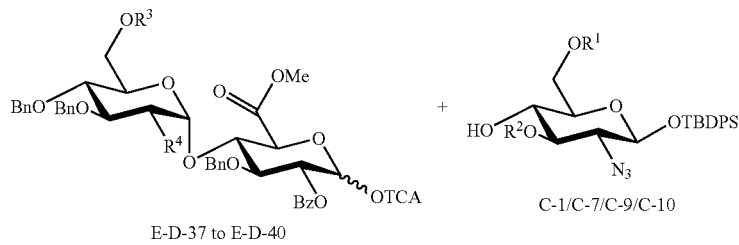

E-D-37 to E-D-40    C-1/C-7/C-9/C-10 a

-continued

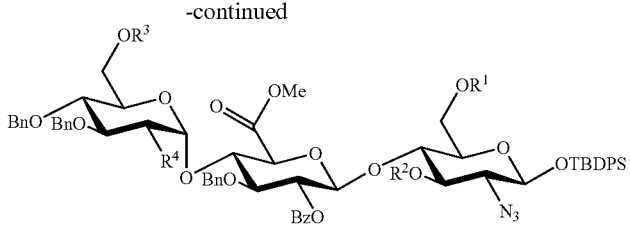

E-D-C-17: $R^1$ = Mpm, $R^2$ = Mpm, $R^3$ = Mpm, $R^4$ = NHDTPM
E-D-C-18: $R^1$ = Mp, $R^2$ = Mpm, $R^3$ = Mpm, $R^4$ = NHDTPM
E-D-C-19: $R^1$ = Mpm, $R^2$ = Mpm, $R^3$ = Bz, $R^4$ = NHDTPM
E-D-C-20: $R^1$ = Mp, $R^2$ = Mpm, $R^3$ = Bz, $R^4$ = NHDTPM
E-D-C-21: $R^1$ = Mpm, $R^2$ = Bz, $R^3$ = Mpm, $R^4$ = NHDTPM
E-D-C-22: $R^1$ = Mp, $R^2$ = Bz, $R^3$ = Mpm, $R^4$ = NHDTPM
E-D-C-23: $R^1$ = Mpm, $R^2$ = Bz, $R^3$ = Bz, $R^4$ = NHDTPM
E-D-C-24: $R^1$ = Mp, $R^2$ = Bz, $R^3$ = Bz, $R^4$ = NHDTPM
E-D-C-25: $R^1$ = Mpm, $R^2$ = Mpm, $R^3$ = Mpm, $R^4$ = $N_3$
E-D-C-26: $R^1$ = Mp, $R^2$ = Mpm, $R^3$ = Mpm, $R^4$ = $N_3$
E-D-C-27: $R^1$ = Mpm, $R^2$ = Mpm, $R^3$ = Bz, $R^4$ = $N_3$
E-D-C-28: $R^1$ = Mp, $R^2$ = Mpm, $R^3$ = Bz, $R^4$ = $N_3$
E-D-C-29: $R^1$ = Mpm, $R^2$ = Bz, $R^3$ = Mpm, $R^4$ = $N_3$
E-D-C-30: $R^1$ = Mp, $R^2$ = Bz, $R^3$ = Mpm, $R^4$ = $N_3$
E-D-C-31: $R^1$ = Mpm, $R^2$ = Bz, $R^3$ = Bz, $R^4$ = $N_3$
E-D-C-32: $R^1$ = Mp, $R^2$ = Bz, $R^3$ = Bz, $R^4$ = $N_3$

Example 22: Synthesis of trisaccharide E-D-C-17 to E-D-C-32, conditions: a) SOP 33.

Example 23

Formation of Trisaccharidic Trichloroacetimidates E-D-C-33 to E-D-C-48

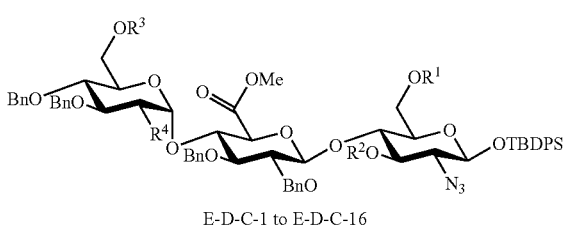

E-D-C-1 to E-D-C-16

↓a

-continued

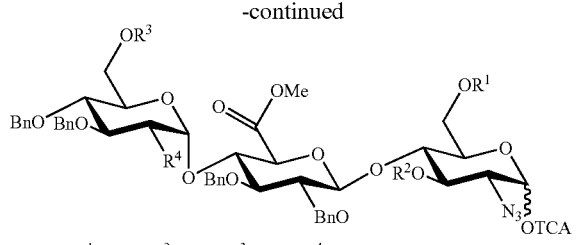

E-D-C-33: $R^1$ = Mpm, $R^2$ = Mpm, $R^3$ = Mpm, $R^4$ = NHDTPM
E-D-C-34: $R^1$ = Mp, $R^2$ = Mpm, $R^3$ = Mpm, $R^4$ = NHDTPM
E-D-C-35: $R^1$ = Mpm, $R^2$ = Mpm, $R^3$ = Bz, $R^4$ = NHDTPM
E-D-C-36: $R^1$ = Mp, $R^2$ = Mpm, $R^3$ = Bz, $R^4$ = NHDTPM
E-D-C-37: $R^1$ = Mpm, $R^2$ = Bz, $R^3$ = Mpm, $R^4$ = NHDTPM
E-D-C-38: $R^1$ = Mp, $R^2$ = Bz, $R^3$ = Mpm, $R^4$ = NHDTPM
E-D-C-39: $R^1$ = Mpm, $R^2$ = Bz, $R^3$ = Bz, $R^4$ = NHDTPM
E-D-C-40: $R^1$ = Mp, $R^2$ = Bz, $R^3$ = Bz, $R^4$ = NHDTPM
E-D-C-41: $R^1$ = Mpm, $R^2$ = Mpm, $R^3$ = Mpm, $R^4$ = $N_3$
E-D-C-42: $R^1$ = Mp, $R^2$ = Mpm, $R^3$ = Mpm, $R^4$ = $N_3$
E-D-C-43: $R^1$ = Mpm, $R^2$ = Mpm, $R^3$ = Bz, $R^4$ = $N_3$
E-D-C-44: $R^1$ = Mp, $R^2$ = Mpm, $R^3$ = Bz, $R^4$ = $N_3$
E-D-C-45: $R^1$ = Mpm, $R^2$ = Bz, $R^3$ = Mpm, $R^4$ = $N_3$
E-D-C-46: $R^1$ = Mp, $R^2$ = Bz, $R^3$ = Mpm, $R^4$ = $N_3$
E-D-C-47: $R^1$ = Mpm, $R^2$ = Bz, $R^3$ = Bz, $R^4$ = $N_3$
E-D-C-48: $R^1$ = Mp, $R^2$ = Bz, $R^3$ = Bz, $R^4$ = $N_3$

Example 23: Formation of trisaccharidic Trichloroacetimidates E-D-C-33 to E-D-C-48, conditions: a) 1. SOP 9; 2. SOP 25, (82% over 2 steps for E-D-C-47

Example 24

Syntheses of Trisaccharides E-D-C-9 to E-D-C-12 and E-D-C-49 to E-D-C-60

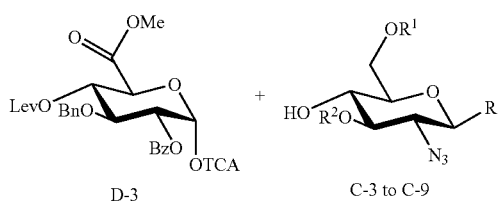

D-3      C-3 to C-9

↓a

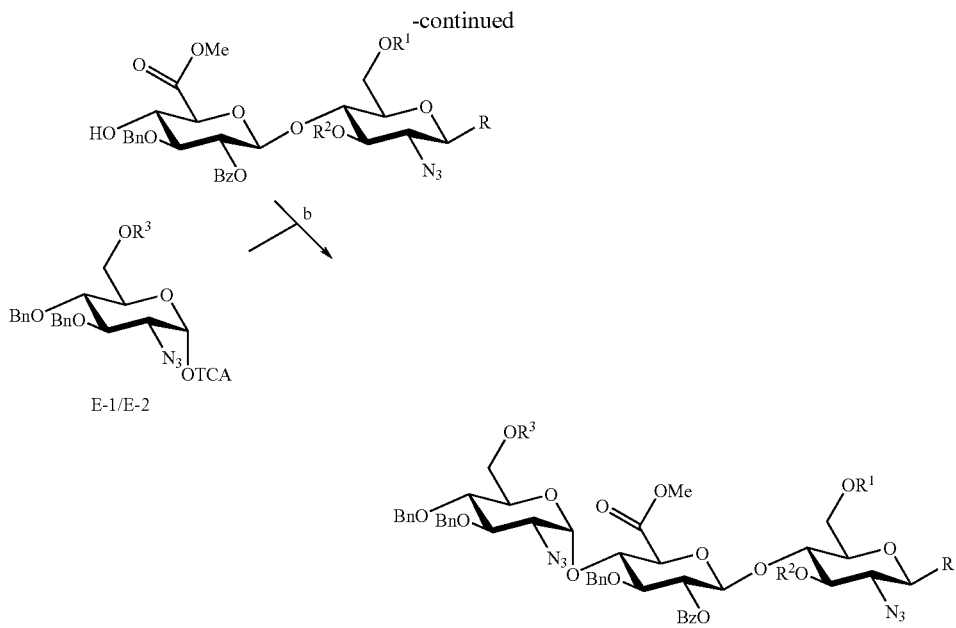

C-6a: R = SCres, R$^1$ = Mpm, R$^2$ = Mpm
C-7: R = OTBDPS, R$^1$ = Mpm, R$^2$ = Mpm
C-8c: R = OTBDPS, R$^1$ = Mp, R$^2$ = All
C-10: R = SCres, R$^1$ = Mp, R$^2$ = Mpm
C-11: R = SCres, R$^1$ = Mpm, R$^2$ = All
C-12: R = OTBDPS, R$^1$ = Mpm, R$^2$ = All
C-13: R = SCres, R$^1$ = Mp, R$^2$ = All
C-14: R = OTBDPS, R$^1$ = Mp, R$^2$ = Mpm
D-C-1: R = SCres, R$^1$ = Mpm, R$^2$ = Mpm
D-C-2: R = SCres, R$^1$ = Mpm, R$^2$ = All
D-C-3: R = SCres, R$^1$ = Mp, R$^2$ = Mpm
D-C-4: R = SCres, R$^1$ = Mp, R$^2$ All
D-C-5: R = OTBDPS, R$^1$ = Mpm, R$^2$ = Mpm
D-C-6: R = OTBDPS, R$^1$ = Mpm, R$^2$ = All
D-C-7: R = OTBDPS, R$^1$ = Mp, R$^2$ = Mpm
D-C-8: R = OTBDPS, R$^1$ = Mp, R$^2$ = All
E-D-C-49: R = SCres, R$^1$ = Mpm, R$^2$ = Mpm, R$^3$ = Bz
E-D-C-50: R = SCres, R$^1$ = Mpm, R$^2$ = All, R$^3$ = Bz
E-D-C-51: R = SCres, R$^1$ = Mp, R$^2$ = Mpm, R$^3$ = Bz
E-D-C-52: R = SCres, R$^1$ = Mp, R$^2$ = All, R$^3$ = Bz
E-D-C-53: R = SCres, R$^1$ = Mpm, R$^2$ = Mpm, R$^3$ = Mpm
E-D-C-54: R = SCres, R$^1$ = Mpm, R$^2$ = All, R$^3$ = Mpm
E-D-C-55: R = SCres, R$^1$ = Mp, R$^2$ = Mpm, R$^3$ = Mpm
E-D-C-56: R = SCres, R$^1$ = Mp, R$^2$ = All, R$^3$ = Mpm
E-D-C-11: R = OTBDPS, R$^1$ = Mpm, R$^2$ = Mpm, R$^3$ = Bz
E-D-C-57: R = OTBDPS, R$^1$ = Mpm, R$^2$ = All, R$^3$ = Bz
E-D-C-12: R = OTBDPS, R$^1$ = Mp, R$^2$ = Mpm, R$^3$ = Bz
E-D-C-58: R = OTBDPS, R$^1$ = Mp, R$^2$ = All, R$^3$ = Bz
E-D-C-9: R = OTBDPS, R$^1$ = Mpm, R$^2$ = Mpm, R$^3$ = Mpm
E-D-C-59: R = OTBDPS, R$^1$ = Mpm, R$^2$ = All, R$^3$ = Mpm
E-D-C-10: R = OTBDPS, R$^1$ = Mp, R$^2$ = Mpm, R$^3$ = Mpm
E-D-C-60: R = OTBPS, R$^1$ = Mp, R$^2$ = All, R$^3$ = Mpm Example 24: Syntheses of trisaccharides E-D-C-9 to E-D-C-12 and E-D-C-49 to E-D-C-60, conditions: a) 1. SOP 33; 2. SOP 24; b) SOP 33, (for D-C-5: 70%, 2 steps); b) SOP 33, (78% for E-D-C-9 as an α/β mixture).

Compound D-C-5:

D-C-5 was formed according to SOP 33 with ether as solvent at −20° C. and TMSOTf as promoter, followed by SOP 24 in 70% yield (over 2 steps as α/β-mixture).

Selected $^1$H-NMR (400 MHz in CDCl$_3$): δ=7.88 (m, 2H, Ar), 7.67-7.58 (m, 5H, Ar), 7.42 (m, 2H, Ar), 7.37-7.12 (m, 16H, Aryl), 6.84 (m, 3H, Ar), 5.14 (dd, 1H, $J_{1,2}$=8.2 Hz, $J_{2,3}$=9.5 Hz, H-2'), 4.90 (d, 1H, $J_{gem}$=10.7 Hz, OCH$_2$), 4.73 (d, 1H, $J_{gem}$=11.5 Hz, OCH$_2$), 4.65 (d, 1H, $J_{1,2}$=8.2 Hz, H-1'β), 4.63-4.58 (m, 2H, OCH$_2$), 4.51 (d, 1H, $J_{gem}$=12.0 Hz, OCH$_2$), 4.20 (d, 1H, $J_{1,2}$=7.9 Hz, H-1β), 4.05 (d, 1H, $J_{gem}$=11.9 Hz, OCH$_2$), 4.02-3.95 (m, 2H, not assigned), 3.81 (s, 3H, OCH$_3$), 3.80 (s, 3H, OCH$_3$), 3.71 (d, 1H, $J_{4,5}$=9.9 Hz, H-5'), 3.67 (s, 3H, OCH$_3$), 3.47-3.40 (m, 3H, not assigned), 3.21 (dd, 1H, J=9.0 Hz, J=9.8 Hz, not assigned), 3.00 (dd, 1H, $J_{5,6b}$=1.4 Hz, $J_{gem}$=10.5 Hz, H-6b), 2.63 (m, 1H, H-5), 2.35 (bs, 1H, 4-OH), 1.07 (s, 9H, C(CH$_3$)$_3$).

Compound E-D-C-9:

E-D-C-9 was formed according to SOP 33 with ether as solvent at −20° C. and TBDMSOTf as promoter in 78% yield (α/β-mixture).

Selected $^1$H-NMR (400 MHz, CDCl$_3$): δ=7.77 (m, 2H, Aryl), 7.59, 7.54 (2m, 2×2H, Aryl), 7.35-7.00 (m, 30H, Aryl), 6.88 (m, 2H, Aryl), 6.82 (m, 2H, Aryl), 6.73 (m, 2H, Aryl), 5.41 (d, 1H, $J_{1,2}$=3.5 Hz, H-1'α), 5.19 (dd, 1H, $J_{2,3}$≈$J_{1,2}$=9.6 Hz, H-2'), 4.85-4.78 (m, 4H, OCH$_2$), 4.67 (m, 2H, OCH$_2$), 4.65 (d, 1H, $J_{1,2}$=8.5 Hz, H-1β, not assigned), 4.38 (d, 1H, $J_{gem}$=11.1 Hz, OCH$_2$), 4.29 (d, 1H, $J_{gem}$=11.7 Hz, OCH$_2$), 4.17 (dd, 1H, not assigned), 4.11 (d, 1H, $J_{1,2}$=7.9 Hz, H-1β not assigned), 4.03 (d, 1H, $J_{gem}$=12.0 Hz, OCH$_2$), 3.90-3.76 (m, 3H, not assigned), 3.730, 3.727 (2s, 2×3H, OCH$_3$), 3.65 (s, 3H, OCH$_3$), 3.54 (s, 3H, OCH$_3$), 2.89 (dd, 1H, $J_{gem}$=10.5 Hz, $J_{5,6b}$<2.0 Hz, H-6b), 2.52 (m, 1H, H-5), 1.02 (s, 9H, C(CH$_3$)$_3$).

Example 25

Synthesis of Trisaccharides E-D-C-41 E-D-C-42 and E-D-C-61 to E-D-C-66

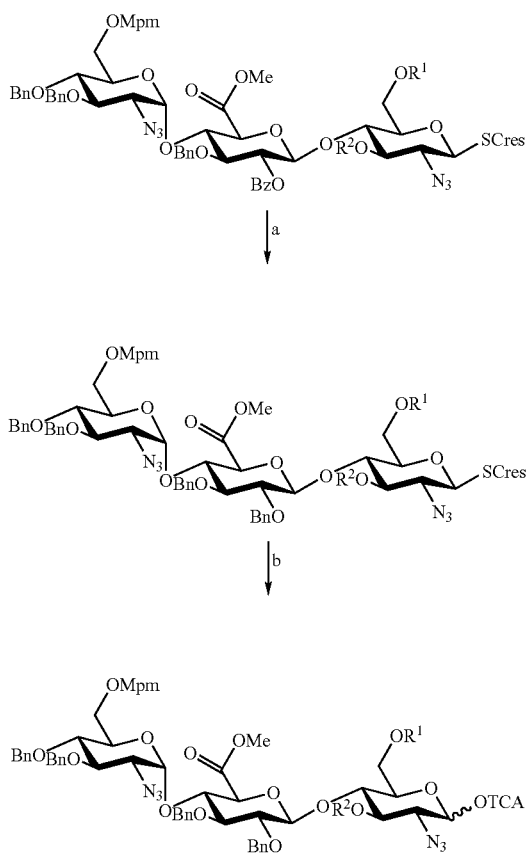

E-D-C-53: R$^1$ = Mpm, R$^2$ = Mpm
E-D-C-54: R$^1$ = Mpm, R$^2$ = All
E-D-C-55: R$^1$ = Mp, R$^2$ = Mpm
E-D-C-56: R$^1$ = Mp, R$^2$ = All
E-D-C-61: R$^1$ = Mpm, R$^2$ = Mpm
E-D-C-62: R$^1$ = Mpm, R$^2$ = All
E-D-C-63: R$^1$ = Mp, R$^2$ = Mpm
E-D-C-64: R$^1$ = Mp, R$^2$ = All
E-D-C-41: R$^1$ = Mpm, R$^2$ = Mpm
E-D-C-42: R$^1$ = Mp, R$^2$ = Mpm
E-D-C-65: R$^1$ = Mpm, R$^2$ = All
E-D-C-66: R$^1$ = Mp, R$^2$ = All

Example 25: Synthesis of trisaccharides E-D-C-41, E-D-C-42 and E-D-C-61 to E-D-C-66, conditions: a) 1. SOP 39; 2. SOP 38; 3. SOP 16; b) 1. SOP 14; 2. SOP 25a.

Example 26

An Alternative Route to the Trisaccharides E-D-C-61 and E-D-C-43

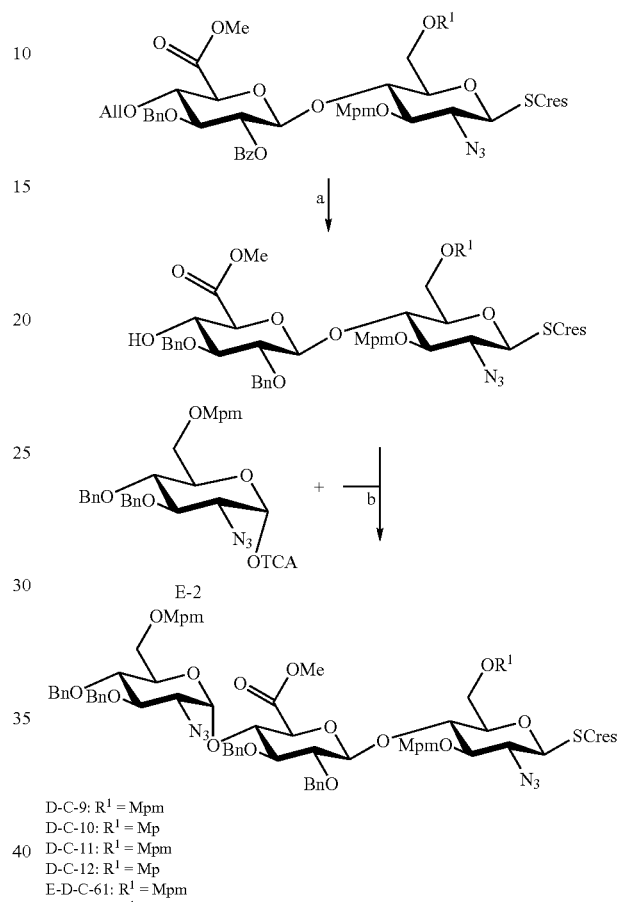

D-C-9: R$^1$ = Mpm
D-C-10: R$^1$ = Mp
D-C-11: R$^1$ = Mpm
D-C-12: R$^1$ = Mp
E-D-C-61: R$^1$ = Mpm
E-D-C-63: R$^1$ = Mp

Example 26: An alternative route to the trisaccharides E-D-C-61 and E-D-C-63, conditions: a) 1. SOP 39; 2. SOP 38; 3. SOP 16; 4. Pd(Ph$_3$P)$_4$, p-TolSO$_2$Na, THF, MeOH; b) SOP 33.

Example 27

Syntheses of Blocks E-D-C-67 to E-D-C-70

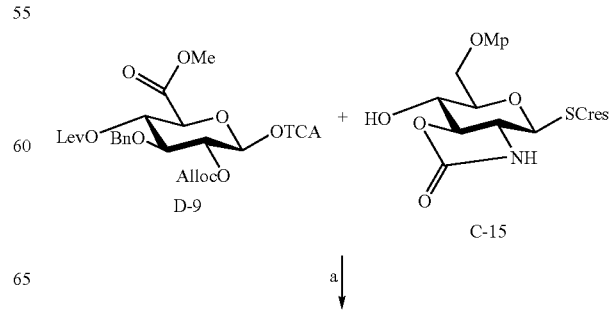

75

-continued

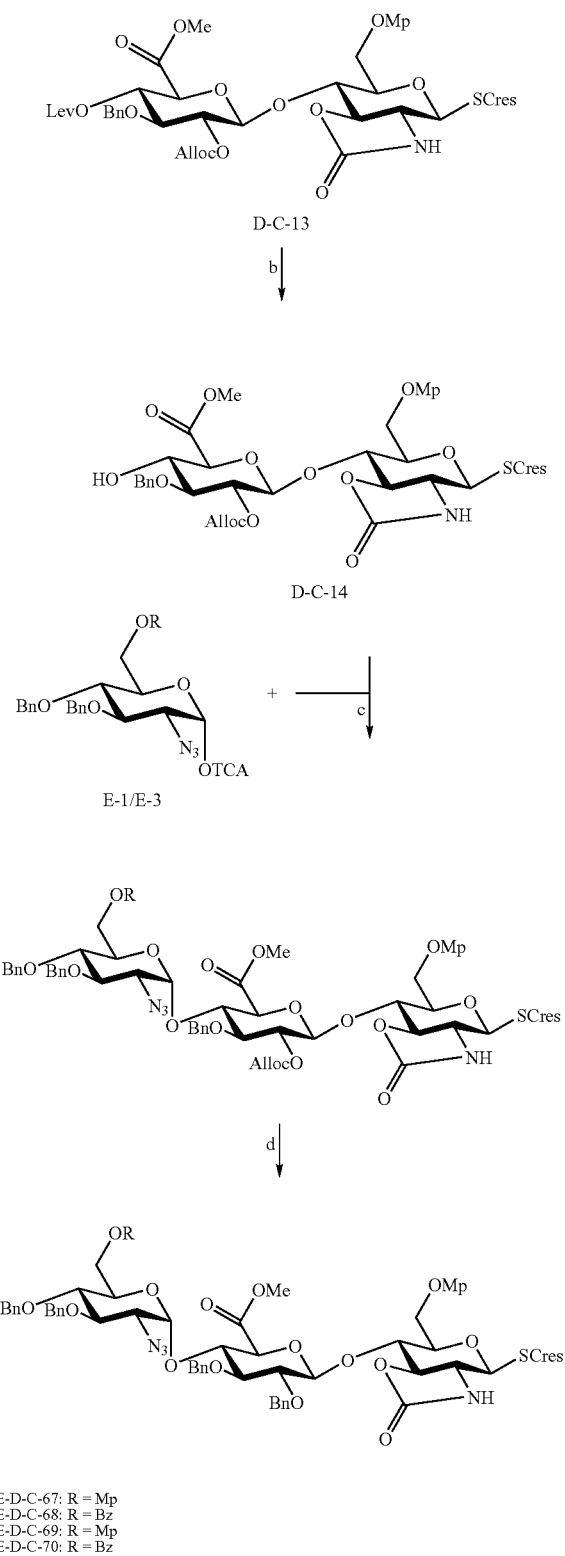

E-D-C-67: R = Mp
E-D-C-68: R = Bz
E-D-C-69: R = Mp
E-D-C-70: R = Bz

Example 27: Syntheses of trisaccharides E-D-C-67 to E-D-C-70, conditions: a) SOP 33; b) SOP 24; c) SOP 33; d) 1. SOP 36; 2. SOP 37.

76

Example 28

Synthesis of Trisaccharides E-D-C-70 and E-D-C-71

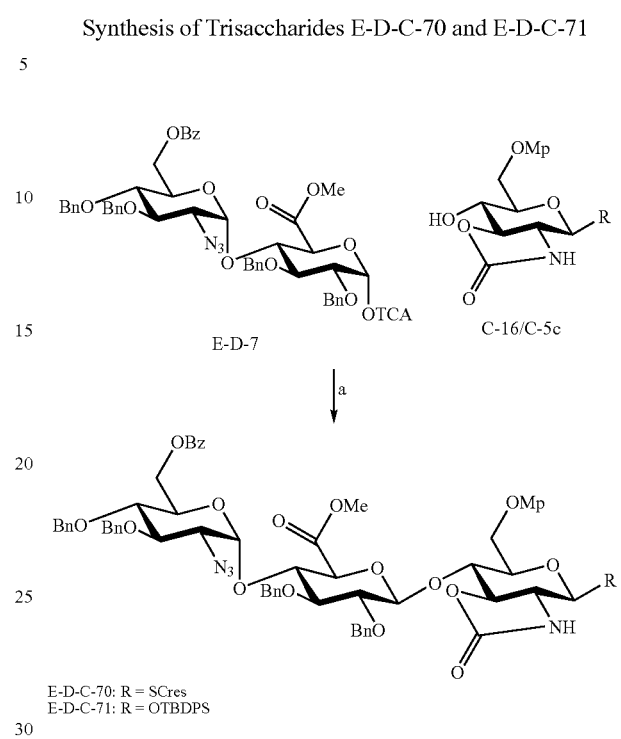

E-D-C-70: R = SCres
E-D-C-71: R = OTBDPS

Example 28: Synthesis of trisaccharides E-D-C-70 and E-D-C-71, conditions: a) SOP 33, (55% for E-D-C-71, α/β mixture).

Compound E-D-C-71:

E-D-C-71 was formed according to SOP 33 with dichloromethane as solvent at 40° C. and TBDMSOTf as promoter in 55% yield (as α/β-mixture).

Selected $^1$H-NMR (400 MHz, CDCl$_3$): δ=7.91 (m, 2H, Aryl), 7.61 (m, 2H, Aryl), 7.55 (m, 2H, Aryl), 7.50-7.02 (m, 29H, Aryl), 6.65 (m, 4H, Mp), 5.38 (d, 1H, $J_{1,2}$=3.9 Hz, H-1"α), 5.22 (bs, 1H, NH), 4.67 (d, 1H, $J_{1,2}$=7.4 Hz, H-1β, not assigned), 4.50 (d, 1H, $J_{1,2}$=7.8 Hz, H-1β, not assigned), 3.92 (d, 1H, $J_{4,5}$=9.8 Hz, H-5'), 3.698 (s, 3H, OCH$_3$), 3.693 (s, 3H, OCH$_3$), 1.03 (s, 9H, C(CH$_3$)$_3$).

$M_{found}$=1408.52 (M+H$_2$O)$^+$, $M_{calc}$=1390.54 (M$^+$).

Example 29

Syntheses of Trisaccharides E-D-C-61, E-D-C-72 and E-D-C-73

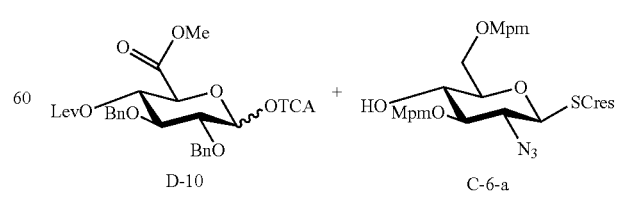

D-10        C-6-a a

77
-continued

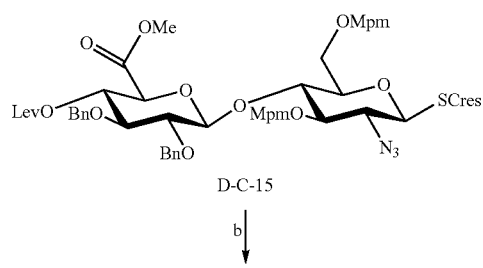

D-C-15 b ↓

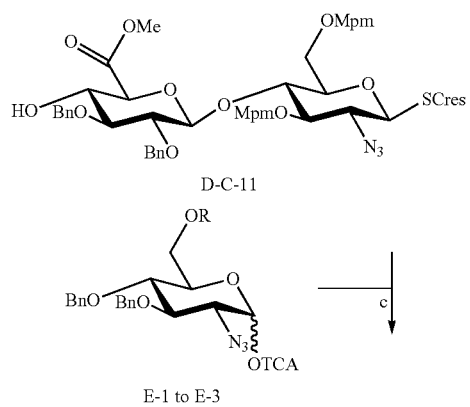

D-C-11

E-1 to E-3 c ↓

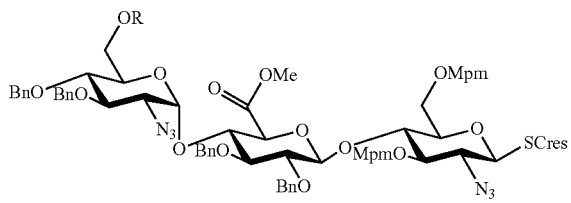

E-D-C-61: R = Mpm
E-D-C-72: R = Mp
E-D-C-73: R = Bz

Example 29: Syntheses of trisaccharides E-D-C-72 to E-D-C-73 and E-D-C-61, conditions: a) SOP 33; b) SOP 24; c) SOP 33.

Example 30

Syntheses of Trisaccharides C-B-A-1 to C-B-A-4

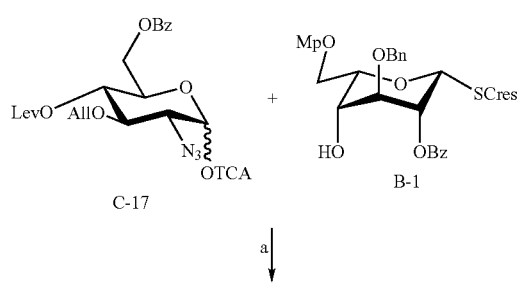

78
-continued

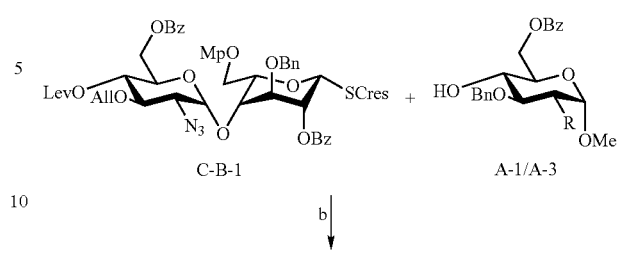

C-B-1 + A-1/A-3 b ↓

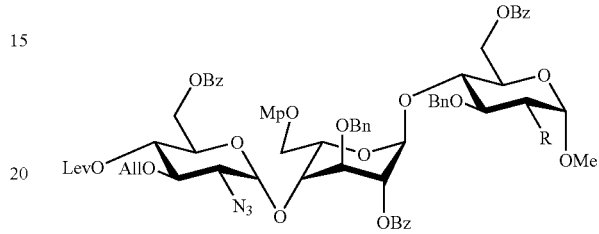

c ↓

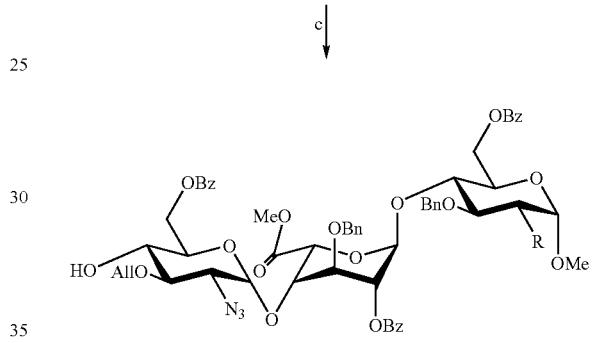

C-B-A-1: R = N₃
C-B-A-2: R = DTPMNH
C-B-A-3: R = N₃
C-B-A-4: R = DTPMNH

Example 30: Syntheses of trisaccharides C-B-A-1 to C-B-A-4, conditions: a) SOP 33; b) SOP 32a; c) 1. SOP 27; 2. SOP 20; 3. SOP 16; 4. SOP 24.

Example 31

Synthesis of Trisaccharides C-B-A-5 to C-B-A-8

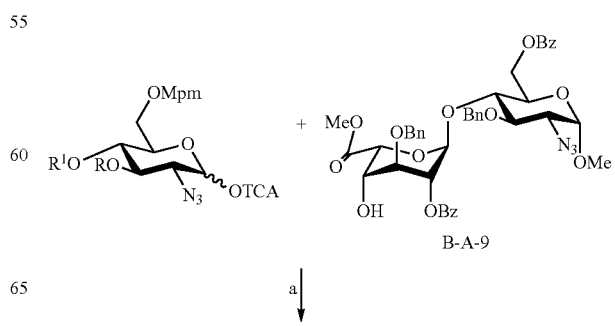

B-A-9 a ↓

-continued

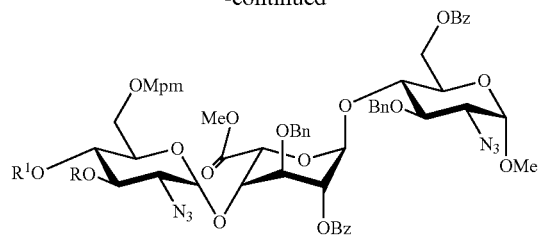

C-18: R = Bz, R¹ = Ac
C-19: R = Mpm, R¹ = Ac
C-20: R = Bz, R¹ = Lev
C-21: R = Mpm, R¹ = Lev
C-B-A-5: R = Bz, R¹ = Ac
C-B-A-6: R = Mpm, R¹ = Ac
C-B-A-7: R = Bz, R¹ = Lev
C-B-A-8: R = Mpm, R¹ = Lev

Example 31: Synthesis of trisaccharides C-B-A-5 and C-B-A-8, conditions: a) SOP 33, (50% for C-B-A-5, α/β mixture).

Compound C-B-A-5:

C-B-A-5 was formed according to SOP 33 with ether as solvent at −20° C. and TBDMSOTf as promoter in 50% yield (as α/β-mixture).

$M_{found}$=1269.65 (M+H+ $H_2O$)$^+$, $M_{calc}$=1250.43 (M$^+$).

Example 32

Syntheses of D-C-B Trisaccharides D-C-B-1 to D-C-B-3

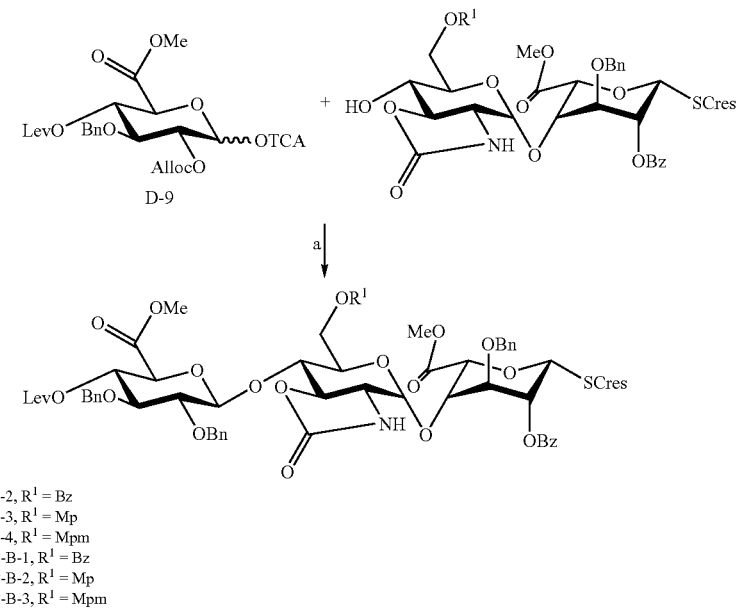

C-B-2, R¹ = Bz
C-B-3, R¹ = Mp
C-B-4, R¹ = Mpm
D-C-B-1, R¹ = Bz
D-C-B-2, R¹ = Mp
D-C-B-3, R¹ = Mpm

Example 32: Syntheses of D-C-B-trisaccharides D-C-B-1 to D-C-B-3, conditions: a) 1. SOP 33; 2. SOP 36; 3. SOP 37.

Example 33

Syntheses of D-C-B Trisaccharides D-C-B-4 to D-C-B-7

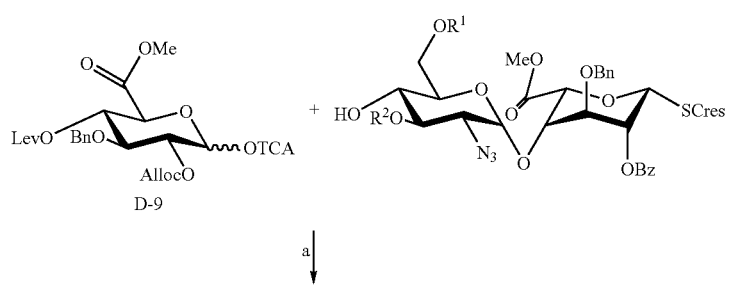

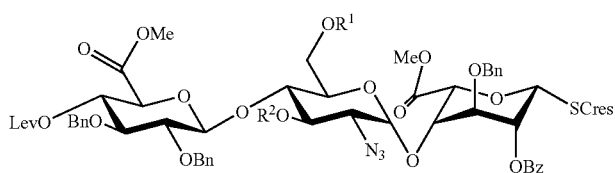
C-B-5: R$^1$ = Mpm, R$^2$ = Mpm,
C-B-6: R$^1$ = Mpm, R$^2$ = All,
C-B-7: R$^1$ = Mp, R$^2$ = Mpm,
C-B-8: R$^1$ = Mp, R$^2$ = All,
D-C-B-4: R$^1$ = Mpm, R$^2$ = Mpm,
D-C-B-5: R$^1$ = Mpm, R$^2$ = All,
D-C-B-6: R$^1$ = R$^2$ = Mpm,
D-C-B-7: R$^1$ = Mp, R$^2$ = All,
Example 33: Syntheses of D-C-B-trisaccharides D-C-B-4 to D-C-B-7, conditions: a) 1. SOP 33; 2. SOP 36; 3. SOP 37.
Example 34
Syntheses of Tetrasaccharides D-C-B-A-1 to D-C-B-A-2
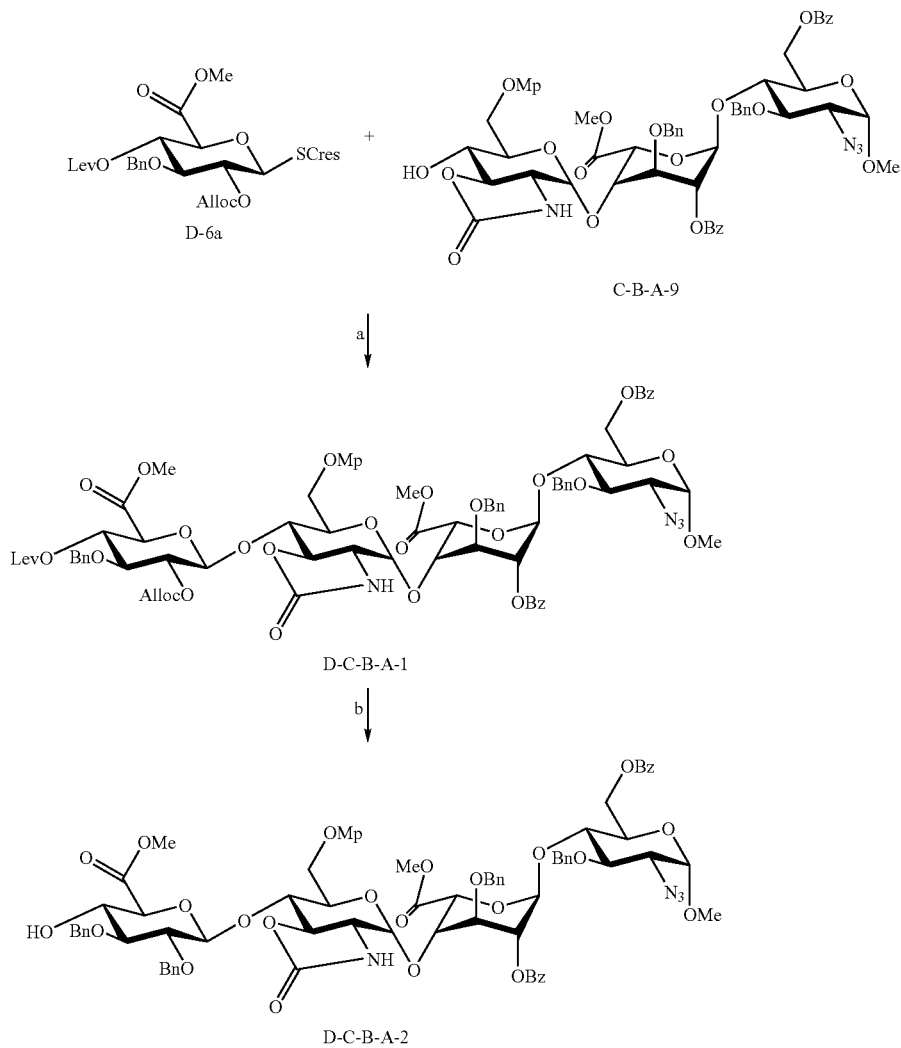

Example 34: Syntheses of tetrasaccharides D-C-B-A-1 and D-C-B-A-2, conditions: a) SOP 32a; b)1. SOP 36; 2. SOP 37; 3. SOP 24.

Example 35

Alternative Syntheses of Tetrasaccharides D-C-B-A-2

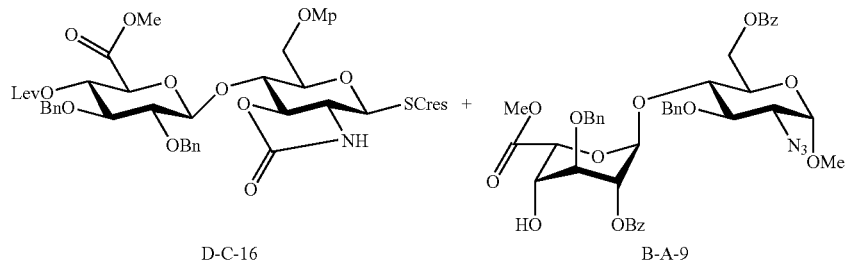

D-C-16     B-A-9

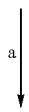

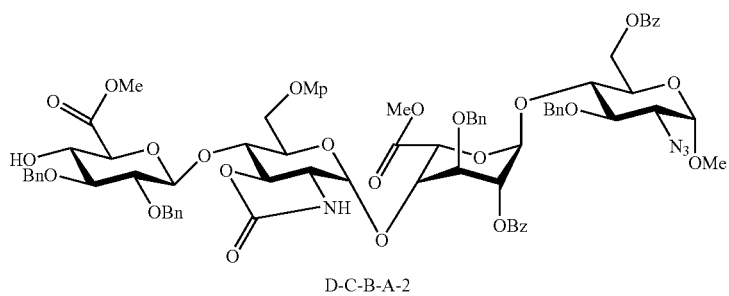

D-C-B-A-2

Example 35: Alternative synthesis of tetrasaccharide D-C-B-A-2, conditions: a) 1. SOP 34; 2. SOP 24.

Example 36

Syntheses of Tetrasaccharides D-C-B-A-3 to D-C-B-A-8

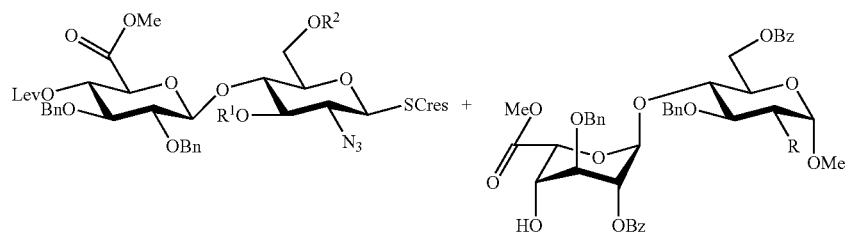

D-C-15: $R^1$ = Mpm, $R^2$ = Mpm     B-A-9: R = $N_3$
D-C-17: $R^1$ = Mpm, $R^2$ = Mp       B-A-10: R = DTPMNH
D-C-18: $R^1$ = Mpm, $R^2$ = Bz

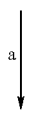

-continued
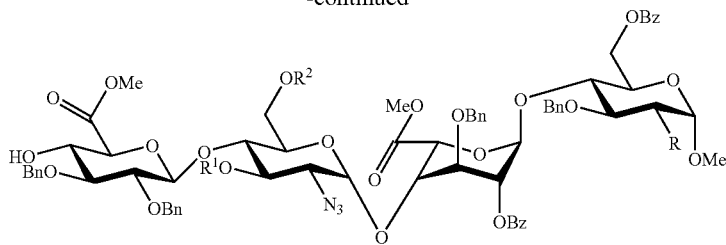
D-C-B-A-3: R = DTPMNH, R¹ = Mpm, R² = Mpm,
D-C-B-A-4: R = DTPMNH, R¹ = Mpm, R² = Bz
D-C-B-A-5: R = DTPMNH, R¹ = Mpm, R² = Mp
D-C-B-A-6: R = N₃, R¹ = Mpm, R² = Mpm,
D-C-B-A-7: R = N₃, R¹ = Mpm, R² = Bz
D-C-B-A-8: R = N₃, R¹ = Mpm, R² = Mp
Example 36: Syntheses of tetrasaccharides D-C-B-A-3 to D-C-B-A-8, conditions: a) 1 SOP 32b; 2. SOP 24.
Example 37
Syntheses of Tetrasaccharides E-D-C-B-1 to E-D-C-B-4
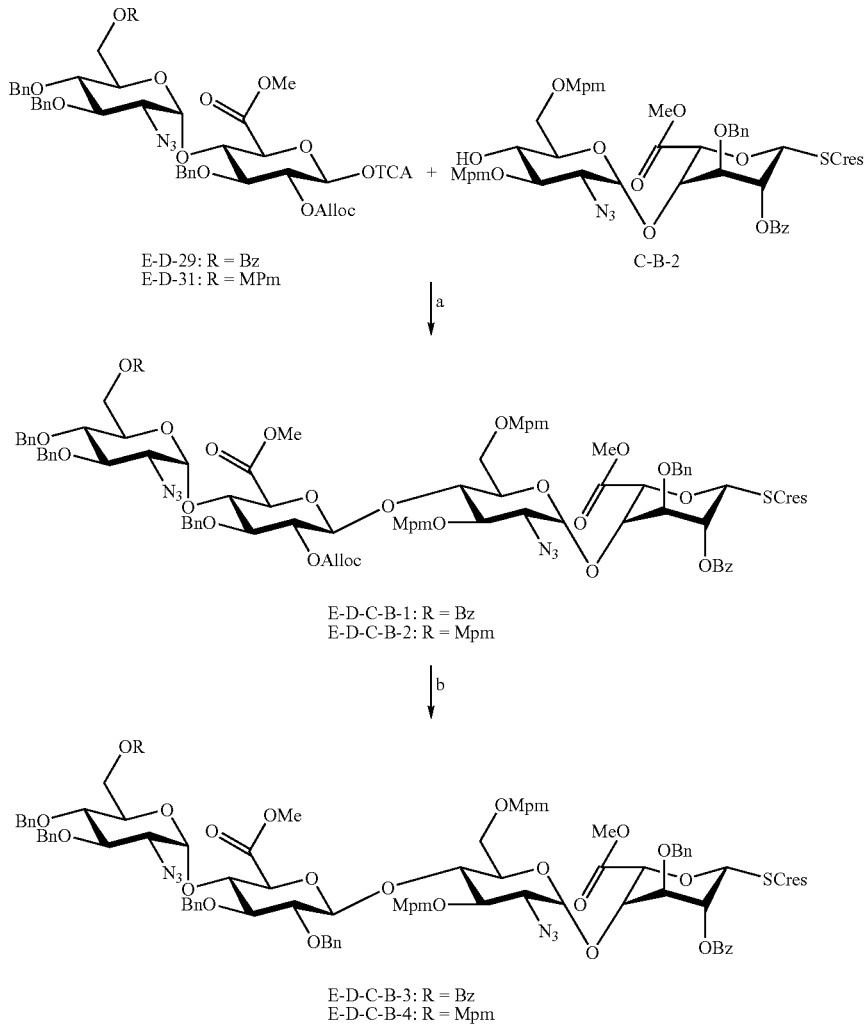

Example 37: Syntheses of tetrasaccharides E-D-C-B-1 to E-D-C-B-4, conditions: a) SOP 33; b) 1. SOP 36; 2. SOP 37.
Example 38
Syntheses of Blocks E-D-C-B-5 to E-D-C-B-8
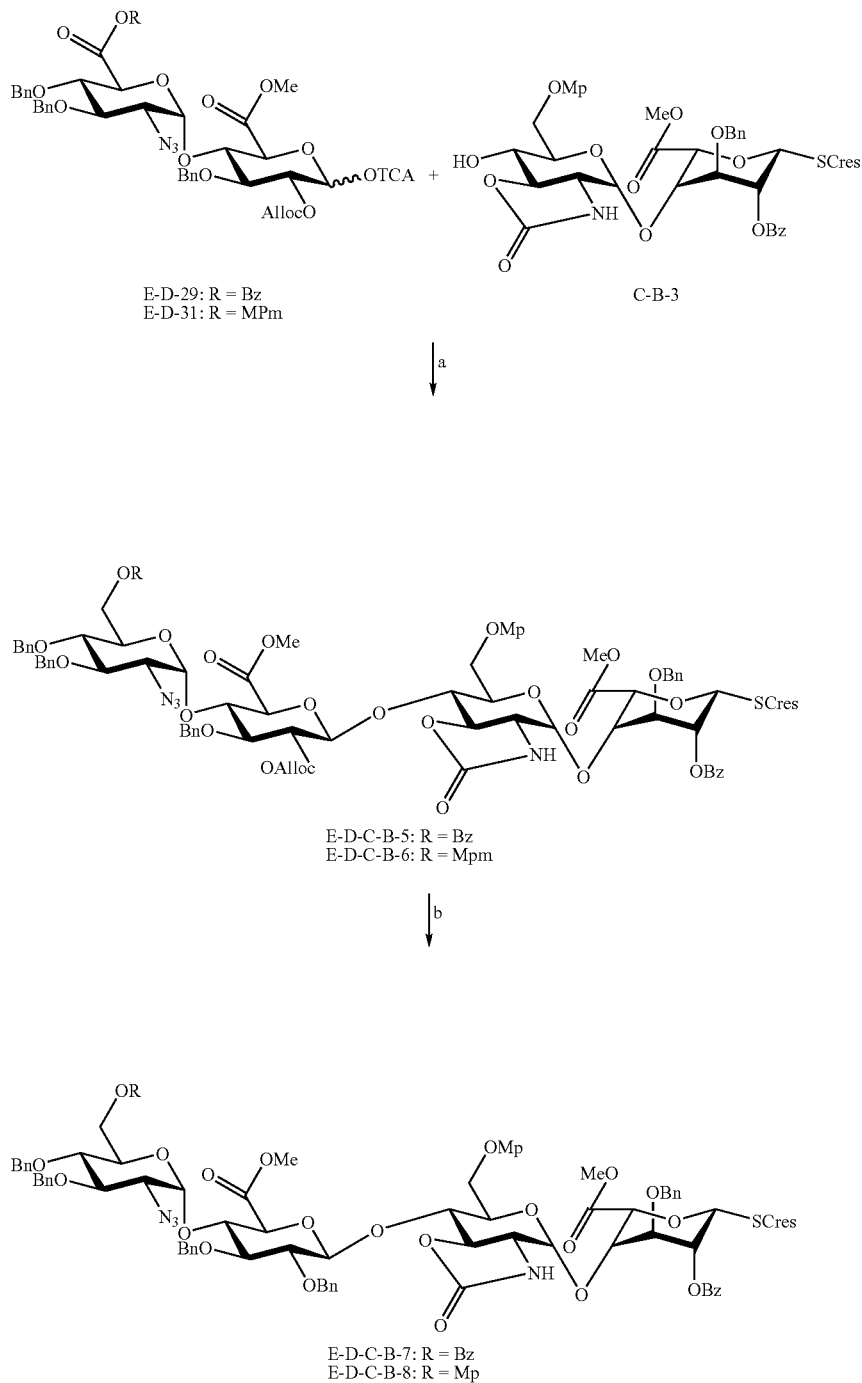
Example 38: Syntheses of tetrasaccharides E-D-C-B-5 to E-D-C-B-8, conditions: a) SOP 33; b) 1. SOP 36; 2. SOP 37.

Example 39
Syntheses of E-D-C-B-A Pentasaccharides P-1 and P-2
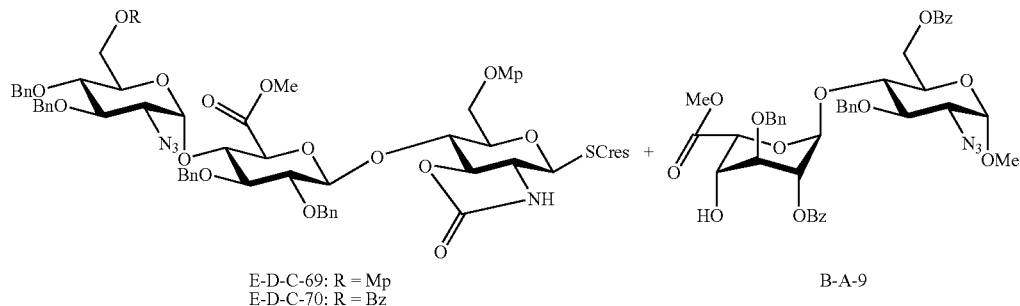
E-D-C-69: R = Mp
E-D-C-70: R = Bz
B-A-9
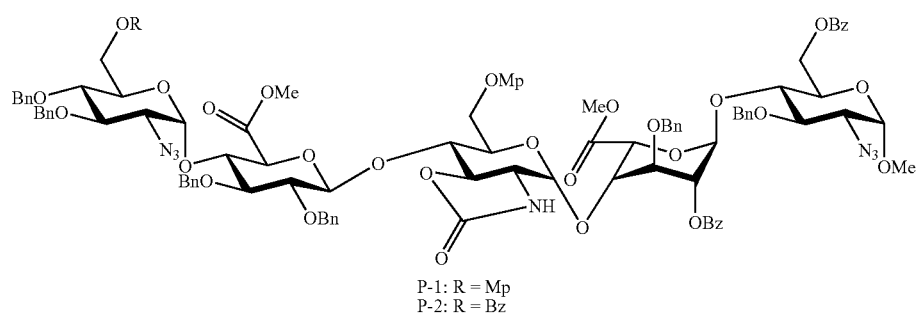
P-1: R = Mp
P-2: R = Bz
Example 39: Syntheses of E-D-C-B-A pentasaccharides P-1 and P-2, conditions: a) SOP 34.
Example 40
Synthesis of E-D-C-B-A Pentasaccharides P-3 to P-26
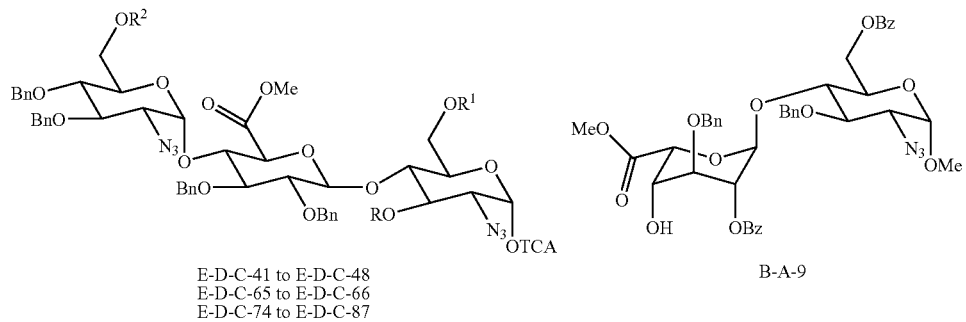
E-D-C-41 to E-D-C-48
E-D-C-65 to E-D-C-66
E-D-C-74 to E-D-C-87
B-A-9

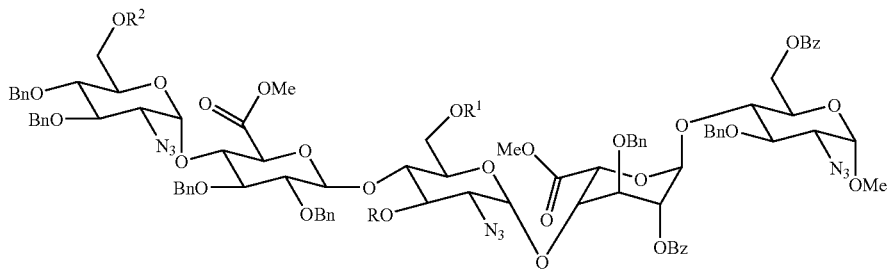

P3: R = All, R¹ = Mpm, R² = Bz
P4: R = All, R¹ = Mp, R² = Bz
P5: R = All, R¹ = Mpm, R² = Mpm
P6: R = All, R¹ = Mp, R² = Mpm
P7: R = All, R¹ = Mp, R² = Mp
P8: R = All, R¹ = Mpm, R² = Mp
P9: R = All, R¹ = Mpm, R² = TBDPS
P10: R = All, R¹ = Mp, R² = TBDPS
P11: R = Mpm, R¹ = Mpm, R² = Bz
P12: R = Mpm, R¹ = Mp, R² = Bz
P13: R = Mpm, R¹ = Mpm, R² = Mpm
P14: R = Mpm, R¹ = Mp, R² = Mpm
P15: R = Mpm, R¹ = Mp, R² = Mp
P16: R = Mpm, R¹ = Mpm, R² = Mp
P17: R = Mpm, R¹ = Mpm, R² = TBDPS
P18: R = Mpm, R¹ = Mp, R² = TBDPS
P19: R = Bz, R¹ = Mpm, R² = Bz
P20: R = Bz, R¹ = Mp, R² = Bz
P21: R = Bz, R¹ = Mpm, R² = Mpm
P22: R = Bz, R¹ = Mp, R² = Mpm
P23: R = Bz, R¹ = Mpm, R² = Mp
P24: R = Bz, R¹ = Mp, R² = Mp
P25: R = Bz, R¹ = Mpm, R² = TBDPS
P26: R = Bz, R¹ = Mp, R² = TBDPS

Example 40: Synthesis of E-D-C-B-A pentasaccharide P-3 to P-26, conditions: a) SOP 33 (75% for P-19 as an α/β mixture).

Compound P-19:

P-19 was formed according to SOP 33 with dichloromethane as solvent at −20° C. and TMSOTf as promotor;

$M_{found}$=2068.76 (M+H+ $H_2O$)⁺, $M_{calc}$=2049.74 (M⁺).

Example 41

Alternative Syntheses of E-D-C-B-A Pentasaccharides P-11, P-12, P-19, P-20 and P-27

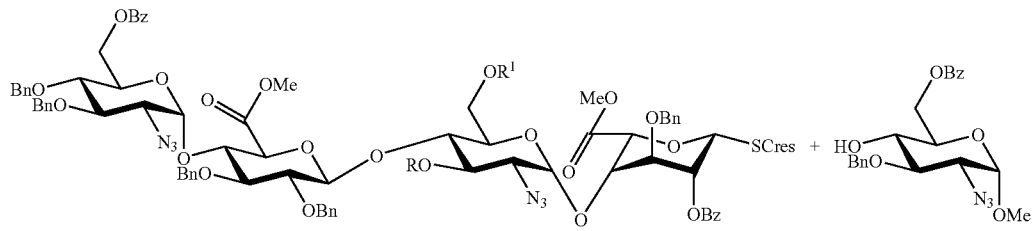

E-D-C-B-3: R = Mpm, R¹ = Mpm
E-D-C-B-9: R = Mpm, R¹ = Bz,
E-D-C-B-10: R = Mpm, R¹ = Mp
E-D-C-B-11: R = Bz, R¹ = Mp
E-D-C-B-12: R = Bz, R¹ = Mpm

A-1 a ↓

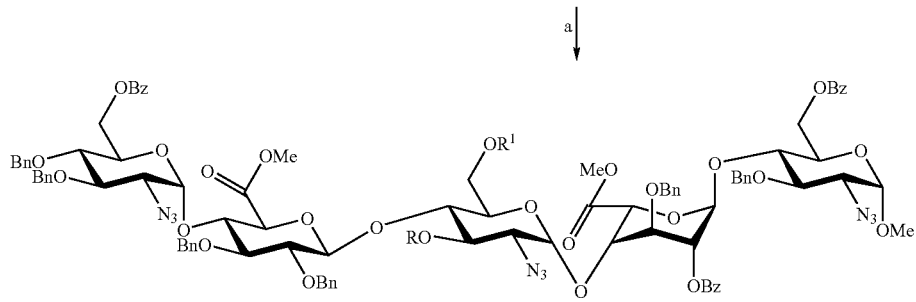

P-11: R = Mpm, R¹ = Mpm
P-12: R = Mpm, R¹ = Mp
P-19: R = Bz, R¹ = Mpm
P-20: R = Bz, R¹ = Mp
P-27: R = Mpm, R¹ = Bz

Example 41: Alternative syntheses of E-D-C-B-A pentasaccharides P-11, P-12, P-19, P-20 and P-27, conditions: a) SOP 32a.
Example 42
Alternative Syntheses of some E-D-C-B-A Pentasaccharides
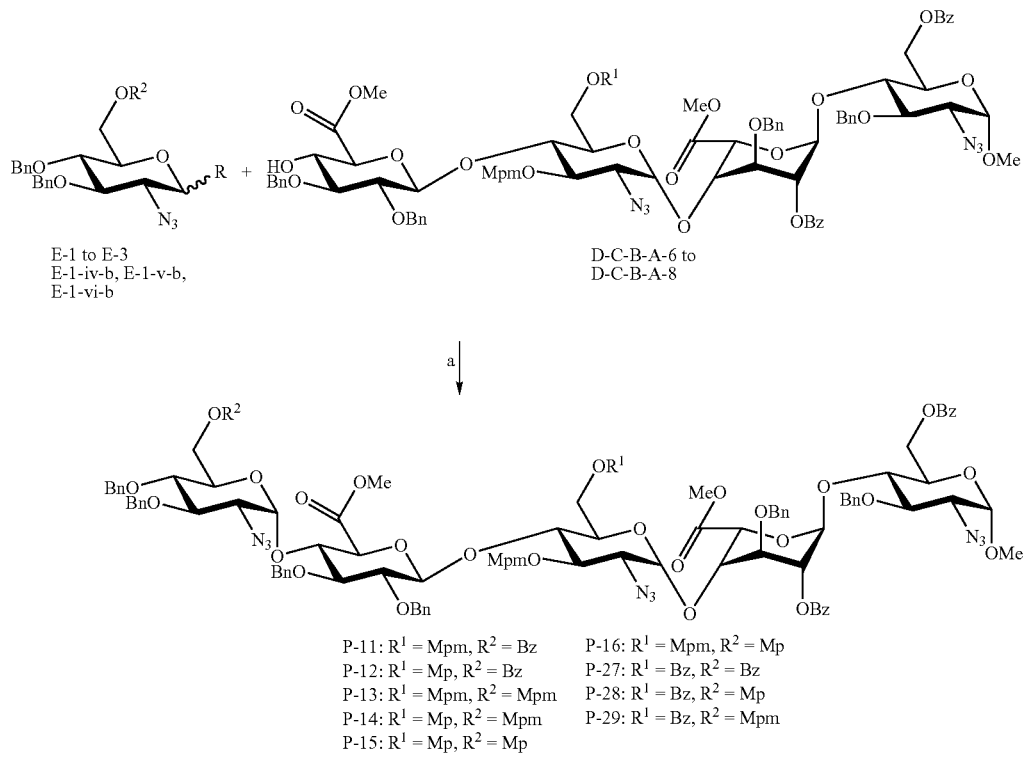
Example 42: Alternative syntheses of some E-D-C-B-A pentasaccharides, conditions: a) SOP 32a (for R=SCres) or SOP 33 (for R=OTCA).
Example 43
Synthesis of Pentasaccharide P-13 and P-30
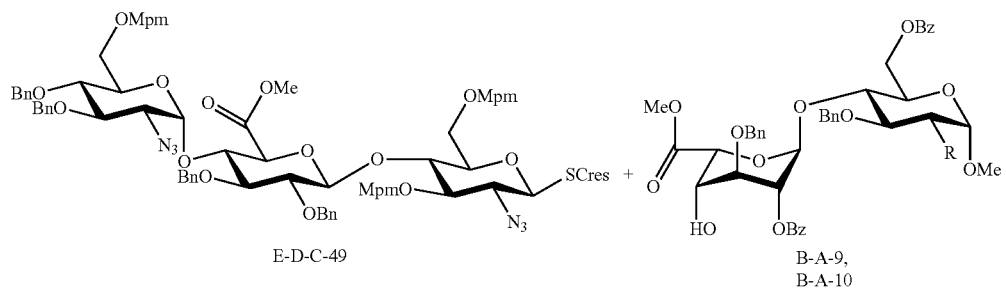

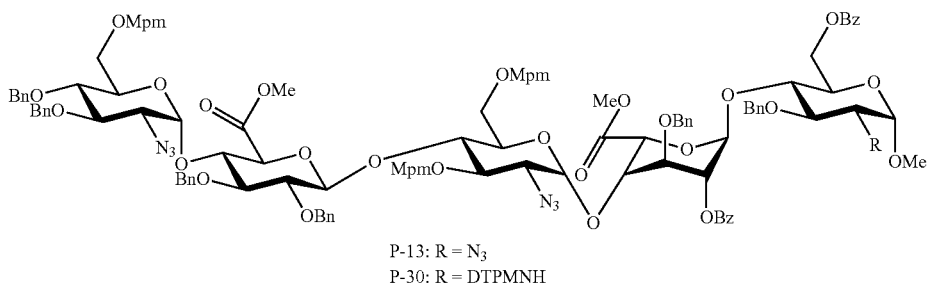

P-13: R = N₃
P-30: R = DTPMNH

Example 43: Formation of pentasaccharides P-13 and P-30, conditions: a) SOP 32a.

Example 44

Formation of Pentasaccharide P-19 and P-31

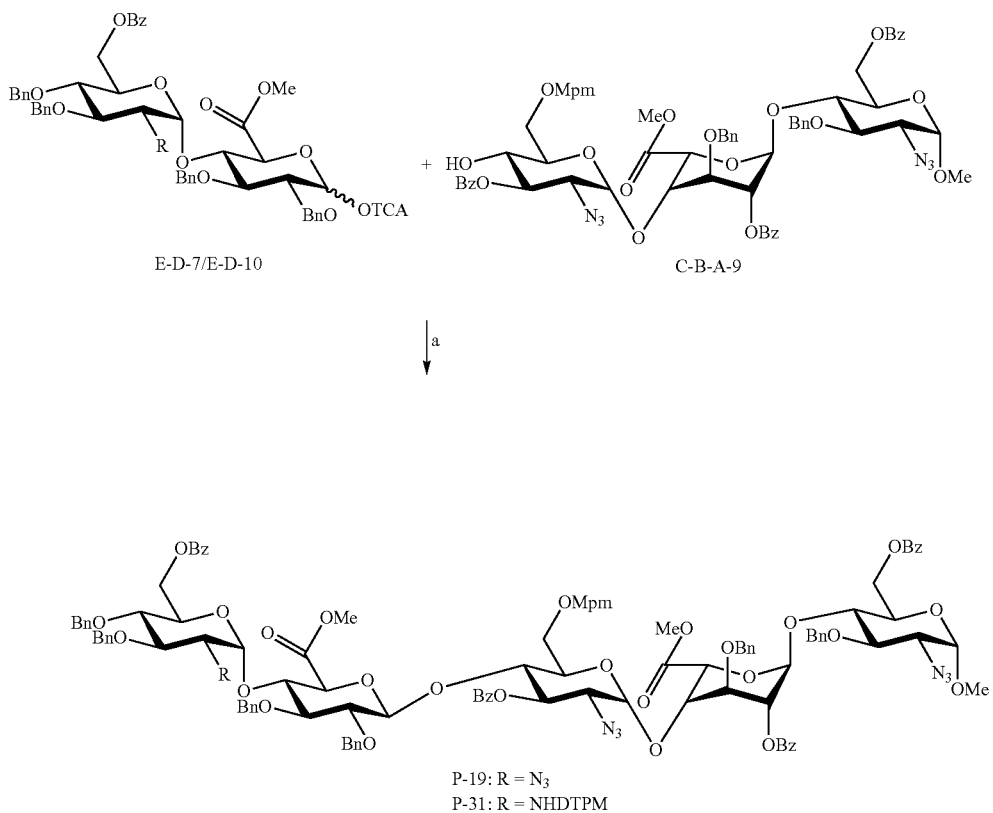

P-19: R = N₃
P-31: R = NHDTPM

Example 44: Formation of pentasaccharide P-19 and P-31 conditions: a) SOP 33

Example Preparation of P19

A mixture of O-(2-azido-6-O-benzoyl-3,4-di-O-benzyl-2-deoxy-α-D-glucopyranosyl)-(1-4)-(methyl 2,3-di-O-benzyl-β-D-glucopyranosyl uronate)-(1→4)-2-azido-3-O-benzoyl-2-deoxy-6-O-p-methoxybenzyl-α-D-glucopyranosyltrichloroacetimidate (30.0 mg, 21.2 µmol) and methyl (methyl 2-O-benzoyl-3-O-benzyl-(α-L-idupyranosyluronate)-(1→4)-2-azido-3-O-benzyl-6-O-benzoyl-2-deoxy-α-D-glucopyranoside (15.4 mg 19.3 µmol) and 100 mg of molecular sieves 4 Å in 1.5 mL dry dichloromethane was treated with TBDMSOTf (0.97 µl, 4.24 µmol) at −20° C. for 20 hours. The reaction was quenched, filtered and concentrated. Further purification of the title compound was achieved by silica gel chromatography Yield: 15.83 mg (40%), R$_f$=0.30 (toluene/ethyl acetate=9/1).

Example 45

Partial Deprotection of Pentasaccharide P-19

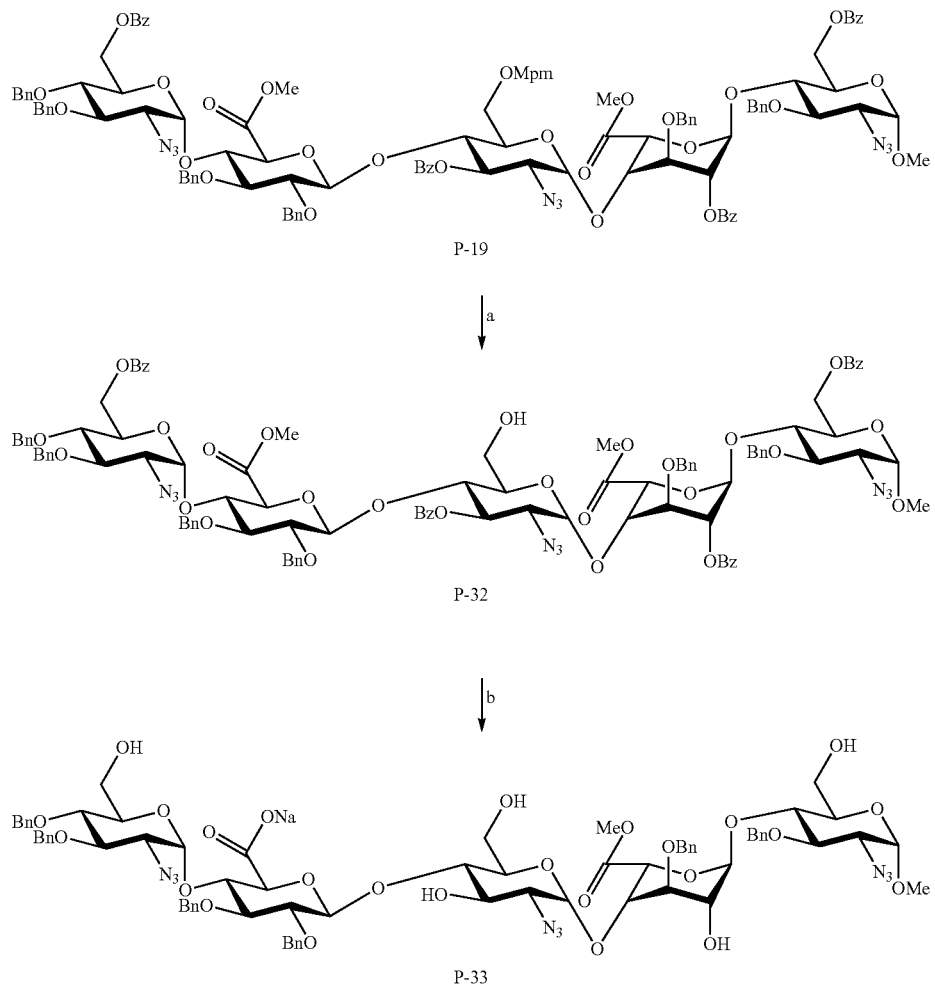

Example 45: Partial deprotection of pentasaccharide P-19, conditions: a) SOP 28, 84%; b) SOP 39, 86%.

Compound P-33:

$M_{found}$=1503.5 (M-N$_2$+2H)$^+$, $M_{calc}$=1529.51 (M$^+$).

To ease the structural proof, a small part of P-33 was transformed into the bis methyl uronurate derivative and characterized via NMR-spectroscopy. Characteristic $^1$H-NMR-spectral regions are shown in FIG. 1.

$M_{found}$=1514.62 (M+H)$^+$, $M_{calc}$=1513.58 (M$^+$).

Example 46

Partial Deprotection of Pentasaccharide P-30, Containing a DTPM-Group as Amino Protection

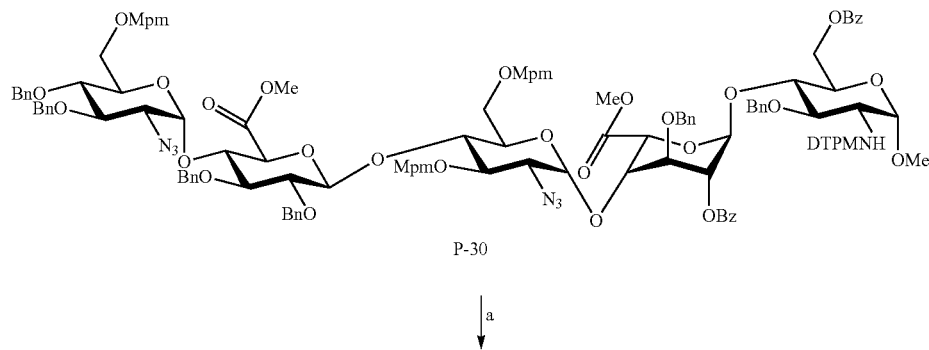

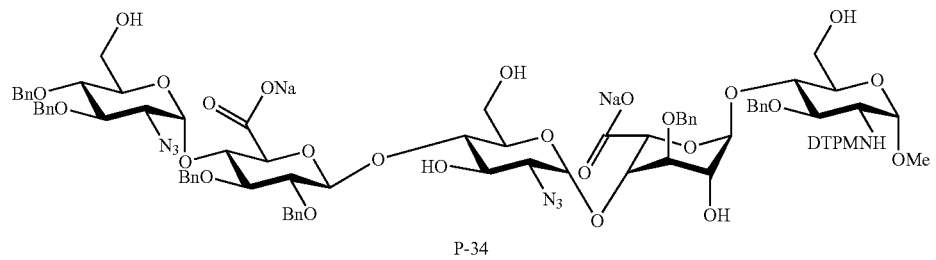
P-34
↓ b
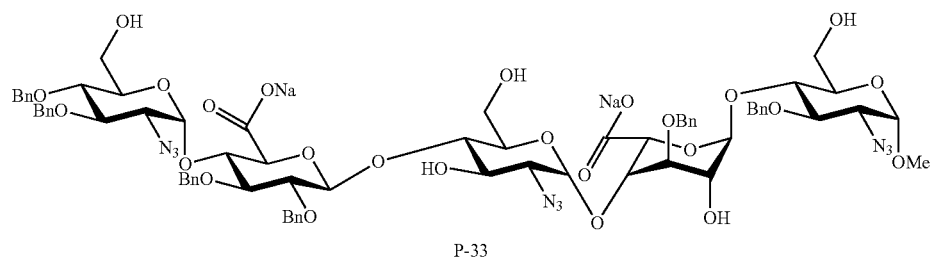
P-33
Example 46: Partial deprotection of pentasaccharide P-30, containing a DTPM-group as amino protection, conditions: a) 1. SOP 28; 2. SOP 39; b) 1. SOP 11 with MeNH$_2$ as primary amine and MeOH as solvent; 2. SOP 12.
Example 47
Partial Deprotection of Pentasaccharide P-1 Containing a Cyclic Carbamate as Amino Protection
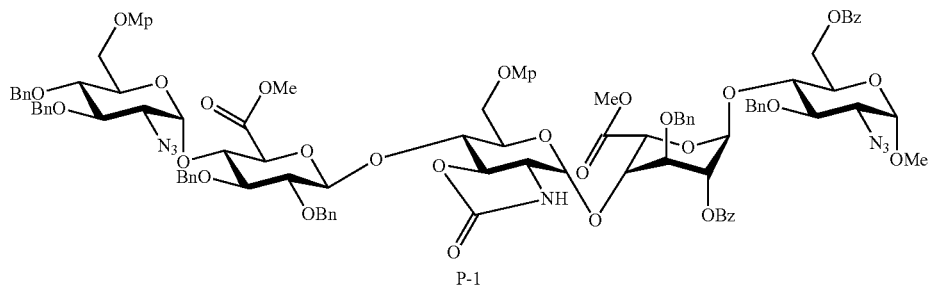
P-1
↓ a
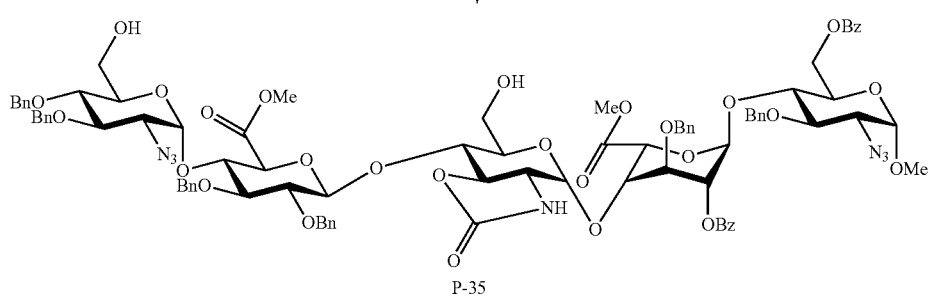
P-35
↓ b

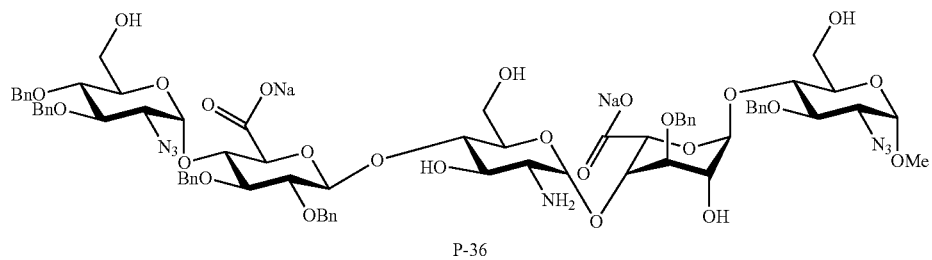
P-36
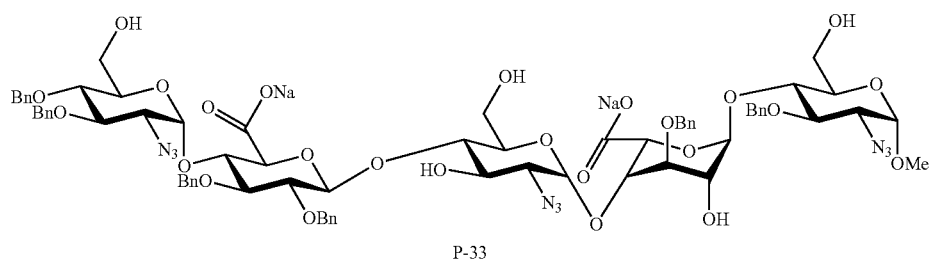
P-33
Example 47: Partial deprotection of pentasaccharide P-1, containing a cyclic carbamate as amino protection, conditions: a) SOP 27; b) SOP 39; c) SOP 12.
Example 48
Deprotection Protocol for Pentasaccharides P-37 of claim 4
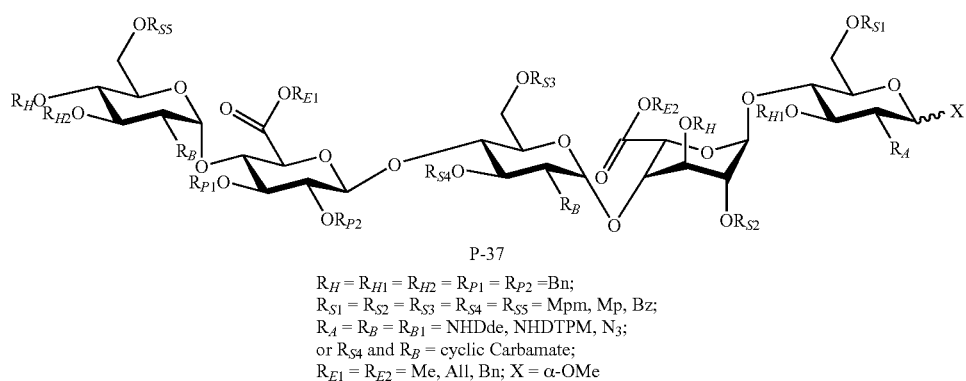
P-37
$R_H = R_{H1} = R_{H2} = R_{P1} = R_{P2} =$ Bn;
$R_{S1} = R_{S2} = R_{S3} = R_{S4} = R_{S5} =$ Mpm, Mp, Bz;
$R_A = R_B = R_{B1} =$ NHDde, NHDTPM, N$_3$;
or $R_{S4}$ and $R_B$ = cyclic Carbamate;
$R_{E1} = R_{E2} =$ Me, All, Bn; X = α-OMe
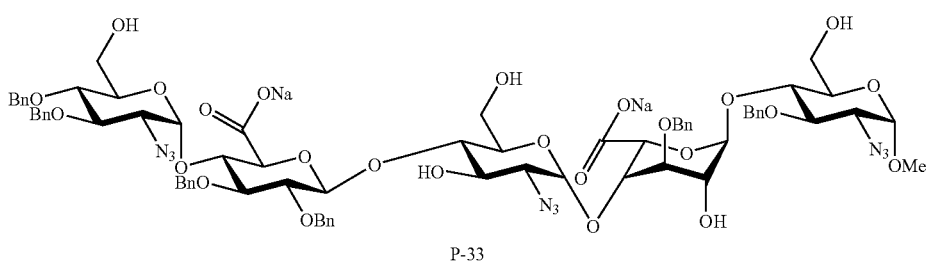
P-33

Example 48: Deprotection protocol for pentasaccharides P-37 of claim 4, conditions: a) 1. SOP 27 and 28; 2. SOP 39; 3. SOP 11 with MeNH$_2$ as primary amine and MeOH as solvent; 4. SOP 12.

Example 49

Transformation of Pentasaccharide P-33 into the O- and N-Sulfated Pentasaccharide P-40

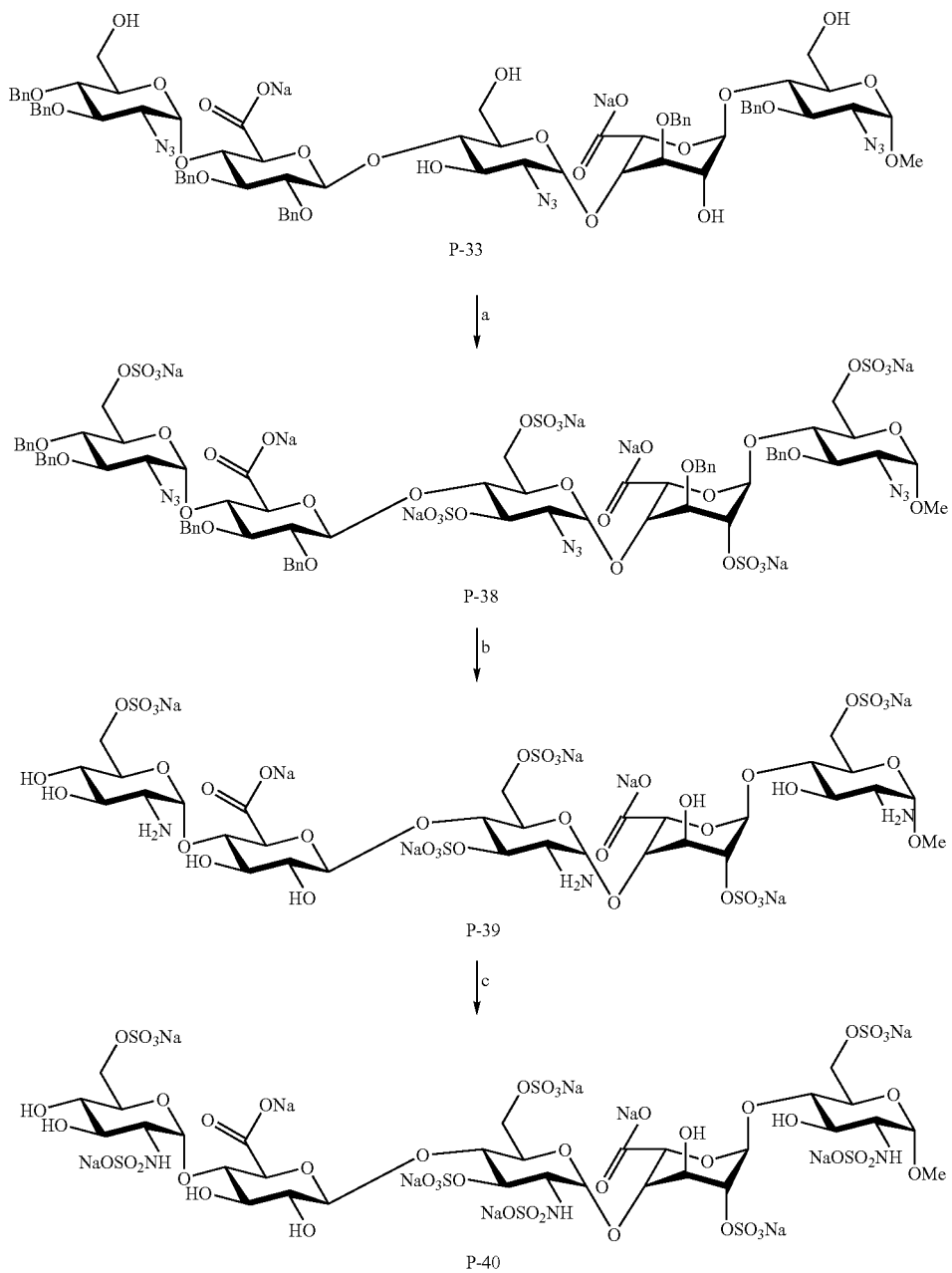

Example 49: Transformation of pentasaccharide P-33 into the O- and N-sulfated pentasaccharide P-40, conditions: a) SO$_3$×NMe$_3$, DMF, 50° C.; b) H$_2$ (70 psi), Pd/C, H$_2$O; c) SO$_3$× Pyridine, H$_2$O, pH=9.5. The transformation of P-33 into P-40 has been performed according to literature: Petitou et al., *Carbohydr. Res.* 1987, 167, 67-75.

Figure 2:
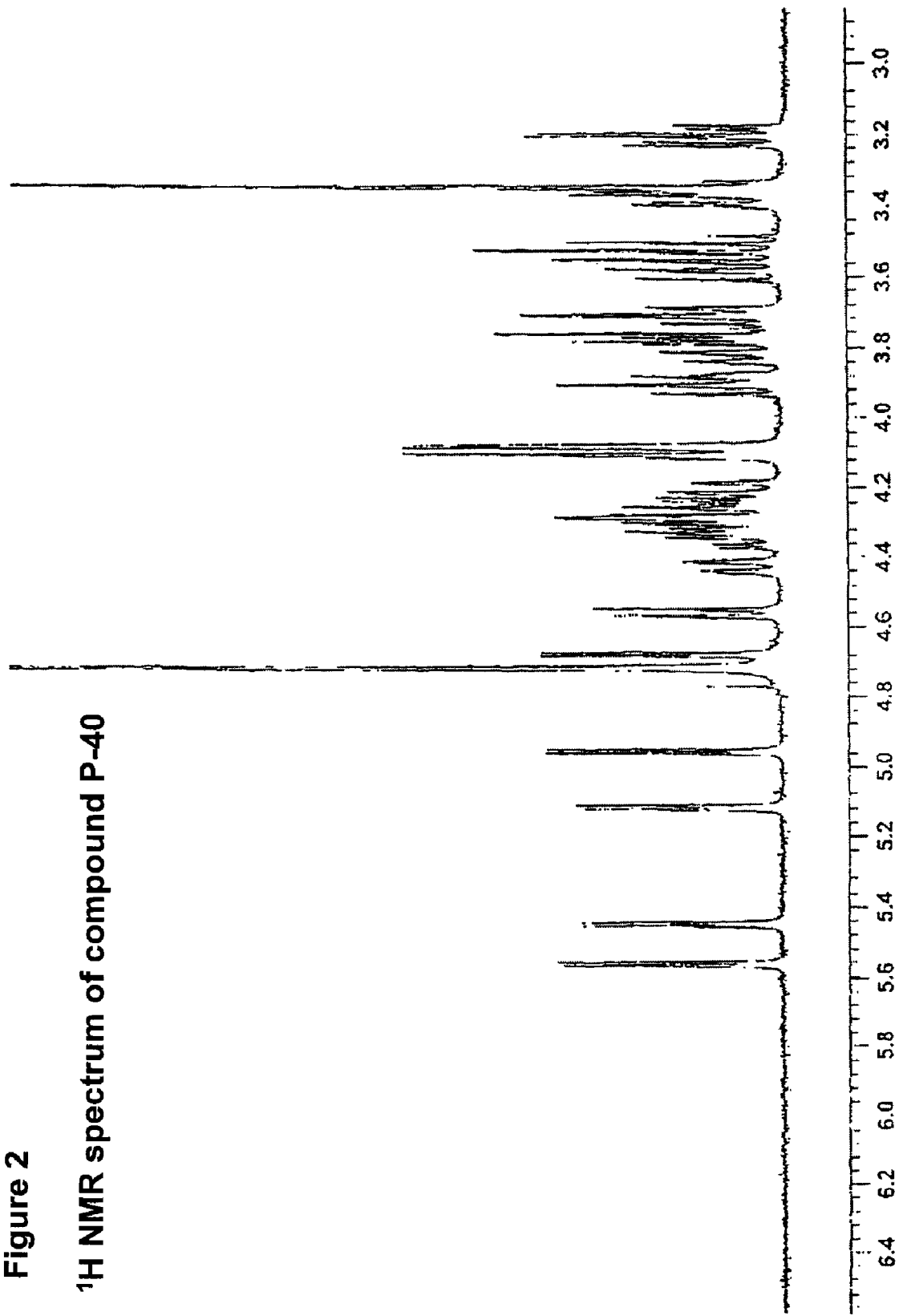
FIG. 2 is a proton NMR spectrum of the compound P-40.

The $^1$H-NMR (400 MHz, D$_2$O) of P-40 is shown in FIG. 2.

REFERENCES

[1] Lindahl, U., Backdtrom, G., Thunberg, L., Leder, I. G., *Proc. Natl. Acad. Sci. USA,* 1980, Vol. 77, No. 11, 6551-6555; Reisenfeld, J., Thunberg, L., Hook, M., & Lindahl, U., *J. Biol. Chem.,* 1981, Vol. 256, No. 5, 2389-2394.

[2] Choay, J., Lormeau, J-C., Petitou, M., Sinay, P., and Fareed, J., *Annals New York Academy of Sciences,* 1981, 370, 644-649.

[3] Pierre Sinaÿ, Jean-Claude Jacquinet, *Carbohydrate Research,* 132, (1984), C$_5$-C$_9$.

[4] C. A. A. van Boeckel, T. Beetz, J. N. Vos, A. J. M. de Jong, S. F. van Aelst, R. H. van den Bosch, J. M. R. Mertens and F. A. van der Vlugt., *J. Carbohydrate Chemistry,* 4(3), 1985, 293-321.

[5]. J. Choay, M. Petitou, J. C. Lormeau, P. Sinay, J. Fareed, *Ann. NY Acad. Sci.*, 1981, 370, 644-649.

[6] J Choay et. al., *Biochem. Biophys. Res. Commun.*, 1983, 116, 492-499.

The invention claimed is:

1. A monosaccharide of General Formula X

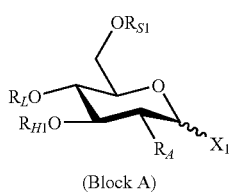

General Formula X (Block A)

in which the ring is of the D-Gluco stereochemistry; wherein $X_1$ is selected from the group consisting of alpha or beta thiomethyl or thiocresyl or trichloroacetimidoyl or t-butyldiphenylsilyloxy, alpha methoxy;

$R_{H1}$ is selected from the group consisting of benzyl or substituted benzyl protecting group or $R_{H1}$ and $R_A$ can combine together to form a cyclic carbamate;

$R_A$ is selected from the group consisting of an azido function, an NH-Dde, NH-DTPM;

or $R_{H1}$ and $R_A$ can combine together to form a cyclic carbamate;

$R_{S1}$ is selected from the group consisting of 4-methoxyphenyl; 4-methoxybenzyl, benzoyl, and 4-chlorobenzoyl;

$R_L$ is selected from a hydrogen atom or a levulinoyl.

2. The monosaccharide of claim 1, wherein:

$R_A$ is azido or $R_A$ and $R_{H1}$ combine to form a cyclic carbamate.

3. The monosaccharide of claim 1, wherein $R_{H1}$ is benzyl.

4. A monosaccharide of General Formula XIII,

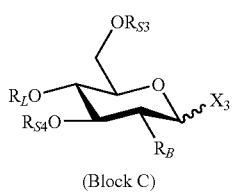

General Formula XIII (Block C)

in which the ring is of the D-Gluco stereochemistry; wherein:

$R_{S3}$ is selected from the group consisting of 4-methoxyphenyl; 4-methoxybenzyl, benzoyl, 4-chlorobenzoyl, allyloxycarbonyl and allyl;

$R_{S4}$ is selected from the group consisting of 4-methoxyphenyl, 4-methoxybenzyl, benzoyl, 4-chlorobenzoyl, and allyl, or $R_{S4}$ and $R_B$ may be combined to form a cyclic carbamate;

$R_B$ is selected from the group consisting of an azido function and an amine, or $R_{S4}$ and $R_B$ can combine together to form a cyclic carbamate;

$R_L$ is selected from the group consisting of a a hydrogen atom and a levulinoyl group;

$X_3$ is selected from the group consisting of a thiomethyl, thioethyl, thiophenyl, thiocresyl, trichloroacetimidoyl, and tert-butyldiphenylsilyloxy; and the stereochemistry may be alpha or beta.

5. A monosaccharide of General Formula XVI,

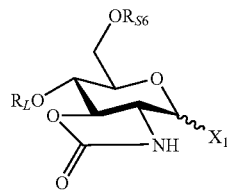

General Formula XVI (Common Intermediate for Blocks A, C and E)

wherein:

$X_1$ is selected from the group consisting of thiomethyl, thiocresyl, trichloroacetimidoyl, and a tbutyldiphenylsilyloxy; and the stereochemistry may be alpha or beta;

$R_L$ is selected from the group consisting of a hydrogen atom, a levulinoyl;

$R_{S6}$ is selected from the group consisting of 4-methoxyphenyl, 4-methoxybenzyl; benzoyl, 4-chlorobenzoyl, and tert-Butyldiphenylsilyl.

6. The monosaccharide of claim 1, wherein the monosaccharide is of the formula:

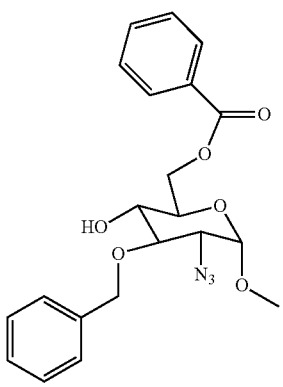

7. The monosaccharide of claim 4, wherein the monosaccharide is of the formula:

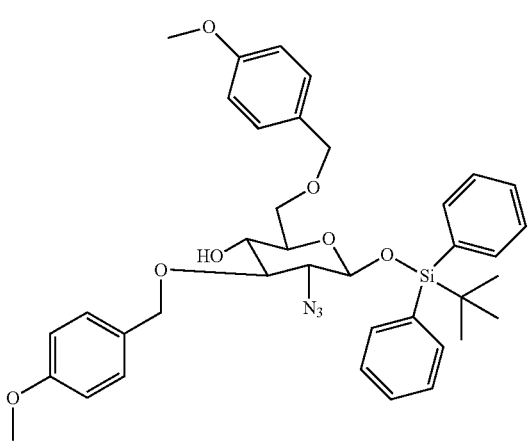

8. The monosaccharide of claim 4, wherein the monosaccharide is of the formula:

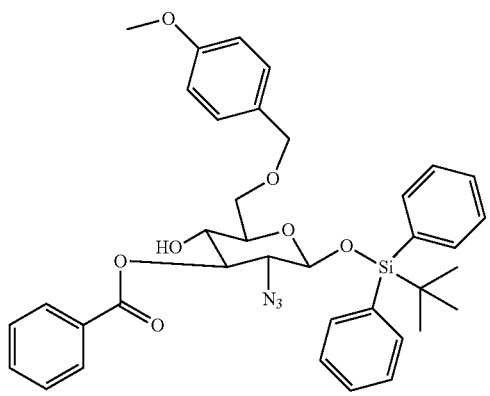

9. The monosaccharide of claim 4, wherein the monosaccharide is of the formula:

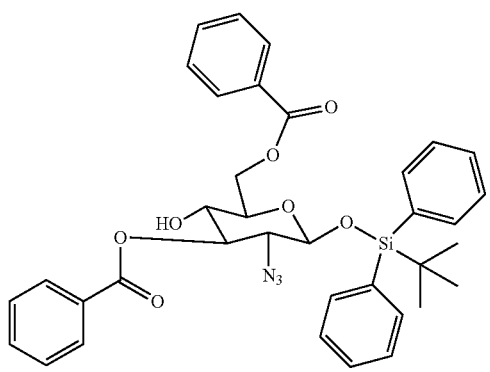

10. The monosaccharide of claim 4, wherein the monosaccharide is of the formula:

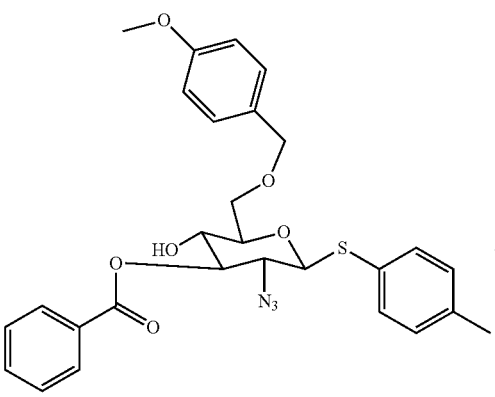

11. The monosaccharide of claim 4, wherein the monosaccharide is of the formula:

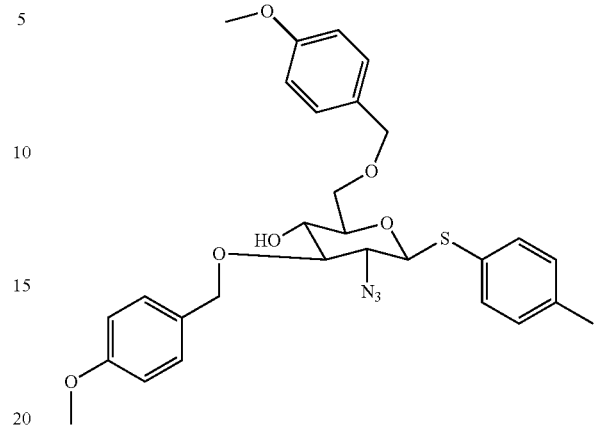

12. The monosaccharide of claim 4, wherein the monosaccharide is of the formula:

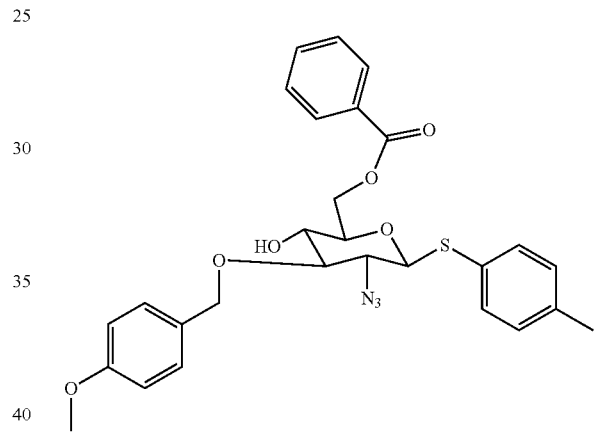

13. A monosaccharide of the formula:

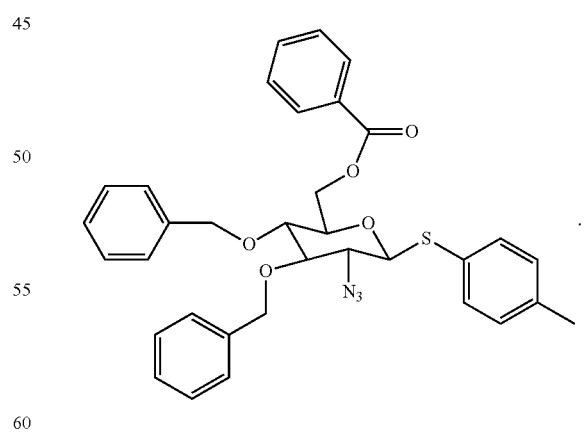

* * * * *